US007899524B2

(12) United States Patent
Kozel

(10) Patent No.: US 7,899,524 B2
(45) Date of Patent: Mar. 1, 2011

(54) SYSTEMS AND METHODS FOR DETECTING DECEPTION BY MEASURING BRAIN ACTIVITY

(75) Inventor: Frank Andrew Kozel, Southlake, TX (US)

(73) Assignee: MUSC Foundation for Research and Development, Charleston, SC (US)

( * ) Notice: Subject to any disclaimer, the term of this patent is extended or adjusted under 35 U.S.C. 154(b) by 1607 days.

(21) Appl. No.: 11/151,765

(22) Filed: Jun. 13, 2005

(65) Prior Publication Data

US 2006/0036152 A1    Feb. 16, 2006

Related U.S. Application Data

(63) Continuation-in-part of application No. 10/868,045, filed on Jun. 14, 2004.

(60) Provisional application No. 60/605,870, filed on Aug. 30, 2004.

(51) Int. Cl.
*A61B 5/04* (2006.01)
*A61B 5/05* (2006.01)

(52) U.S. Cl. ........................ 600/544; 600/410
(58) Field of Classification Search ................ 600/410, 600/544, 545
See application file for complete search history.

(56) References Cited

U.S. PATENT DOCUMENTS

| 4,932,416 A | 6/1990 | Rosenfeld |
| 4,941,477 A | 7/1990 | Farwell |
| 5,113,870 A | 5/1992 | Rossenfeld |
| 5,137,027 A * | 8/1992 | Rosenfeld .................... 600/544 |
| 5,170,780 A | 12/1992 | Rosenfeld |
| 5,363,858 A | 11/1994 | Farwell |
| 5,406,956 A | 4/1995 | Farwell |
| 5,467,777 A | 11/1995 | Farwell |
| 5,564,433 A | 10/1996 | Thornton |

(Continued)

FOREIGN PATENT DOCUMENTS

EP      1138260 A2    10/2001

(Continued)

OTHER PUBLICATIONS

Kozel, F. Andrew et al., "Regional Brain Correlates of Deception: a Pilot Study in Healthy Young Adults," American College of Neuropsychopharmacology 39th Annual Meeting, published Dec. 10, 2000, 2 pages.

(Continued)

*Primary Examiner*—Patricia C Mallari
(74) *Attorney, Agent, or Firm*—Wilmer Cutler Pickering Hale and Dorr LLP

(57) ABSTRACT

Methods for determining whether the brain activity of a human subject in response to a stimulus of interest or question of interest is characteristic of a state of interest, such as a deceptive state or a truthful state, are disclosed. Some methods include the use of control questions, including truthful control questions and deceptive control questions, to provide bases for comparison for responses to stimuli of interest or questions of interest. Some methods include the use of differences between two states, such as a deceptive state and a truthful state. In some methods, brain maps are generated and compared. Also disclosed are systems for detecting deception by measuring brain activity.

12 Claims, 4 Drawing Sheets

Neural Correlates of Deception

Model-Building Group (n=30)

Cluster 1    Cluster 4    Cluster 2

Model-Testing Group (n=31)

U.S. PATENT DOCUMENTS

| | | | |
|---|---|---|---|
| 5,676,138 A | 10/1997 | Zawilinski | |
| 5,833,600 A | 11/1998 | Young | |
| 5,846,207 A | 12/1998 | Rosenfeld | |
| 5,876,334 A | 3/1999 | Levy | |
| 5,957,859 A | 9/1999 | Rosenfeld | |
| 6,167,299 A | 12/2000 | Galchenkov et al. | |
| 6,198,958 B1 | 3/2001 | Ives et al. | |
| 6,453,194 B1 | 9/2002 | Hill | |
| 6,572,528 B2 | 6/2003 | Rohan et al. | |
| 6,754,524 B2 * | 6/2004 | Johnson, Jr. | 600/544 |
| 6,830,544 B2 | 12/2004 | Tanner | |
| 6,854,879 B2 | 2/2005 | Pavlidis | |
| 6,996,256 B2 | 2/2006 | Pavlidis | |
| 7,010,351 B2 | 3/2006 | Firlik et al. | |
| 7,069,067 B2 | 6/2006 | Kuth et al. | |
| 7,111,980 B2 | 9/2006 | Pavlidis et al. | |
| 2002/0062089 A1 | 5/2002 | Johnson | |
| 2002/0099295 A1 | 7/2002 | Gil et al. | |
| 2003/0120140 A1 | 6/2003 | Bango | |
| 2004/0143170 A1 | 7/2004 | DuRousseau | |
| 2005/0119547 A1 | 6/2005 | Shastri et al. | |
| 2005/0143629 A1 | 6/2005 | Farwell | |
| 2005/0154290 A1 | 7/2005 | Langleben | |
| 2006/0036152 A1 | 2/2006 | Kozel | |

FOREIGN PATENT DOCUMENTS

WO    WO-02/102238 A2    12/2002

OTHER PUBLICATIONS

Spence, Sean A., et al., "Behavioural and Functional Anatomical Correlates of Deception in Humans," NeuroReport, vol. 12, No. 13, Sep. 17, 2001, pp. 2849-2853.

"Your Cheating Brain," BBC News, www.bbcnews.co.ok, Nov. 12, 2001, 2 pages.

Young, Emma, "Brain Scans Can Reveal Liars," New Scientist, Nov. 12, 2001, 2 pages.

Vallis, Mary, "Brain Scan Can Detect Lies, Researchers Find," National Post Online, www.nationalpost.com, Nov. 12, 2001, 2 pages.

Vedantam, Shankar, "The Polygraph Test Meets Its Match," The Washington Post, Nov. 12, 2001, p. A02.

Hall, C.T., "Fib Detector Study Shows Brain Scan Detects Patterns of Neural Activity When Someone Lies," The San Francisco Chronicle, www.sfgate.com, Nov. 26, 2001, 3 pages.

O'Neil, John, "In the Lab: Zeroing in on a Lie's Home Base," www.uphs.upenn.edu, Dec. 4, 2001, 1 page.

Human Brain Operates Differently in Decpetion and Honesty, University of Pennsylvania Researchers Report, Science Daily, Nov. 13, 2001, 1 page.

Adler et al., Relationship of subjective and objective social status with psychological and physiological functioning: preliminary data in healthy white women, Health Psychology, 2000, pp. 586-592, 19(6).

Alary et al., "Cortical activation associated with passive movements of the human index finger: an MEG study," NeuroImage, 2002, pp. 691-696, 15.

Annett, "A classification of hand preference by association analysis," Br. J. Psychol., 1970, pp. 303-321, 61(3).

Ashburner et al., "Nonlinear spatial normalization using basis functions," Human Brain Mapping, 1999, pp. 254-266, 7.

Babiloni et al., "Human cortical EEG rhythms during long-term episodic memory task. A high-resolution EEG study of the HERA model," NeuroImage, 2004, pp. 1576-1584, 21.

Binder et al., "Human brain language areas indentified by functional magnetic resonance imaging," J. Neurosci., 1997, pp. 353-362, 17(1).

Bush et al., "The Counting Stroop: an Interference Task Specialized for Functional Neuroimaging-validation Study with Functional MRI, Human Brain Mapping," 1998, pp. 270-282, 6.

Cohen et al., "On the control of automatic processes: a parallel distributed processing count of the stroop effect," Psychological Rev., 1990, pp. 332-361, 97(3).

Collins et al., "Automatic 3D intersubject registration of MR volumetric data in standardized talairach space," J. Comput. Assist. Tomogr., 1994, pp. 192-205, 18(2).

Collins et al., "Design and construction of a realistic digital brain phantom," IEEE Trans. Med. Imag., 1998, pp. 463-468, 17(3).

Cox, "AFNI: software for analysis and visualization of functional magnetic resonance neuroimages," Comput. Biomed. Res., 1996, pp. 162-173, 29.

Ritter, Malcolm, "Brain Scan as Lie Detectors? A Lying Thief Checks it Out," USA Today, Copyright 2006, The Associated Press, 5 pages.

Critchley et al., "Volitional control of autonomic arousal: A functional magnetic resonance study," NeuroImage, 2002, pp. 909-919, 16.

Ekman et al., "Invited article: face, voice, and body in detecting deceit," J. Nonverbal Behav., 1991, pp. 125-135, 15(2).

Elliott et al., "Selective attention to emotional stimuli in a verbal go/no go task: an fMRI study," NeuroReport, 2000, pp. 1739-1744, 11(8).

Farwell et al., "The truth will out: Interrogative polygraphy ("lie detection") with event-related brain potentials," Psychophysiol., 1991, pp. 531-547, 28(5).

Feng et al., "CBF changes during brain activation: fMRI vs. PET," NeuroImage, 2004, pp. 443-446, 22.

Fernandez et al., "Language mapping in less than 15 minutes: Real-time functional MRI during routine clinical investigation," NeuroImage, 2001, pp. 585-594, 14.

Frackowiak et al., "Human brain function," Academic Press, San Diego CA, 1997, pp. 487-517.

Friston et al., "Assessing the significance of focal activations using their spatial extent," Human Brain Mapping, 1994, pp. 210-220, 1.

Friston et al., "Statistical parametric maps in functional imaging: A general linear approach, Human Brain Mapping," 1995, pp. 189-210, 2.

Furedy, "Lie Detection as Psychophysiological differentiation: Some fine lines," Psychophysiology, 1986, pp. 683-701, The Guilford Press New York NY.

Ganis et al., "Neural correlates of different types of deception: an fMRI investigation," Cerebral Cortex, Aug. 2003, pp. 830-836, vol. 13.

George et al., "Blunted left cingulate activation in mood disorder subjects during a response interference task (the stroop)," J. Neuropsychiatry, 1997, pp. 55-63, 9.

Silberman, Steve, "Don't Even Think About Lying," Wired Magazine, Copyright 2006, Lycos, Inc., 7 pages.

Kozel et al., "A pilot study of functional magnetic resonance imaging brain correlates of deception in health young men," J. Neuropsychiatry Clin. Neurosci., 2004, pp. 295-305, 16(3).

Kozel et al., "A replication study of the neural correlates of deception, Behavioral Neuroscience," 2004, pp. 852-856, 118(4).

Kozel et al., "Measuring brain changes associated with deception using 3T BOLD functional MRI," abstract No. 455 presented at the 9th International Conference on Functional Mapping of the Human Brain, New York NY, 2003.

Lancaster et al., "Automated labeling of the human brain: A preliminary report on the development and evaluation of a forward-transform method," Human Brain Mapping, 1997, pp. 238-242, 5.

Langleben et al., "Brain activity during simulated deception: An event-related functional magnet resonance study," NeuroImage, 2002, pp. 727-732, V.15.

Lee et al., "Detection of feigning memory impairment using functional MRI," Retrieved Jun. 14, 2006 from http://208.164.121.55/hbm2003/abstract/abstract187.htm.

Lee et al., "Lie Detection by functional magnetic resonance imaging, Human Brain Mapping," 2002, pp. 157-164, 15(3).

Lorberbaum et al., "Feasibility of using fMRI to study mothers responding to infant cries," Depression and Anxiety, 1999, pp. 99-104, 10.

Lubow et al., "Pupillary size in response to a visual guilty knowledge test: New technique for the detection of deception," J. Exp. Psychol.: Applied, 1996, pp. 164-177, 2(2).

MacDonald et al., "Dissociating the role of the dorsolateral prefrontal and anterior cingulate cortex in cognitive control," Science, 2000, pp. 1835-1838, 288.

Martin, Neuroanatomy, 2003, 3rd Edition, The McGraw-Hill Companies, pp. 377-407.

McGonigle et al., "Variability in fMRI: An examination of intersession differences," NeuroImage, 2000, pp. 708-734, 11.

Moule et al., "Amplification of xenon NMR and MRI by remote detection," Proc. Natl. Acad. Sci. USA, 2003, pp. 9122-9127, 100(16).

Noguchi et al., "An event-related optical topography study of cortical activatio induced by single-pulse transcranial magnetic stimulation," NeuroImage, 2003, pp. 156-162, 19.

Nunez et al., "Fabrication versus truth telling can be distinguished as a measure of cognitive load using fMRI in human subjects," Retrieved Jun. 14, 2006 from http://208.164.121.55/hbm2003/abstract/abstract488.htm.

O'Doherty et al., "Abstract reward and punishment representations in the human orbitofrontal cortex," Nature Neurosci., 2001, pp. 95-102, 4(1).

Ogawa et al., "Brain magnetic resonance imaging with contract dependent on blood oxygenation," Proc. Natl., Acad. Sci. USA, 1990, pp. 9868-9872, 87.

Oldfield, "The assessment and analysis of handedness: The edinburgh inventory," Neuropsychologia, 1971, pp. 97-113, 9.

Pardo et al., Localization of a human system for sustained attention by positron emission tomography, Nature, 1991, pp. 61-64, 349.

Pavlidis et al., "Seeing through the face of deception," Nature, 2002, p. 35, 415.

Raine et al., "Reduced prefrontal gray matter volume and reduced autonomic activity in antisocial presonality disorder," Arch. Gen. Psychiatry, 2000, pp. 119-12757.

Rauch et al., "Neuroimaging and neuropsychology of the striatum," Psychiatric Clin. N. Amer., 1997, pp. 741-768, 20(4).

Rorden et al., "Stereotaxic display of brain lesions," Behavioural Neurology, 2000, pp. 191-200, 12.

Samuel et al., "Exploring the temporal nature of hemodynamic responses of cortical motor areas using functional MRI, Neurology," 1998, pp. 1567-1575, 51.

Shastri et al., "A low-cost system for monitoring skin conductance during functional MRI," J. Magnet. Reson. Imaging, 2001, pp. 187-193, 14.

Shastri et al., "Skin conductance measurements during functional MRI," Proc. Intl. Soc. Mag. Reson. Med., 2000, p. 912, 8.

Sheehan et al., "Associations between lying and hypnosis: An empirical analysis," Brit. J. Exp. Clin. Hypnosis, 1988, pp. 87-94, 5(2).

Spence et al., A preliminary description of the behavioural and functional anatomical correlates of lying, NeuroImage, 2001, 13(6).

Sporer, The less travelled road to truth: Verbal cues in deception detection in accounts of fabricated and self-experienced events, Applied Cog. Psychol., 1997, pp. 373-397, 11.

Steenhuis et al., Different dimensions of hand preference that relate to skilled and unskilled activities, Cortex, 1989, pp. 289-304, 25.

Taga et al., Brain imaging in awake infants by near-infrared optical topography, Proc. Natl. Acad. Sci. USA, 2003, pp. 10722-10727, 100(19).

Tardif et al., Detection of feigned recognition memory impairment using the old/new effect of the event-related potential, Intl. J. Psychophysiology, 2000, pp. 1-9, 36.

Taylor et al., Isolation of specific interference processing in the stroop task: PET activation studies, NeuroImage, 1997, pp. 81-92, 6.

Thompson et al., Three-Dimensional statistical analysis of sulcal variability in the human brain, J. Neurosci., 1996, pp. 4261-4274, 16(13).

Turner et al., Brain function and personality in normal males: a SPECT study using statistical parametric mapping, NeuroImage, 2003, pp. 1145-1162, 19.

Tzourio-Mazoyer et al., Automated anatomical labeling of activations in SPM using a macroscopic anatomical parcellation of the MNI MRI single-subject brain, NeuroImage, 2002, pp. 273-289, 15.

Van Honk et al., Repetitive transcranial magnetic stimulation at the frontopolar cortex reduces skin conductance but not heart rate: reduced gray matter excitability in orbitofrontal regions, Arch. Gen. Psychiatry, 2001, pp. 973-974, 58.

Wicker et al., Brain regions involved in the perception of gaze: a PET study, NeuroImage, 1998, pp. 221-227, 8.

Wiley, Deception and detection in psychiatric diagnosis, Psychiatric Clin. N. Amer., 1998, pp. 869-893, 21(4).

Yankee, The current status of research in forensic psychophysiology and its application in the psychophysiological detection of deception, J. Forensic Sci., 1995, pp. 63-68, 40.

Robinson, Richard, "fMRI Beyond the Clinic: Will it Ever Be Ready for Prime Time?," PLoS Biology, vol. 2, Issue 6, Jun. 2004, pp. 0715-0717.

Wager, Tor D., and Nichols, Thomas E., "Optimization of Experimental Design in fMRI: A General Framework Using a Genetic Algorithm," NeuroImage 18, 2003, pp. 293-309.

"Neuroethics Needed," Nature, vol. 441, Issue No. 7096, Jun. 22, 2006, 1 page.

"Lure of Lie Dectors Spooks Ethicists," Nature Publishing Group, 2006, 2 pages.

Kozel, Andrew F., et al., "Detecting Deception Using Functional Magnetic Resonance Imaging," BIOL Psychiatry, Oct. 15, 2005, 58(8), pp. 605-613.

Spence, Sean A., et al., "'Munchausen's Syndrome by Proxy,' or a 'Miscarriage of Justice'? an Initial Application of Functional Neuroimaging to the Question of Guilt Versus Innocence," European Psychiatry, 2007, 6 pages.

Spence, Sean A., et al., "Speaking of Secrets and Lies: The Contribution of Ventrolateral Prefrontal Cortext to Vocal Deception," Accepted Manuscript to Appear in NeuroImage, Aug. 30, 2007, 35 pages.

Mobbs, Dean et al., "Law, Responsiblity, and the Brain," PLoS Biology, vol. 5, Issue 4, Apr. 2007, pp. 0693-0700.

Mohamed, Feroze B., Ph.D., et al., "Brain Mapping of Decpetion adn Truth Telling About an Ecologically Valid Situation: Functional MR Imaging and Polygraph Investigation—Initial Experience," Radiology, vol. 238, No. 2, Feb. 2006, pp. 679-688.

Marks, Donald H., Ph.d. et al., "Determination of Truth from Deception Using Funcational MRI and Cognitive Engrams," The Internet Journal of Radiology, vol. 5, No. 1, 2006, 23 pages.

Gamer, Matthias, et al., "Covariations Among fMRI Skin Conductance, and Behavioral Data During Processing of Concealed Information," Human Brain Mapping, vol. 28, 2007, pp. 1287-1301.

Langleben, Daniel D., "Telling the Truth from Lie in Individual Subjects with Fast Event-Related fMRI," Center for Cognitive Neuroscience, Neuroethics Publicatons, 2005, pp. 596-603.

Davatzikos, Christos, et al., "Classifying Spatial Patterns of Brain Activity with Machine Learning Methods: Application to Lie Detection," Center for Cognitive Neuroscience, Neuroethics Publications, 2005, 14 pages.

Kozel, F. Andrew et al., "Can Simultaneously Acquired Electrodermal Activity Improve Accuracy of fMRI Detection of Deception?," Jun. 29, 2007, 17 pages.

Abe, Nobuhito, "Neural Correlates of True Memory, False Memory and Deception," Cerebral Cortex Advance Access, Mar. 27, 2008, 9 pages.

Spence, Sean A., et al., "A Cognitive Neurobiological Account of Deception: Evidence from Functional Neuroimaging," The Royal Society, Phil. Trans. R. Soc. Lond. B, 359, 1755-1762, Nov. 26, 2004.

Nunez, Jennifer Maria, et al., "Intentional False Responding Shares Neural Substrates with Response Conflict and Cognitive Control," NeuroImage, 2004, 11 pages.

Critchley, Hugo, ., "Neural Activity Relating to Generation and Representation of Galvanic Skin Conductance Responses: A Functional Magnetic Resonance Image Study," Journal of Neuroscience, Apr. 15, 2000; 20(8): 3033-3040.

* cited by examiner

Figure 1
Neural Correlates of Deception
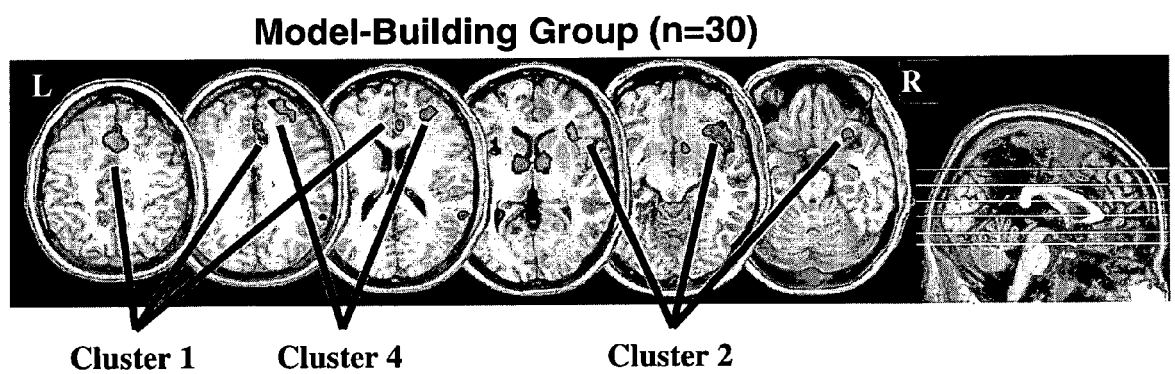
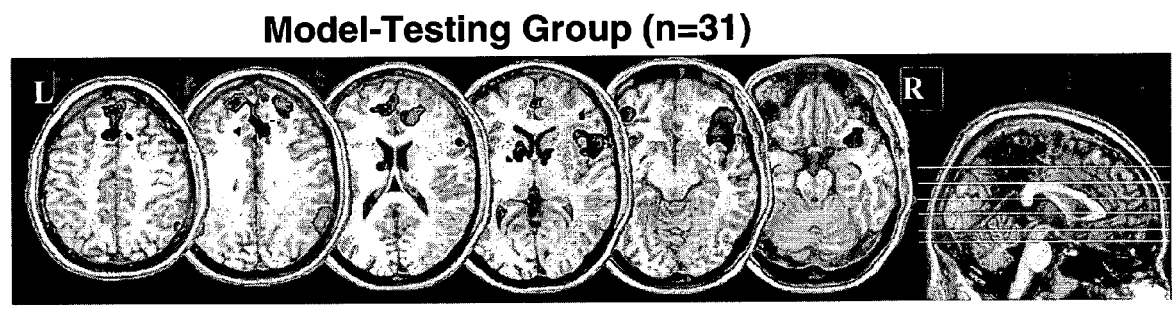

Figure 3
Accuracy of Lie Detection for Individual Subjects
Model-Building Group
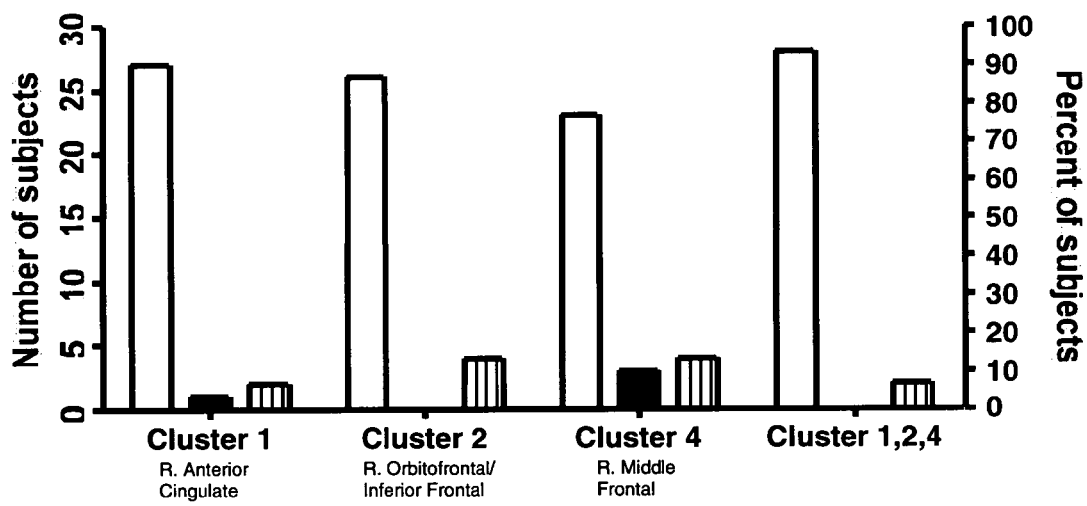
Model-Testing Group
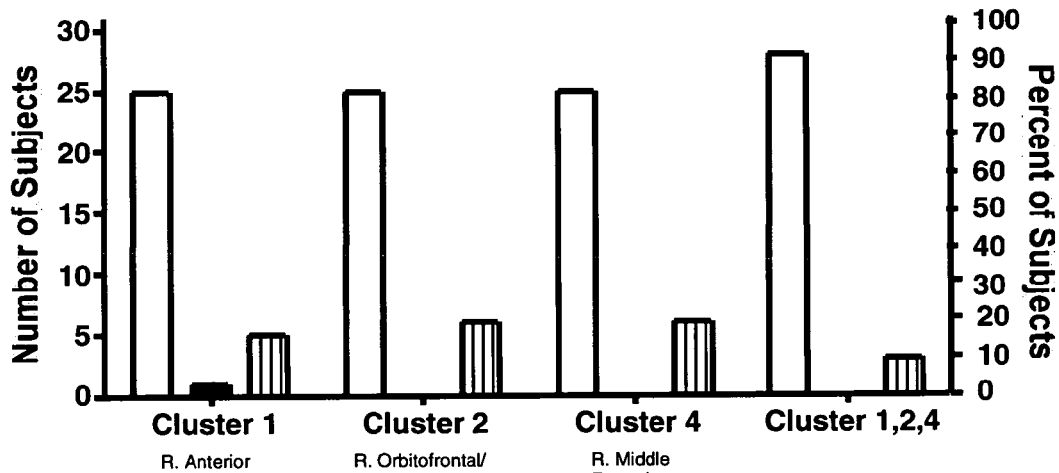
☐ Correct
■ Indeterminate
▥ Wrong Mean voxel activation by contrast

SYSTEMS AND METHODS FOR DETECTING DECEPTION BY MEASURING BRAIN ACTIVITY

RELATED APPLICATIONS

This application is a continuation-in-part of U.S. application Ser. No. 10/868,045, filed Jun. 14, 2004, which claims benefit of priority to International Application No. PCT/US02/40142, filed Dec. 13, 2002, U.S. Provisional Application No. 60/341,137, filed Dec. 13, 2001, U.S. Provisional Application No. 60/341,297, filed Dec. 13, 2001, and U.S. Provisional Application No. 60/396,054, filed Jul. 15, 2002.

This application claims priority to U.S. Provisional Application No. 60/605,870, filed Aug. 30, 2004.

BACKGROUND OF THE INVENTION

1. Field of the Invention

The invention relates to the detection of deception by measuring brain activity which is associated with acts of deception.

2. Description of the Related Art

Deception, the conscious and intentional misleading of another to accept as true or valid what is actually false or invalid, is an unfortunate, but common human practice with substantial societal costs. For example, according to U.S. government statistics for the years 1999-2002, civil litigation consumed approximately $100 billion annually in attorney fees as both individuals and corporations fought in the courts to resolve disputes that could, in many instances, be decided with reliable deception detection. Government expenditures and lost productivity add even more to the societal cost of civil litigation. Similarly, fraud is estimated to cost the insurance industry $80 billion annually, but reliable deception detection could both reduce insurance premiums and speed claim processing for legitimate claimants. In commerce, industrial espionage and the theft of trade secrets result in untold losses in proprietary confidential information which could be better protected by reliable employee screening. Finally, in the defense and intelligence communities, there is an enormous need to safeguard secret information and, therefore, a need for reliable detection of deception during security clearances and investigations.

The search for an accurate lie detector has a long and colorful history, ranging from the ancient Chinese practice of putting rice in the mouth of suspected liars to the quasi-scientific techniques of polygraph and voice stress analysis (see, e.g., Furedy (1986)). The development of equipment to measure psycho-physiologic functions enabled investigators in the late 19th century to study the peripheral physiologic changes that were associated with deception. This led to the development of more sophisticated peripheral measuring techniques and data analysis, including the polygraph (Yankee (1995)).

Polygraph devices examine differences in peripheral autonomic responses to relevant versus irrelevant questions. For example, current polygraph devices record changes in skin conductance response (SCR), blood pressure, respiration and peripheral vasomotor activity. Whenever a greater autonomic response is recorded after a relevant questions versus an irrelevant question, this data is interpreted as indicative that the subject is being deceptive (see, e.g., Furedy (1986)).

Polygraph devices have several significant limitations. For example, subjects can learn to control some autonomic responses and, thereby, circumvent the ability of the test to detect deception. Conversely, anxiety associated with the test or questions can lead to autonomic responses associated with deception irrespective of the truthfulness of the subject's answers. Polygraph interpretation and testing procedures are also subjective. For example, there is little consensus amongst polygraph examiners regarding the types of questions to ask, and the interpretation of the results can be highly subjective. More fundamentally, polygraph devices do not directly measure any mental activity associated with deception but, rather, measure non-specific peripheral changes in the arousal of the test subject. Not surprisingly, the substantive predictive value of the polygraph has been found to be poor in many screening and investigative situations, and scientific evidence regarding the polygraph's validity is significantly lacking.

Various other techniques have been investigated to predict deception, which also use peripheral measures of autonomic activity. These techniques include measures of papillary size response to visual stimuli that are related to a mock crime scene (Lubow and Fein (1996)), voice analysis, observations of facial and hand movement (Ekman et al. (1991)), observations of verbal cues (Sporer (1997)), hypnosis (Sheehan and Statham (1988)), and high-definition thermal imaging of periorbital changes (Pavlidis et al. (2002)). One of the few methods that actually measures brain activity involves examining the amplitude of the P300 component of event-related brain potentials (Farwell and Donchin (1991); see also U.S. Pat. Nos. 4,941,477, 5,363,858, 5,406,956, and 5,467,777).

More recently, brain imaging techniques have been used to investigate brain activity associated with various mental tasks non-invasively (see, e.g., Ogawa et al. (1990)). For example, Shastri et al. (2000) disclosed the simultaneous use of fMRI and SCR measurements, and noted the potential to reveal relationships between psychological states and patterns of brain activity. However, Shastri et al. did not attempt to measure deception. Rather, they investigated brain activity in response to an auditory stimulus consisting an aggravating clicking sound (10 Hz frequency). Critchley et al. (2000) also measured SCR during fMRI. In their experiments, fMRI was performed in the context of "sympathetic arousal" and "risk-taking behavior" in which subjects picked playing cards and won or lost money based on their choices. Again, however, Critchley et al. did not attempt to detect deception. Other researchers using fMRI and positron emission tomography (PET) have successfully delineated brain activity involved in response inhibition (e.g., "Go/No-Go" tasks) (Elliott et al. (2000), divided attention (Pardo et al. (1991); George et al. (1997); Bush et al. (1998)), anxiety (Rauch and Savage (1997); Lorberbaum et al. (1999)), emotion-related learning with reward and punishment (O'Doherty et al. (2001)), and cognitive breakthrough differentiating components of cognitive control such as performance monitoring (MacDonald et al. (2000)).

The present invention addresses the need for reliable detection of deception by specifically identifying the brain regions involved in deception in an individual, and measuring brain activity associated with potentially deceptive states or responses. By measuring brain activity as opposed to peripheral measures of autonomic or sympathetic responses, the present invention avoids the drawbacks of the prior art, and provides a reliable, objective means of detecting deception. Moreover, because the present invention measures brain activity which is inherent in and necessary to the process of deception, it provides a means of detecting deception which cannot be circumvented by trained, skillful or remorseless liars.

SUMMARY OF THE INVENTION

The present invention depends, in part, upon the identification in groups of individuals of those brain regions which are typically activated during deception, the recognition that there is variability amongst individuals in these regions, and the development of methods for detecting deception at the individual level despite that variability. In particular, the invention provides methods for detecting deception using appropriate controls which provide for reliability and reproducibility of results, and a level of confidence suitable for legal, commercial and security applications.

Thus, in one aspect, the invention provides methods for determining whether the brain activity of a human subject in response to a stimulus of interest is characteristic of a state of interest. In these methods, a stimulus of interest is provided to the subject and the brain activity of the subject in response to the stimulus is measured during a period of interest. The brain activity in at least one brain region when measured during the period of interest is compared with a predetermined control level of activity, and a determination is made whether the brain activity in the brain region(s) when measured during the period of interest is characteristic of the state of interest based upon the comparison. Alternatively, a comparison can be made to determine whether the activity is not characteristic of the state of interest (i.e., lacks characteristics of that state).

In some embodiments, the stimulus is selected from the group consisting of a sound, a picture, an aurally-presented question and a visually-presented question.

In some embodiments, the state of interest is either a truthful state or a deceptive state.

The invention is directed to a method for measuring brain activity of a subject by subjecting the subject to at least one first stimulus of interest, measuring brain activity of the subject during a first period of interest, and generating a first brain map for the subject; subjecting the subject to at least one second stimulus of interest, measuring brain activity of the subject during a second period of interest, and generating a second brain map for the subject; generating a first contrast brain map for the subject by subtracting a parameter of interest of the second brain map from the parameter of interest of the first brain map; generating a second contrast brain map for the subject by subtracting the parameter of interest of the first brain map from the parameter of interest of the second brain map; and determining if the subject responded to the first or the second stimulus of interest. In one embodiment, whether the subject responded to the first or second stimulus of interest can be determined as follows: if the parameter of interest of the first contrast map is greater than the parameter of interest of the second contrast map, then the subject is determined to have responded to the first stimulus of interest; or if the parameter of interest of the second contrast map is greater than the parameter of interest of the first contrast map, then the subject is determined to have responded to the second stimulus of interest. In one aspect, the at least one of the first and the second stimulus of interest comprises asking the subject to perform a task. The task can be a motor task or the taking a ring or a watch. In other embodiments, the at least one of the first and the second stimulus of interest is selected from the group consisting of a sound, a picture, an aurally-presented question and a visually-presented question. In some embodiments, the first and the second questions either truthfully and deceptively, or deceptively and truthfully. In some embodiments of the invention, the answer to the question is known. The parameter of interest can be a number of activated voxels, in some embodiments. In other embodiments, the parameter of interest is a t-value or a p-value. The contrast brain map is generated for at least one specific brain region, in certain embodiments.

In some embodiments, the step of comparing brain activity includes generating a first brain map of activity prior to or after the period of interest, generating a second brain map of activity during the period of interest, and generating a third brain map representing the difference between the first brain map and the second brain map. In these embodiments, the third brain map can include data representing values of statistical significance or probabilities.

In another aspect of the invention, the invention is directed to methods of asking a subject to respond to at least one stimuli, measuring brain activity of the subject during each of the one or more periods of interest, and generating a brain map for the subject for each of the one or more periods of interest; generating a baseline brain map for the subject for the a period of interest; generating one or more contrast brain maps for the subject by subtracting a parameter of interest for the baseline map from the parameter of interest for each of the brain maps in the first step; and determining if the subject responded to any of the stimuli of interest. Whether the subject responded to any of the stimulus of interest can be determined if the parameter of interest for a given contrast brain map is greater than the parameter of interest for the baseline brain map, then the subject is determined to have responded to the stimulus associated with that brain map; or if a parameter of interest for the a given contrast brain map is lesser than the parameter of interest for the baseline brain map, then the subject is determined not to have responded to the stimulus associated with that brain map. In another embodiment, generating the baseline brain map for the subject for a period interest can be done by averaging all of the one or more brain maps. Alternatively, generating the baseline brain map for the subject for a period of interest can be done by averaging the one or more brain maps other than the brain map for the period of interest. In some embodiments, the baseline brain map for the subject for a period interest is a brain map for a different period of interest. In another aspect, the at least one or more stimuli is selected from the group consisting of a sound, a picture, an aurally-presented question and a visually-presented question. The invention also covers methods wherein the at least one or more stimuli comprises answering a question truthfully and at least one of the stimuli comprises answering a question deceptively or wherein the answer to the question is known. In other embodiments, at least one of the stimuli comprises a motor task, which can further be the taking of a ring or a watch. In yet other embodiments, the contrast brain map is generated for at least one specific brain region.

In another aspect, the invention provides methods for determining whether the brain activity of a human subject during a response to a question of interest is characteristic of a truthful or a deceptive response. In these methods, the subject is asked at least one question of interest and is allowed to provide a response of interest during a period of interest while the brain activity of the subject is measured. It is not known beforehand whether the response of interest is truthful or deceptive. The brain activity in the brain region(s) measured during the period of interest is compared with a predetermined control level of activity, and a determination is made whether the brain activity in the brain region(s) when measured during the period of interest is characteristic of a truthful or a deceptive response based upon the comparison.

In a further aspect of the invention, a method for determining whether brain activity of a human subject during a response to a question of interest is characteristic of a truthful or a deceptive response is provided by asking the subject at least one question of interest, allowing the subject to provide a response of interest during a period of interest, wherein it is not known beforehand whether the response of interest is truthful or deceptive, and measuring brain activity of the subject during the period of interest; asking the subject at least once to admit and at least once to deny to the question of interest; generating a first contrast map by subtracting denial responses from admission responses; generating a second contrast map by subtracting admission responses from denial responses; generating a resulting contrast map by subtracting the second contrast map from the first contrast map; and determining whether the subject is admitting or denying to the question of interest. Whether the subject is admitting or denying the question of interest can be determined if the value of a parameter of interest for the resulting contrast map is positive, then the subject is determined to admitting to the question of interest; or if the value of a parameter of interest for the resulting contrast map is negative, then the subject is determined to denying to the question of interest; or if the value of a parameter of interest for the resulting contrast map is about zero, then the subject is determined to neither denying nor admitting to the question of interest. In other embodiments, the value of the parameter of interest is statistically significant. The parameter of interest can be a t-value or a p-value. The parameter of interest can also be a number of activated voxels, wherein the number of activated voxels is determined at p-values <0.05, at p-values <0.001, or at p-values <0.0005.

In some of the foregoing embodiments, the control level of activity can be a level which is characteristic of either a truthful response or a deceptive response by a group of individuals. In other embodiments, the control level of activity can be a level which is not characteristic of either a truthful response or a deceptive response by a group of individuals (i.e., lacks characteristics of a truthful or deceptive response). On yet other embodiments, the control level of activity can be a level which is characteristic of either a truthful response or a deceptive response to control questions by the subject. Finally, in yet other embodiments, the control level of activity can be a level which is not characteristic of either a truthful response or a deceptive response to control questions by the subject (i.e., lacks characteristics of a truthful or deceptive response).

In some of the foregoing embodiments, the step of comparing the brain activity can include scaling the brain activity in the brain region(s) relative to brain activity which is characteristic of a control response by the subject. In these embodiments, the control response can be a motor, auditory, visual, pain or other response.

In some embodiments involving questions of interest, the step of comparing brain activity can include generating a first brain map of activity prior to or after the period of interest, generating a second brain map of activity during said period of interest, and generating a third brain map representing the difference between said first brain map and said second brain map. In these embodiments, the third brain map can include data representing values of statistical significance or probabilities.

In another aspect, the invention employs control questions in methods for determining whether brain activity during a response of a human subject to a question of interest is characteristic of a truthful or a deceptive response. In these methods, the subject is asked at least one truthful control question and is allowed to provide a truthful response during a truthful control period while the brain activity of the subject is measured. In addition, the subject is asked at least one deceptive control question and is allowed to provide a deceptive response during a deceptive control period while the brain activity of the subject is measured. In addition, the subject is asked at least one question of interest and is allowed to provide a response of interest during a period of interest while the brain activity of the subject is measured. It is not known beforehand whether the response of interest is truthful or deceptive. Based upon these measurements, at least one brain region is identified which exhibits a statistically significant difference in brain activity when measured during the truthful control period and when measured during the deceptive control period. The brain activity in the brain region(s) when measured during the period of interest is compared with brain activity during at least one of the truthful control period and the deceptive control period, and a determination is made whether the brain activity in the brain region(s) when measured during the period of interest is (or is not) characteristic of a truthful or a deceptive response based upon the comparison.

The invention also provides a method for determining whether brain activity of a human subject in response to a stimulus of interest is characteristic of a state of interest by providing a stimulus of interest; asking a subject to admit to the stimulus of interest while measuring brain activity; asking the subject to deny to the stimulus of interest while measuring brain activity; generating brain maps for admission and denial states of interest; comparing brain maps for admission and denial states of interest; and determining whether the brain activity in the at least one brain region when measured during the period of interest is characteristic of the state of interest based upon the comparison. In some embodiments, the stimulus of interest comprises a motor task. In further embodiments, the motor task comprises taking a ring and a watch.

In another aspect, subjects are asked to admit to the question of interest and then deny the question of interest. The activity in the brain regions is measured during at least one admission periods and at leas tone denial period, followed by a determination whether the brain activity when measured during the question of interest is characteristic of a truthful or a deceptive response based upon the comparison.

In some embodiments, the step of comparing the brain activity includes generating a first brain map of activity during the period of interest, generating at least a second brain map of activity during the truthful control period(s) and the deceptive control period(s), and generating at least a third brain map representing the difference between the first brain map and the second brain map. In some of these embodiments, the third brain map can include data representing values of statistical significance or probabilities.

In some embodiments, the step of comparing the brain activity comprises measuring the brain activity during the subject's admission to the question of interest, measuring the brain activity during the subject's denial to the question of interest, and generating a brain map comparing these two states. The brain map may be used to determine if the subject did or did not perform the question of interest if the value of activation exceeds a threshold. In one embodiment, a subject is administered a control question wherein the control question shows activation of the brain region of interest relative to the control question of interest. In yet another embodiment, the activation of at least one brain region of interest is determined using a threshold value of brain region activation as determined by the groups of individuals.

In any of the foregoing embodiments, the brain activity of the subject can be measured by fMRI, BOLD fMRI, PET, SPECT, EEG, MEG, DOT or combinations thereof, as these terms are defined herein.

In any of the foregoing embodiments, the brain region(s) can be chosen from prefrontal cortex, limbic cortex, anterior cruciate, temporal cortex, parietal cortex, caudate, hypothalamus and cerebellum. In some embodiments, the brain regions can be chosen from orbitofrontal cortex, anterior cingulate cortex, prefrontal cortex, middle temporal cortex, insula, cuneus, post-central gyrus, pre-central gyrus, superior temporal gyrus and cerebellum. In certain embodiments, the brain region(s) can be chosen from the right anterior cingulate cortex, right inferior frontal cortex, right orbitofrontal cortex, left middle temporal cortex and right middle frontal cortex. In specific embodiments, the brain region(s) can be chosen from the right orbitofrontal cortex and right anterior cingulate cortex. In embodiments in which the subject has reversed left-right brain symmetry relative to the majority of the population, the terms "right" and "left" are reversed for the brain region(s).

In some embodiments, the brain region(s) can be chosen from a group of brain regions identified in a control group of individuals as exhibiting a statistically significant difference in brain activity when measured during truthful responses and when measured during deceptive responses. In these embodiments, the brain regions can include at least two brains regions chosen from orbitofrontal cortex, anterior cingulate cortex, prefrontal cortex, middle temporal cortex, insula, cuneus, post-central gyrus, pre-central gyrus, superior temporal gyrus and cerebellum. In embodiments in which the subject has reversed left-right brain symmetry relative to the majority of the population, the terms "right" and "left" are reversed for the brain region(s). In some of these embodiments, the control group of individuals is matched to the subject for at least one characteristic chosen from sex, age, medical/psychiatric condition, handedness, race, language skills, health, socioeconomic status, and MMPI profile.

In some embodiments, the methods include the step of assigning a probability that the subject is being deceptive. In other embodiments, the methods include the step of assigning a range of probabilities that the subject is being deceptive.

In yet other embodiments, the methods further include the steps of measuring a physiological indicator chosen from SCR, heart rate and blood pressure at least once during the period of interest, and determining whether the indicator measurement is characteristic of a truthful or a deceptive response.

Thus, in some embodiments, the invention provides methods further including the steps of measuring the SCR of the subject during at least a portion of the period of interest, comparing the SCR during the period of interest with a predetermined control SCR, and determining whether the SCR is characteristic of a truthful or a deceptive response based upon the comparison. In some of these embodiments, the measuring of the SCR includes the steps of attaching at least one SCR electrode to an area of the subject's skin, and maintaining substantially constant contact between the electrode and the subject's skin. In some embodiments, the methods include transmitting signals from the SCR electrode to a system processor via a shielded cable or employing a low-pass filter to reduce interference. In some of these embodiments, the SCR measurements can be stored on an electronic data storage medium.

In any of the foregoing embodiments, the step of measuring brain activity of the subject can occur multiple times during the period of interest, multiple times during the truthful control period, multiple times during the deceptive control period, at least once per second, at least once every two seconds, or at least once every three seconds.

In addition, in any of the foregoing embodiments, the brain activity of the subject can be measured by an MRI device using a field strength of at least 1 Tesla, at least 2 Tesla, or at least 3 Tesla.

In addition, in any of the foregoing embodiments, the methods can further include the step of storing the brain activity measurements on an electronic data storage medium.

In addition, in any of the foregoing embodiments, the subject's response can include pressing a button or raising a finger. In addition, the subject's response can correspond to an affirmative or negative response.

In addition, in any of the foregoing embodiments, the subject's response can be measured within 5 seconds of the question or stimulus.

Finally, in any of the foregoing embodiments, the question or stimulus can be aurally-presented or visually presented.

In another aspect, the invention provides systems for determining whether the brain activity of a human subject during a response to a question of interest is characteristic of a truthful or a deceptive response. The systems include means for providing a stimulus of interest, a brain activity measuring device, a response measuring device, and a system processor connected to the means for providing a stimulus, the brain activity measuring device and the response measuring device for receiving and processing data from each, and for statistically analyzing the data.

In some embodiments, the means for providing a stimulus comprises a screen which presents visual stimuli.

In some embodiments, the response measuring device includes at least one switch or button which is finger-activated by the subject.

In another aspect, the invention provides a system for determining whether the brain activity of a human subject during a response to a question of interest is characteristic of a truthful or a deceptive response which includes a brain activity measuring device, a SCR measuring device, a system processor connected to the brain activity measuring device and the SCR measuring device for receiving and processing data from each, and a shielded data cable for transmitting data from the SCR measuring device to the system processor.

In any of the foregoing embodiments, the brain activity measuring device can be chosen from an fMRI, BOLD fMRI, PET, SPECT, EEG, MEG and DOT device.

In another aspect, the invention provides a system for measuring the SCR of a human subject during magnetic resonance imaging which includes a magnetic resonance imaging device, a SCR measuring device, a system processor connected to the brain activity measuring device and the SCR measuring device for receiving and processing data from each, and a shielded data cable for transmitting data from the SCR measuring device to the system processor.

In any of the foregoing embodiments, the brain activity measuring device can measure brain activity in at least one brain region chosen from the right anterior cingulate cortex, right inferior frontal cortex, right orbitofrontal cortex, left middle temporal cortex and right middle frontal cortex.

In any of the foregoing embodiments including SCR measurements, the SCR measuring device can further include a device for maintaining substantially constant contact between an SCR electrode and an area of the subject's skin.

In any of the foregoing embodiments including SCR measurements, the system processor can be adapted to receive brain activity data from the brain activity measuring device and to receive SCR data from the SCR measuring device, and can be programmed to determine whether the brain activity of the subject during the response to the question of interest is characteristic of a truthful or a deceptive response.

In any of the foregoing embodiments including SCR measurements, the system processor can be adapted to receive brain activity data from the brain activity measuring device and to receive SCR data from the SCR measuring device, and to store the data on an electronic data storage medium.

In any of the foregoing embodiments including an SCR device and an MRI device, the system can further include a partition for a doorway of a shielded room containing the magnetic resonance imaging device. In these embodiments, the partition includes a panel of an electrically conductive material, having two sides and a periphery substantially corresponding in shape to the doorway, one or more electrically conductive contacts located at one or more portions of the periphery to provide an electrical contact between the panel and the doorway, a first electrical connector on a first side of the panel for connection to the shielded SCR cable, and a second electrical connector on a second side of the panel for connection to the system processor. In these embodiments, the first and second electrical connectors are coupled to each other such that data can be transmitted from the first side to the second side of said panel.

In any of the foregoing embodiments of the systems, the step of measuring brain activity of the subject can occur at least once per second, at least once every two seconds or at least once every three seconds.

In any of the foregoing embodiments of the systems, the brain activity of the subject can be measured by an MRI device using a field strength of at least 1 Tesla, at least 2 Tesla or at least 3 Tesla.

In another aspect, the invention provides a partition for the doorway of a shielded room containing a brain imaging device. The partition includes a panel of an electrically conductive material having two sides and a periphery substantially corresponding in shape to the doorway, one or more electrically conductive contacts located at one or more portions of the periphery to provide an electrical contact between the panel and the doorway, a first electrical connector on a first side of said panel, and the second electrical connector on a second side of the panel. In these embodiments, the first and second electrical connectors are coupled to each other such that data can be transmitted from the first side to the second side of the panel.

These and other aspects and embodiments of the invention will be apparent to one of ordinary skill in the art from the following detailed description of the invention and examples of certain embodiments.

BRIEF DESCRIPTION OF THE DRAWINGS

Tables 5-13 are described herein and provide results in the Example section.

Table 5 provides subject demographics and behavioural results.

Table 6 provides group an analysis of lie-minus-True Model-building group.

Table 7 provides a group analysis of Lie-minus-True model-Testing Group.

Table 8 provides subtraction technique of voxels.

Table 9 provides voxel subtraction method using Lie-True.

Table 10 shows threshold technique—voxels.

Table 11 shows mean and median values for the Lie-True, True-Lie, Lie-Neutral, True-Neutral contrasts.

Table 12 shows the significance of the different contrasts using values from Table 11.

Table 13 provides the voxel subtraction method using lie and true questions.

FIG. 1 is a pictoral representation of neural correlates of deception in a model-building group (top picture) and a model-testing group (bottom picture).

Group Analyses of Lie-minus-Truth for the Model-Building Group and the Model-Testing Group displaying the similar activation pattern for both groups. Areas of statistically significant (FDR $p<0.05$, $k=25$) activation in grey blobs are superimposed on the Montreal Neurologic Institute structural brain slices arranged from dorsal to ventral. The Clusters used for the individual analyses are indicated. The transverse slice locations ($z=46, 32, 18, 5, -10, -20$) are the same for both groups and are indicated on the Sagittal Image.

Figure 2:
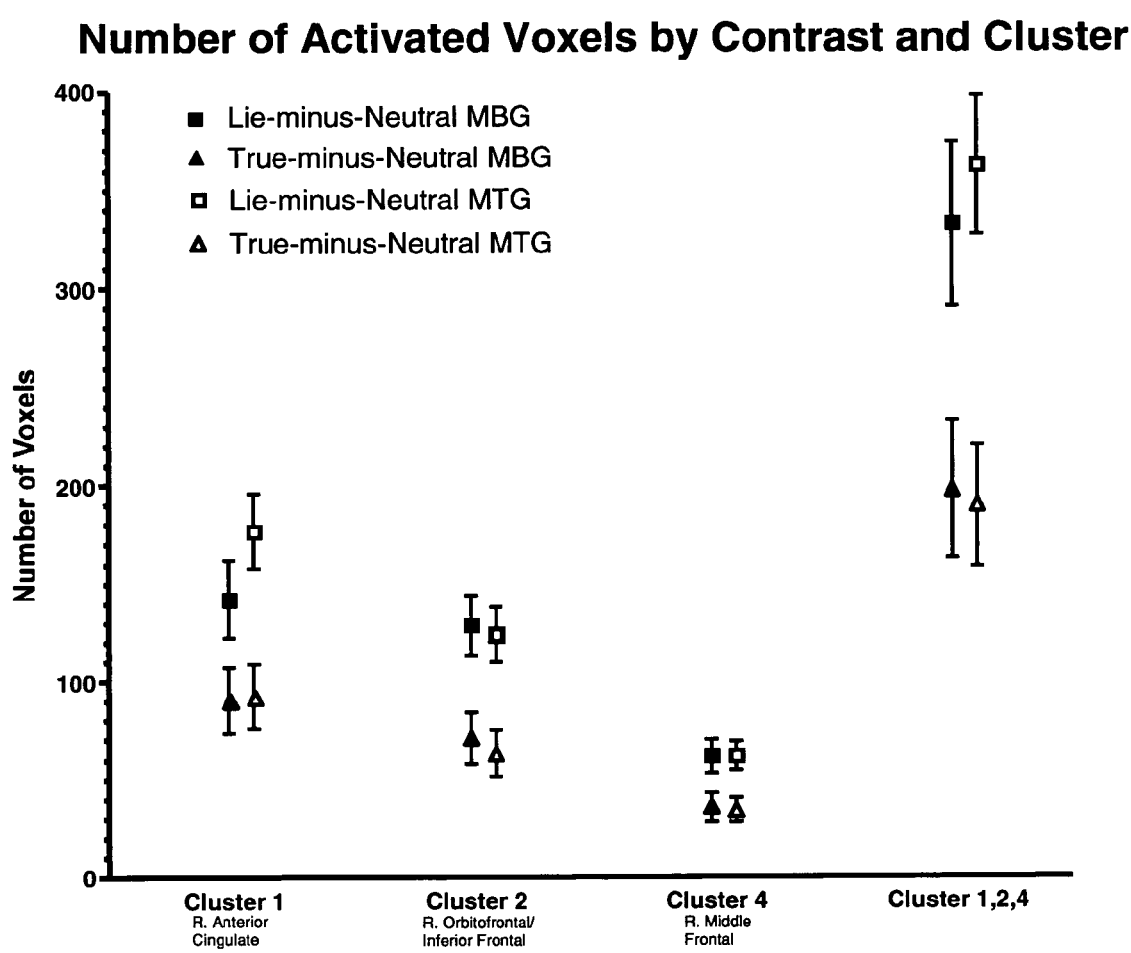

FIG. 2 is a graphic representation of the number of activated voxels by contrast and cluster.

FIG. 3 is a graphic representation of the accuracy of lie detection on individual subjects in a model-building group (top graph) and a model-testing group (bottom graph).

Figure 4:
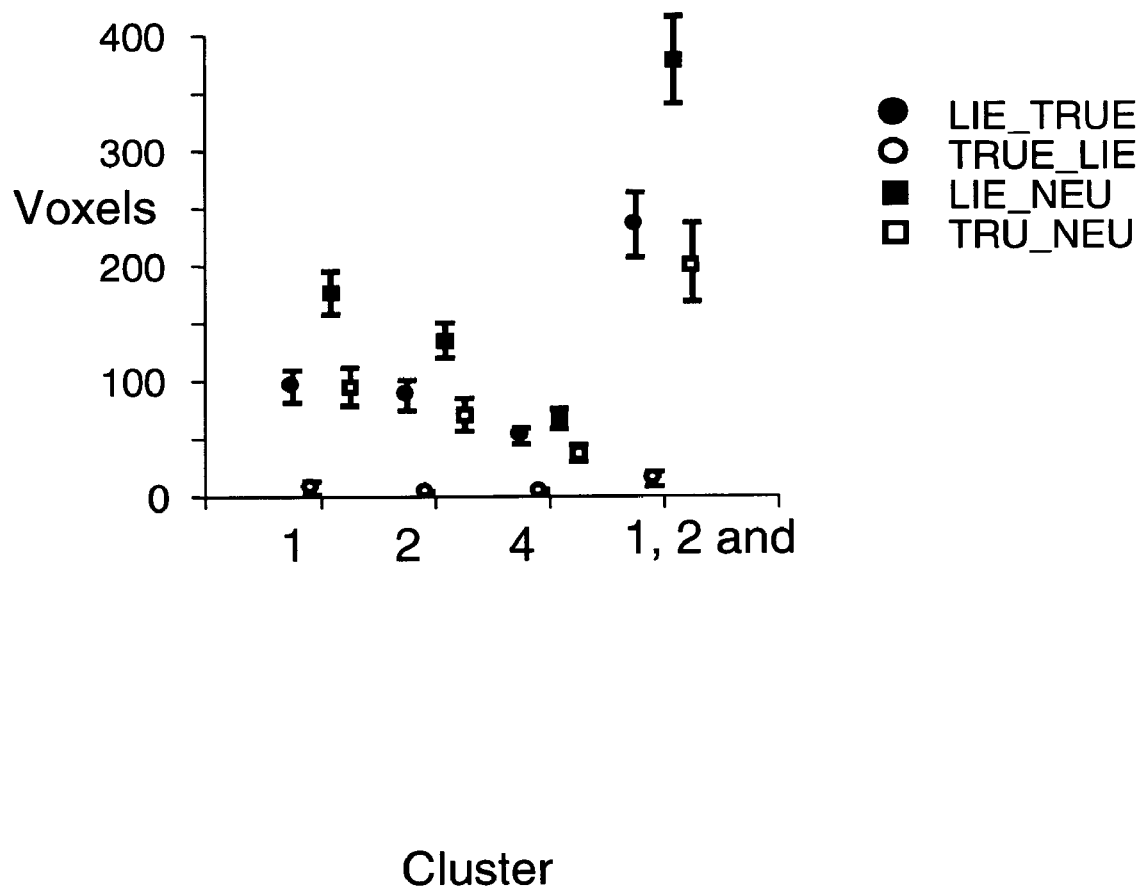

FIG. 4 is a graphic representation of the mean voxel activation by contrast.

DETAILED DESCRIPTION

The patent, scientific and medical publications referred to herein establish knowledge that was available to those of ordinary skill in the art at the time the invention was made. The entire disclosures of the issued U.S. patents, published and pending patent applications, and other references cited herein are hereby incorporated by reference.

Definitions

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent or later-developed techniques which would be apparent to one of skill in the art. In addition, in order to more clearly and concisely describe the subject matter which is the invention, the following definitions are provided for certain terms which are used in the specification and appended claims.

As used herein, the term "brain activity" means physiological and biochemical activity within the human brain, or a region of the brain, associated with mental activity, including but not limited to increases in blood flow to active brain regions, increases in metabolic activity (e.g., glucose consumption), changes in electrical potential of neurons, and the release of neurotransmitters. Brain activity may be measured non-invasively by, for example, measuring changes in electrical fields, magnetic fields or infra-red radiation emanating from the cranium.

As used herein, the term "brain region" refers to a volume of tissue within the human brain, which can be of any shape and which can be characterized anatomically or spatially.

As used herein, the term "Brodmann Area" and the abbreviation "BA" refer to the 47 regions of the cerebral cortex first described by Brodmann (1909) and are illustrated in FIGS. 9 and 10 of Talairach and Tournoux (1988).

As used herein, the terms "anterior", "posterior", "superior" and "inferior" have their customary meanings in anatomy. See, for example, Stedman's Medical Dictionary.

As used herein, the terms "frontal", "frontal lobe" and "frontal cortex" refer to that brain region as described in Martin (2003), and including all or part of BAs 4, 6, 8-12, 24, 25, 32, 33 and 44-47.

As used herein, the terms "orbitofrontal" and "orbitofrontal cortex" refer to that brain region as described in Martin (2003), including the basal surface of the frontal lobes, superior to the orbits of the eyes, and including all or part of BAs 10, 11, 38, 46 and 47.

As used herein, the terms "prefrontal" and "prefrontal cortex" refer to that brain region as described in Martin (2003), and including all or part of BAs 8-12, 24, 25, 32, 33 and 44-47.

As used herein, the terms "inferior frontal" and "inferior frontal cortex" refer to that brain region as described in Martin (2003), and including all or part of BAs 6, 38 and 44-47.

As used herein, the terms "middle frontal" and "middle frontal cortex" refer to that brain region as described in Martin (2003), and all or part of BAs 6, 8-11 and 44-47.

As used herein, the terms "parietal", "parietal lobe" and "parietal cortex" refer to that brain region as described in Martin (2003), and including all or part of BAs 1-3, 5, 7, 37 and 39-40.

As used herein, the terms "temporal", "temporal lobe" and "temporal cortex" refer to that brain region as described in Martin (2003), and including all or part of BAs 20-22, 34-38 and 40-42.

As used herein, the terms "middle temporal" and "middle temporal cortex" refer to that brain region as described in Martin (2003), and including all or part of BAs 20-22, 37, 39 and 48.

As used herein, the terms "superior temporal" and "superior temporal gyrus" refer to that brain region as described in Martin (2003), and including all or part of BAs 22, 38, 41, 42 and 48.

As used herein, the term "cerebellum" refers to that brain region as described in Martin (2003).

As used herein, the term "anterior cruciate" refers to that brain region as described in Martin (2003).

As used herein, the term "caudate" refers to that brain region as described in Martin (2003), particularly at pages 44-45, 77 and 328.

As used herein, the terms "cingulate", "cingulate cortex" and "cingulate gyrus" all refer to that brain region as described in Martin (2003), including all or part of BAs 6, 11, 23, 24 and 31-33 and, in the region of the retrosplenial isthmus, BAs 23, 26, 29 and 30.

As used herein, the term "cuneus" refers to that brain region as described in Martin (2003), and including all or part of BAs 7, 17-19 and 23.

As used herein, the term "hypothalamus" refers to that brain region as described in Martin (2003).

As used herein, the term "insula" refers to that brain region as described in Martin (2003), and including all or part of BAs 38, 47 and 48.

As used herein, the terms "limbic" and "limbic cortex" refer to that brain region as described in Martin (2003), particularly at page 378.

As used herein, the term "pre-central gyrus" refers to that brain region as described in Martin (2003), and including all or part of BAs 4 and 6.

As used herein, the term "post-central gyrus" refers to that brain region as described in Martin (2003), and including all or part of BAs 1, 2 and 3.

As used herein, the term "voxel" refers to a multidimensional data point corresponding to a specific volume in space, and particularly refers to such a data point obtained from a brain imaging procedure and corresponding to a specific volume within the brain.

As used herein, the term "brain map" means a set or array of data in which each data point corresponds to a point or volume in a human brain. Each data point can consist of a single datum associated with a brain coordinate, or can consist of a multidimensional data array associated with a brain coordinate. The brain map can be displayed as a two- or three-dimensional representation, or can be stored as a data set without being graphically displayed.

As used herein, the term "deception" means the act, with conscious intent, of causing another to accept as true or valid what is false or invalid. Similarly, as used herein, the term "deceptive" means intended to cause deception.

As used herein, the term "deceptive response" means any communication, action or omission in response to a question or other stimulus which is intended to be deceptive.

As used herein, the term "deceptive state" means a transient state of brain activity characteristic of a deceptive response or awareness of deception.

As used herein, the term "deceptive control question" means a control question which elicits a deceptive response which is known a priori to be deceptive.

As used herein, the term "deceptive control period" means a period of time during which a deceptive response to a deceptive control question is provided, beginning during or after the presentation of the deceptive control question and ending after a period sufficient to measure the response to the question.

As used herein, the term "truthful response" means any communication, action or omission in response to a question or other stimulus which is not intended to be deceptive. A truthful response may, in fact, be true or valid, or it may be false or invalid if there is no intent to be deceptive.

As used herein, the term "truthful state" means a transient state of brain activity characteristic of a truthful response or no awareness of deception.

As used herein, the term "truthful control question" means a control question which elicits a truthful response which is known a priori to be truthful.

As used herein, the term "truthful control period" means a period of time during which a truthful response to a truthful control question is provided, beginning during or after the presentation of the truthful control question and ending after a period sufficient to measure the response to the question.

As used herein, the term "question of interest" means a question to which elicits a response which is not known a priori to be deceptive or truthful, and for which it is of interest to determine whether the response is deceptive or truthful.

As used herein, the term "stimulus of interest" means a stimulus which elicits a response which is not known a priori to be deceptive or truthful, and for which it is of interest to determine whether the response is deceptive or truthful, or which elicits a state of interest, and for which it is of interest to determine whether the state is characteristic of a deceptive state or a truthful state.

As used herein, the term "response of interest" means a response to a question of interest or a stimulus of interest.

As used herein, the term "state of interest" means a transient state of brain activity elicited by a question of interest or a stimulus of interest.

As used herein, the term "period of interest" means a period of time during which either (1) a response of interest to a question of interest or a stimulus of interest is provided, beginning during or after the presentation of the question of interest or stimulus of interest and ending after a period sufficient to measure the response to the question or stimulus, or (2) a state of interest is elicited by the question of interest or stimulus of interest, beginning during or after the presentation of the question of interest or stimulus of interest and ending after a period sufficient to measure the response to the question or stimulus.

As used herein, the term "control question" means a question to which the true or valid answer is known a priori. The true or valid answer need not be known with absolute certainty but, rather, can be known to a sufficient degree of probability (e.g., beyond reasonable doubt) to be useful for the intended purpose.

As used herein, the term "control response" means a transient state of brain activity causally associated with a control activity or stimulus, such as a motor response (e.g., brain activity associated with raising a finger or pressing a button) or a response to a stimulus (e.g., brain activity associated with response to an auditory, visual, tactile or pain response).

As used herein, the term "comparing the brain activity" means evaluating the brain activity in a particular region or voxel during a particular period of time in relation to the brain activity in the same or different regions or voxels during the same or different period of time in order to identify similarities or differences which are characteristic of some state. Such a comparison can include a direct evaluation of raw data points corresponding to brain activity (e.g., magnetic or electrical fields, blood flow) or indirect evaluations based upon summary statistics. In addition, such a comparison can include an evaluation of raw data or summary statistics from an individual in relation to averaged data or summary statistics from the same individual or from a group of individuals, or in relation to some other control level of activity.

As used herein, the term "control level of activity" means any level of activity to which the brain activity of an individual in a particular region or voxel during a particular period is compared. The control level can be derived from the same individual or from a group of individuals, or can be based upon an arbitrary or statistical threshold designed to identify differences in brain activity which are of interest.

As used herein, the term "characteristic of", when used in connection with a specified response or state (e.g., deceptive, truthful), means statistically associated with the specified response/state to a degree which allows the specified response/state to be distinguished from other types of responses/states with a useful degree of certainty (e.g., $p<0.5$, $p<0.1$, $p<0.05$, etc.) or probability (e.g., >50%, >90%, >95%, etc.).

As used herein, the term "activate" means to cause an increase in activity.

As used herein the term "increase" means to cause a statistically significant increase.

As used herein, the term "statistically significant" means having a probability of less than 10% under the relevant null hypothesis (i.e., $p<0.1$).

As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values $\geq 0$ and $\leq 2$ if the variable is inherently continuous.

As used herein, unless specifically indicated otherwise, the word "or" is used in the inclusive sense of "and/or" and not the exclusive sense of "either/or."

Methods for Detecting Deception by Measuring Brain Activity.

The present invention is dependent, in part, upon the discovery that, despite significant variation in the anatomy and functional usage of different brain regions amongst human individuals, it is still possible to identify patterns of brain activity in certain brain regions within an individual that are characteristic of deception or a deceptive state. Thus, although the patterns of activity associated with deception can differ between individuals, or even within the same individual between different deceptive responses or different deceptive states, it is nonetheless possible to assess the likelihood that an individual is being deceptive based upon measurements of brain activity.

Thus, in some embodiments, the invention provides methods for determining whether the brain activity of a human subject in response to a stimulus of interest is characteristic of a particular state of interest, such as a deceptive state or a truthful state. The stimulus of interest can be essentially any stimulus which can be presented while measuring brain activity. For example, the stimulus of interest can be a question which can be presented aurally (e.g., spoken or from a recording) or visually (e.g., printed or displayed on a video screen). Alternatively, the stimulus of interest can be a sound (e.g., a particular individual's voice) or an image (e.g., a photograph of a crime scene, a drawing or photograph of a particular individual's face) which may elicit a response. A stimulus of interest also can be part of a series of stimuli which are presented after a question, such as the question "Do you recognize any of the following?" followed by a series of photographs of individuals, objects or places.

It is not necessary that the subject respond to the stimulus of interest by speech or physical movement. Rather, the stimulus of interest can elicit a response in brain activity even in the absence of any overt or manifest response. In some embodiments, however, the subject will respond overtly by speech (e.g., answering "yes" or "no") or by physical movement (e.g., raising a finger, pressing a button, blinking).

The brain activity is measured during a period of interest, which may include the period during which the stimulus of interest is presented, or may begin after presentation of the stimulus. Typically, the period of interest will extend for 1-20 seconds after the presentation of the stimulus, but can extend for arbitrarily short periods or arbitrarily long periods with the understanding that measurements for shorter periods may not capture all (or any) of the response in brain activity and that measurements for longer periods may or may not capture pre-response or post-response brain activity which can confound the interpretation of the results. The period of interest can be subdivided into a number of shorter periods, each corresponding to a single measurement of brain activity. Thus, there can be multiple measurements of brain activity during a period of interest, or only one.

In some embodiments, the stimulus of interest is a question to which the subject provides a response of interest. In some embodiments, the subject may be instructed to provide both truthful and deceptive responses to the question of interest. Thus, in some embodiments, the invention provides methods for determining whether the brain activity of a human subject during a response to a question of interest is characteristic of a truthful or a deceptive response. In such methods, the subject is asked at least one question of interest and is allowed to provide a response of interest during a period of interest. Brain activity is measured during the period of interest, and the brain activity in at least one brain region is compared with a control level of activity to determine whether the brain activity in response to the question of interest is characteristic of a truthful or a deceptive response based upon said comparison.

In some embodiments, the step of comparing the brain activity during the period of interest includes a comparison of brain maps (as described below). In particular, a first brain map can be generated corresponding to the level of activity during the period of interest. A second brain map can be generated corresponding to the level of activity before or after the period of interest or corresponding to some other control level of activity. A third brain map can be generated corresponding to the difference between the first brain map and the second brain map. This third brain map can include differences in raw activity data, or can include data representing values of statistical significance or probabilities (e.g., z-scores or p-values as described below). A large variety of such maps can be generated by manipulating and mapping the raw data, and by adding, subtracting or otherwise manipulating other brain maps.

In other embodiments, the invention provides methods which employ truthful and deceptive control questions. In these methods, the subject is asked at least one truthful control question to which a truthful response is provided, and the brain activity of the subject is measured during the truthful control period in which the subject responds. In addition, the subject is asked at least one deceptive control question to which a deceptive response is provided, and the brain activity of the subject is measured during the deceptive control period in which the subject responds. The order of the truthful control question(s) and deceptive control question(s) can be arbitrary and, in some embodiments, truthful control questions and deceptive control questions are purposefully alternated or randomly mixed. The subject is also asked at least one question of interest to which a response of interest is provided, and the brain activity of the subject is measured during the period of interest in which the subject responds. Based upon these brain activity measurements, at least one brain region is identified which exhibits a statistically significant difference in activity in the subject during the truthful control period(s) when compared to the deceptive control period(s). (If no statistically significant difference can be identified, the sample size of measurements can be increased.) Next, the brain activity in the identified brain region(s) when measured during the period of interest is compared with the brain activity during the truthful control period(s) or deceptive control period(s) to determine whether the brain activity in the identified brain region(s) during the period of interest is characteristic of a truthful or a deceptive response.

As described above, in some embodiments, the step of comparing the brain activity during the period of interest includes a comparison of brain maps. In particular, a first brain map can be generated corresponding to the level of activity during the period of interest. A second brain map can be generated corresponding to the level of activity during a truthful control period, a deceptive control period or some other control level of activity. A third brain map can be generated corresponding to the difference between the first brain map and the second brain map (e.g., question of interest minus truthful control, question of interest minus deceptive control). This third brain map can include differences in raw activity data, or can include data representing values of statistical significance or probabilities (e.g., z-scores or p-values as described below). A large variety of such maps can be generated by manipulating and mapping the raw data, and by adding, subtracting or otherwise manipulating other brain maps.

In other embodiments, the invention provides methods which employ both truthful and deceptive answers to questions of interest. In an exemplary method, the subject is asked to answer the question of interest at least once truthfully and the brain activity of the subject is measured during the truthful period in which the subject responds. In addition, the subject is asked at answer the same question of interest at least once deceptively, and the brain activity of the subject is measured during the deceptive period in which the subject responds. The order of the truthful control questions and deceptive control questions can be arbitrary and, in some embodiments, truthful control questions and deceptive control questions are purposefully alternated or randomly mixed. Based upon these brain activity measurements, at least one brain region is identified which exhibits a statistically significant difference in activity in the subject during the truthful periods when compared to the deceptive periods. (If no statistically significant difference can be identified, the sample size of measurements can be increased or there is no conclusive answer provided.) Next, the brain activity in the identified brain regions when measured during the question of interest is directly compared with the brain activity during the truthful periods or the deceptive control periods to determine whether the brain activity in the identified brain regions during the question of interest is characteristic of a truthful or a deceptive response.

As described above, in some embodiments, the step of comparing the brain activity during the period of interest comprises a comparison of brain maps. In particular, a brain map can be generated corresponding to the level of activity during the truth and denial periods for one or more questions of interest. The number of activated voxels, significance levels, or t-values may be subtracted from one another. As one of the two states must be true, a positive value of the truth minus denial state would indicate lying on the truth state, a negative value of the truth minus denial state would indicate lying on the denial state, and equal values of the truth and denial states would not be interpreted.

In some of the foregoing methods, the step of comparing the brain activity during the period of interest comprises a comparison of brain maps. In particular, a first brain map can be generated corresponding to the level of activity during admission to the question of interest minus some truthful control period of interest. A second brain map can be generated corresponding to the level of activity during denial to the question of interest minus some truthful control period of interest. A determination of likelihood to show deception on another question of interest or the ability to determine deception may be made by directly comparing these two brain maps (e.g., significantly activated voxels in the truthful-minus-control period of interest minus the deception-minus-control period of interest). A comparison of these two states may be made by comparing the raw activity data, or can comprise data representing values of statistical significance or probabilities (e.g., z-scores or p-values as described below). A large variety of such maps can be generated by manipulating and mapping the raw data, and by adding, subtracting or otherwise manipulating activations of these two states.

In some of the foregoing methods, contrast maps are generated from two different states during a functional magnetic resonance imaging scan. These states may be opposite tasks, no task and task, or at least two different tasks. Comparisons made between the two can be determined by the user setting a significance threshold. Outputs generated are well known in the art and, may be selected from the number of significant voxels activated, t-values, F-values, variances, percent signal change, or any other quantity.

In some of the foregoing methods, the measurements of brain activity can be focused upon or limited to one or more brain regions identified in a control group of individuals as exhibiting a statistically significant difference in brain activity when measured during truthful responses and when measured during deceptive responses. Alternatively, the activity of the entire brain can be measured, but the statistical analysis of differences in activity can be limited to such regions. By limiting the brain regions measured or analyzed in this way, it is possible that better measurements can be obtained by focusing on fewer regions, and that more robust statistical analyses can be conducted be excluding regions unrelated to the brain activity involved in deception (e.g., motor regions involved in physical aspects of responses).

Measurements of Brain Activity.

Any of a number of devices known in the art can be used to measure brain activity in the methods of the invention. Such devices include, without limitation, magnetic resonance imaging (MRI), positron emission tomography (PET), single photon emission computed tomography (SPECT), quantitative electroencephalogram (qEEG), magneto-encephalography (MEG), and diffuse optical tomography (DOT) devices. In addition, it is expected that new devices will be developed in the future to measure brain activity, and that some of these will be useful in the methods and systems of the invention.

Each of these devices is, to varying degrees, capable of generating data which can be assembled into a volumetric (i.e., three dimensional) image or map of the brain using appropriate computer software. Moreover, by taking multiple measurements over a period of time, it is possible to detect changes in brain activity associated with particular mental activities or functions and, thereby, to map the brain activity associated with such mental activities or functions to specific regions of the brain. The resultant "functional maps" of the brain correlate brain regions with mental activities or functions by measuring changes in activity associated with the performance of the mental activities or functions. In the context of the present invention, functional brain mapping is employed to map the brain regions correlated with deception or deceptive states in an individual.

MRI, which involves the detection of selective absorption of very high frequency radio waves by certain atomic nuclei that are subjected to a strong magnetic field, has been developed extensively as a method for imaging not only the brain, but all parts of the human anatomy. MRI provides very high-resolution volumetric images and does not require the ingestion of radioactive substances. Current MRI scanners are capable of imaging or mapping the entire brain in less than one second to many seconds depending on the parameters chosen, which allows for repeated scans over a relatively short period. Very rapid scans, however, generally provide a lower degree of resolution and, therefore, brain scans of 1-5 seconds are more common.

As opposed to conventional MRI, which provides a static image of tissues, functional MRI (fMRI) images the functioning of the brain over time. For example, blood oxygen-level dependent (BOLD) fMRI exploits the different magnetic signals generated by oxyhemoglobin and deoxyhemoglobin to identify areas of the brain with high oxygen demand, indicating increased activity. By generating a number of images in quick succession, changes in activity in response to a given mental task can be detected, thereby demonstrating the correspondence between the task and the brain region(s) involved in the task. BOLD fMRI is now routinely used to measure regional cerebral blood flow (rCBF) in response to changes in neuronal activity. Exemplary references on the use of BOLD fMRI include Feng et al. (2004) and Ogawa et al. (1990).

Various types of MRI devices can be employed in the methods of the invention, and a number of parameters relating to an MRI scan can be varied. For example, MRI devices generating magnetic fields varying from 0.5 to 7.0 Tesla (T) are commercially available, although magnetic fields of 1.5-4.0 T are more commonly used for fMRI. MRI devices with stronger magnetic fields are generally more sensitive and can, therefore, provide higher resolution images. MRI images of the brain are typically acquired in a series of 10-40 co-planar slices, in which each slice is 1-8 mm in thickness, but these values can vary depending on the area of interest and the specific question being addressed. An entire image of the brain is typically obtained in 1-5 seconds, but certain situations can require shorter or longer duration to acquire a complete picture of the brain (see, e.g., Tzourio-Mazoyer et al. (2002)).

Because of the strong magnetic fields generated by MRI devices, subjects with metal implants (other than dental fillings), shrapnel, or irremovable medical devices (e.g., pacemakers, fixed hearing aids) should not be examined in an MRI device.

Optionally, the resolution of an MRI can be improved by employing a sensitivity encoding phased-array head coil (e.g., SENSE™ Head Coil, Philips Electronics, N.V., Amsterdam, Netherlands).

Both PET, which involves the detection of positrons emitted by radioactive substances (e.g., $^{18}$F-fluorodeoxyglucose or FDG), and SPECT, which involves the detection of gamma rays emitted by radioactive substances (e.g., $^{123}$I-isopropyliodo-amphetamine or IMP), provide accurate images of the brain and also can be used in the methods of the invention. Each of these methods, however, typically involves the use of radioactive substances with short half-lives (e.g., approximately 102 minutes for FDG, approximately 13 hours for IMP) and, therefore, are not available for use at sites distant from the cyclotrons which are necessary to produce such isotopes. Both methods are well known in the art, and exemplary references regarding the use of PET and SPECT include Taylor et al. (1997), Wicker et al. (1998), and Turner et al. (2003).

Both qEEG, which measures the electrical fields associated with brain activity, and MEG, which measures the magnetic fields associated with brain activity, are based upon measurements which have historically provided only crude or spatially unrefined images of the brain. Improvements in these technologies, however, have increased the ability to functionally map brain activity to regions. For example, the development of superconducting quantum interference devices (SQUIDs) has improved the spatial resolution of MEG. Exemplary references regarding the use of qEEG and MEG include Alary et al. (2002), Babiloni et al. (2004), Moule et al. (2003).

DOT, also known as near infra-red (NIR) spectroscopy, produces images based upon the absorption and scattering of near-infrared light, and is useful for volumetric brain imaging based upon hemodynamic response. This method, however, is also limited in its ability to achieve high spatial resolution. Exemplary references regarding the use of DOT include Taga et al. (2003), and Noguchi et al. (2003).

In the discussion and examples which follow, reference is made primarily to the best-developed brain imaging technology, BOLD fMRI. One of skill in the art will recognize, however, that any of the above-described technologies, or any other technology capable of functional brain mapping, can be used equivalently in the methods of the invention.

Question and Response Formats.

In order to limit the brain regions involved in a response, to isolate activity which is not involved in deception, as well as to reduce variability between individuals, questions can be chosen such that the number of possible responses is limited. For example, questions with "yes" or "no" answers, or multiple-choice questions, can be used. Such questions avoid the mental activity associated with formulating more complicated verbal or written responses.

In addition, it may be possible to isolate the brain activity which, independent of the content of the question or the answer, and independent of the truthfulness of deceptiveness of the response, is inherently associated with the act of responding "yes" or "no" or choosing amongst multiple choices. For example, both truthful and deceptive "yes" responses require brain activity associated with speaking or otherwise indicating the "yes" response. By identifying that activity, it can be excluded from consideration when determining whether brain activity in response to a question of interest is characteristic of a truthful response or a deceptive response.

Questions may be asked by any means which are effective to communicate with the subject. For example, and without limitation, an investigator can ask questions orally, an audio recording of questions can be played, questions can be presented on printed materials, or questions can be presented on a video screen. In addition, as noted above, a general question (e.g., "Do you recognize the person in any of the following pictures?") or general instruction (e.g., "Press the button if you recognize the object in any of the following pictures") can be asked followed by a series of stimuli to which the question or instruction is applied.

In some embodiments, the nature of the brain activity measuring device may favor one format or another for asking questions. For example, in an MRI device, the subject's head is enclosed within the device and the device generates significant levels of noise. Therefore, for embodiments employing MRI devices, it may be preferred to ask questions visually using, for example, video goggles or a video screen, or to present questions aurally using, for example, ear plugs or head phones.

Depending upon the nature of the brain measuring device employed, it may be desirable to avoid spoken responses because the movements of the head inherent in speaking may interfere with the measurement of brain activity. For example, speaking can create motion artifacts which confound the interpretation of fMRI results. Therefore, in some embodiments, responses are communicated without speech, such as by moving a body part (e.g., finger, hand, foot), pressing a button, or moving a switch, joystick or computer mouse.

In some embodiments, an integrated computer-based system can be used to ask questions and record responses. For example, a computer processor can control the display of questions at timed intervals on a video screen or video goggles, and responses can be recorded by pressing buttons on a unit connected to the processor. The processor also can receive data from the MRI to integrate the brain activity with the questions and responses. At least one such system is available commercially (IFIS-SA™, MRI Devices Corp., Gainesville, Fla.).

Control Activities and Control Questions.

In order to determine whether the brain activity of a subject in response to a stimulus of interest or question of interest is characteristic of a deceptive state or a deceptive response, a statistical comparison is made to a control level of activity. As noted above, the control level of activity can be based upon measurements from the same individual or from a group of individuals, or can be based upon an arbitrary or statistical threshold designed to identify differences in brain activity which are of interest. In addition, the control level of activity can be based upon measurements of responses to control questions which are designed to elicit truthful and deceptive responses or states.

Thus, in some embodiments, the control level of activity is based upon measurements of brain activity in response to one or more control stimuli. For example, a subject can be shown a series of images including photographs of individuals who are not known to the subject (i.e., strangers), as well as one or more photographs of individuals who are known to the subject (e.g., recent acquaintances, long-time acquaintances, famous individuals, family members, alleged accomplices). The responses to these images can be analyzed to determine those aspects of brain activity that are associated with recognition of individuals, and to distinguish from those aspects related to the recognition of a human face. Similarly, images of objects (e.g., crime scene objects, weapons, stolen items, documents) or sounds (e.g., recorded voices, music) could be used as stimuli. Furthermore, as noted above, the stimuli can be presented after a question such that they are considered in the context of the question.

In such embodiments, a first control level of activity can be determined by measuring the response of the subject to the unfamiliar images (e.g., strangers) and a second control level of activity can be determined by measuring the response of the subject to the familiar images (e.g., family members). The response of the subject to a stimulus of interest (e.g., an alleged accomplice) can be compared to the first and second control levels of activity to determine whether the subject's response of interest is more characteristic of recognition or not. Such comparisons can be used to assess the likelihood that the subject is being truthful or deceptive when asked about the stimulus of interest.

In some embodiments, the control level of activity will be determined based upon measurements in a group of individuals. In such embodiments, the individuals within the group can be presented with identical stimuli or questions or with comparable stimuli or questions (e.g., photographs of family members would vary from individual to individual but would be comparable).

To reduce variability between individuals within the control group and the subject, the individuals within the group can be matched to each other and to the subject based on various criteria. For example, individuals can be matched for age (e.g., ±5 years, ±10 years), sex, race, ethnicity, handedness (e.g., using the Annett Handedness Scale (Annett (1970)), Edinburgh Handedness Inventory (Oldfield (1971)) or Waterloo Handedness Questionnaire (Steenhuis and Bryden (1989))), language skills (e.g., native language), health, socioeconomic status (e.g., MacArthur Subjective Status Scale (Adler et al. (2000))), and personality profile (e.g., Minnesota Multiphasic Personality Inventory (MMPI) (Graham (1999))). The degree of matching is entirely within the discretion of the practitioner. Based upon a variety of reports in the field of brain imaging, however, it is generally believed that matching for sex, age, medical/psychiatric condition and handedness is most significant.

In addition, or alternatively, to reduce variability within individuals with the control group and the subject, the results for each individual can be scaled to account for differences in baseline activities and variances in activity. For example, the average activity level over one or more brain regions (or the entire brain) can be scaled to an arbitrary value (e.g., such that the mean=100), and the variance in activity can be similarly scaled (e.g., such that the standard deviation=10). Alternatively, the brain activity associated with a control response (e.g., brain activity associated with raising a finger or pressing a button, or with response to an auditory, visual, tactile or pain response) can be used as a scaling factor within each individual, with all other brain activity scaled relative to the control response (e.g., the motor response brain activity=100). Motor responses are particularly useful scaling factors because they are less affected by subjective mental states and anatomical variation between individuals, but auditory, tactile and pain responses can also be used.

In some embodiments, the control level of activity is based upon measurements of brain activity in response to one or more control questions. The control questions can be truthful control questions, deceptive control questions, or a mixture thereof.

For the truthful control questions, the subject can be instructed to answer truthfully, or can spontaneously answer truthfully. Similarly, for deceptive control questions, the subject can either be instructed to answer deceptively or can spontaneously practice deception. In either case, the investigator knows (either with absolute certainty or an appropriate degree of certainty) whether the subject has provided a truthful answer or a deceptive answer. That is, in some instances, the answer will be known with certainty because it relates to an established fact (e.g., "Is today Monday?"), whereas in some cases the answer can be known with a sufficient degree of certainty (e.g., "Have you ever made a mistake?" "Have you ever told a lie?"). In certain cases, it is possible that the answer is not known at the time that the question is asked, but is later determined. For example, a subject cam deny familiarity with a person or object during a brain imaging procedure, but it can be demonstrated later by other evidence that the subject was, in fact, being deceptive. Thus, a question with an initially unknown answer (e.g., a question of interest) can subsequently be regarded as a control question (e.g., a deceptive control question) when the answer becomes known.

The control questions can be chosen to be emotionally neutral or emotive. Emotionally neutral questions are intended to be "matter-of-fact" and not to elicit brain activity associated with strong memories or emotions. Conversely, emotive questions are intended to be "uncomfortable" and to elicit an emotional response. Differences in brain activity between truthful responses to neutral and emotive questions, as well as differences between deceptive responses to neutral and emotive responses, represent differences which are based on the emotional content of the question or response, and not on the truthfulness or deceptiveness of the response. Therefore, brain regions which are characteristic of the emotive aspect of a question or response can be identified and eliminated from consideration when determining whether a subject's response to a question of interest is characteristic of a truthful or a deceptive response.

For example, neutral control questions can include:
Is your name John?
Are you over 18 years old?
Are you a United States citizen?
Do you own a dog?
Are you awake?
Is it raining?
Is today Monday?
Is 2+2 equal to 4?
Emotive control questions can include, for example:
Have you ever used foul language?
Have you ever used illegal drugs?
Have you ever cheated on a test?
Have you ever faked an illness?
Have you ever lied to hurt someone?
Have you ever lied to protect yourself?
Have you ever cheated on your taxes?
Have you ever stolen something?

In some embodiments, control questions are asked first in the positive and then in the negative. For example, the subject can be asked "Is your name John?" and "Is your name not John?" Alternatively, mutually exclusive questions can be asked. For example, the subject can be asked "Is your name John?" and "Is your name Robert?" Assuming that the subject provides a truthful or a deceptive response to both questions, the answer to one question will be "yes" and the answer to the other question will be "no." This procedure is useful to obtain measurements of brain activity while the subject provides both truthful and deceptive "yes" and "no" responses.

In some embodiments, a situation can be created by the investigator to create a basis for truthful and deceptive control questions. For example, as described in the examples below, a subject can be asked to perform a task (e.g., taking an object from a room, hiding an object in a room, choosing a playing card from a deck of cards, viewing pictures of strangers) and can then be asked questions about the task (e.g., "Did you take this object?" "Did you hide the object here?" "Did you choose this card?" "Have you seen this person before?"). In some embodiments, the subject is instructed to provide truthful responses to at least one set of questions and to provide deceptive responses to at least one other set of questions. Because the task is controlled by the investigator, the truthfulness or deceptiveness of all responses is known with certainty. In addition, because the task is simple, unambiguous, of recent occurrence, and presumably has no connection or relation to the individual's personal history or experiences, there is expected to be less variability in the responses between individuals.

In some situations, subjects may be asked to answer both truthfully and deceptively to one or more questions of interest during a single scanning session. In other situations, subjects may be asked to lie sometimes and tell the truth sometimes in response to the same question, but the administrator of the test does not instruct, nor does he know when the subject lies.

In any of the foregoing embodiments in which the subject is asked questions of interest, truthful control questions, or deceptive control questions, it is understood that the questions may be "asked" aurally visually, or in any other appropriate manner.

Brain Regions Implicated in Deception.

A number of different brain regions have been identified which are implicated in deception in different individuals. Although no one region has been identified which is activated in all individuals during deception, the present invention provides methods for identifying the brain region(s) which are activated during deception in a particular subject by comparing the brain activity in response to a stimulus or question of interest to control levels of activity, which can be based upon measurements obtained from the same individual or from a group of individuals, or by comparing the brain activity in response to a stimulus or question of interest to the activity measured in the subject in response to truthful and deceptive control questions.

Brain regions are generally defined either anatomically or by reference to a three-dimensional coordinate system. In either case, individual variation between brains, both structurally and functionally, limits the precision of such descriptions. Therefore, as used herein, references to particular brain regions refer to regions of typical or average brains, with the understanding that the precise locations in different individual will be variable. For example, Thompson et al. (1996)) estimate that individual differences remain in the 9-18 mm range even after normalization.

Anatomically, brain regions may be defined at various levels of generality or specificity. For example, at the grossest anatomical level, the brain consists of the hindbrain, midbrain and forebrain. At a finer anatomical level, the forebrain consists of the cerebral cortex, amygdala, corpus striatum, thalamus and hypothalamus. At a yet finer level, the cerebral cortex can be divided into lobes (i.e., frontal, parietal, temporal, and occipital). In addition, portions of defined anatomical structures can be further delimited by reference to their relative positions, such as anterior, posterior, superior, inferior, etc., or by reference to other structures.

In addition to such anatomical descriptions, forty-seven regions of the cortex were described by Brodmann (1909). These Brodmann Areas (BAs) are illustrated in FIGS. 9 and 10 of Talairach and Toumoux (1988). It should be noted, however, that the boundaries of many of the BAs do not coincide with the boundaries of the anatomical subdivisions. Therefore, a single BA may be correspond to portions of several anatomical subdivisions and, conversely, an anatomical subdivision may include all or a portion of several BAs.

It is well-known that the right and left sides of the brain are differentiated functionally. Although approximately 11-13% of the general population is left-handed, only about 5% of left-handed individuals show a left-right reversal in brain functionality. Therefore, as used herein, the descriptions of brain regions refer to right and left sides based on the more common "right-handed" brain, with the understanding that the "right" and "left" descriptors should be reversed in individuals in which the functionality is reversed.

Based upon the studies described herein, and subject to the variability described above, the brain regions which are activated during deception can include the prefrontal cortex, limbic cortex, anterior cruciate, temporal cortex, parietal cortex, caudate, hypothalamus and cerebellum. At a finer anatomical level, the brain regions can include the orbitofrontal cortex, anterior cingulate cortex, prefrontal cortex, middle temporal cortex, insula, cuneus, post-central gyrus, pre-central gyrus, superior temporal gyrus and cerebellum. In particular, regions which most consistently are activated include the right anterior cingulate cortex, right inferior frontal cortex, right orbitofrontal cortex, left middle temporal cortex and right middle frontal cortex.

Specific locations within the brain, or volumes within the brain, can also be described by reference to three-dimensional coordinate systems. One such system was described by Talairach and Toumox (1988), and is based upon a single brain considered by the authors to be typical. Another such system, developed at the Montreal Neurological Institute (MNI), was described by Collins et al. (1994), and is based upon an average of 152 brains. The MNI has also produced a high resolution single-subject brain template (Collins et al. (1998)). The brain images or maps of individual subjects can be compared to such template brains by visual comparison, or computer software programs can be used which map the individual brains onto a template brain. For example, the Statistical Parametric Mapping (SPM) software, described below, automatically performs spatial registration and normalization of individual brains onto the MNI template. Software is also available which determines the correspondence amongst MNI coordinates, Talairach coordinates and Brodmann Areas (e.g., MRIcro, available at www.cla.sc.edu/psyc/faculty/rorden/mricro.html; see also Rorden and Brett (2000), *Behavioural Neurology*, 12:191-200).

Statistical Analysis.

Methods for the statistical analysis of changes in brain activity are well known in the art and, for some brain activity measuring devices, computer software packages are commercially available which specifically adapted to analyze the data. For example, SPECT, PET or MRI data can be analyzed using the Dot or EMMA (Extensible MATLAB Medical image Analysis) packages which are both freely available from the MNI, or the SPM software package which is freely available from the Functional Imaging Laboratory of the Wellcome Department of Imaging Neuroscience at the University College of London, UK (www.fil.ion.ucl.ac.uk/spm/). The EMMA and SPM software are based upon the MATLAB® programming language (MathWorks, Inc., Natick, Mass.), with additional routines in the C programming language. An SPM module is incorporated into the commercially available MEDx software (Medical Numerics, Inc., Sterling, Va.). Other appropriate measuring devices and computer software packages may also be used.

For purposes of statistical analysis and graphical display, the raw data on brain activity is usually grouped into voxels corresponding to fixed volumes of the subject brain. The voxel size can be varied depending upon the resolution capability of the brain activity measuring device or the desired degree of precision in identifying brain regions. It should be noted, however, that smaller voxels have worse signal to noise ratios and greater susceptibility artifacts due to partial volume effects. Typically, voxels are cubes measuring, for example, 2-7 mm per side (e.g., 4×4×4 mm), but non-cubic voxels can also be employed (e.g., 3.0×3.2×3.2 mm). The data can be displayed graphically by color-coding the voxels according to some statistical value (e.g., z-score), and showing cross-sections in which levels of activity or changes in levels of activity are mapped in two-dimensions. By generating a series of such co-planar cross-sections, the entire brain volume can be mapped.

In some embodiments, SPECT, PET or fMRI data is analyzed using one of the SPM software programs (e.g., SPM'96, SPM'99, SPM2). The SPM software uses a parametric statistical model at each voxel, using a general linear model to describe the variability of the data in terms of experimental and confounding effects, and residual variability. Hypotheses expressed in terms of the model parameters are assessed at each voxel with univariate statistics. Temporal convolution of the general linear model for fMRI enables the application of results from serially correlated regression, permitting the construction of statistic images from fMRI time series. The multiple comparisons problem of simultaneously assessing all the voxel statistics is addressed using the theory of continuous random fields, assuming the statistic image to be a good lattice representation of an underlying continuous stationary random field. Results for the Euler characteristic lead to corrected p-values for each voxel hypothesis. In addition, the theory permits the computation of corrected p-values for clusters of k voxels exceeding a given threshold, and for entire sets of supra-threshold clusters, leading to more powerful statistical tests at the expense of some localizing power. See Friston et al. (1995), and Ashburner and Friston (1999).

When conducting statistical analyses on brain images, the investigator can choose an appropriate probability value for assessing statistical significance. The particular value chosen can vary depending upon the purpose of the statistical analysis and the level of certainty required. For example, when assessing groups of individuals to identify brain regions potentially involved in deception, a lower threshold of statistical significance may be employed. On the other hand, when analyzing an individual subject for forensic purposes, a higher statistical threshold can be employed. In the studies described below, for example, the level for statistical significance was chosen to be $p<0.05$. Thus, for one-tailed tests based on comparisons of z-scores, a threshold of $z=1.645$ can be employed, and for two-tailed tests, a threshold of $z=1.960$ can be employed.

Alternatively, thresholds can be chosen based not upon probability values but, rather, to select a pre-determined number of activated voxels. For example, the 10, 100 or 1000 largest z-scores can be identified, and only those can be included in a map or subsequent analysis.

In other embodiments, a threshold value can be chosen based upon a comparison to a control response. For example, the subject can be asked to perform a simple motor task such as raising a finger or pushing a button, or this task can be part of the act of responding to a question. Alternatively, the subject can be exposed to an auditory, visual, tactile, pain or other stimulus. The brain activity associated with the performance of the task or response to the stimulus, or some percentage or multiple of that brain activity, can be used as a threshold for identifying significant brain activity in other regions associated with other activities. For example, motor responses typically have greater signal-to-noise ratios and, therefore, a fraction of a motor response signal might be employed as a threshold. Alternatively, the motor responses of different individuals could be normalized to account for differences between individuals. Measurements of Skin Conductance Response (SCR).

In some embodiments of the methods of the invention, an SCR measuring device is used concurrently with a brain activity measuring device to provide additional data that may be indicative of deception. Devices for measuring SCR, also known as electrodermal activity (EDA) or galvanic skin response (GSR), are well known in the art and are regularly used in polygraphs. In accordance with the invention, however, the devices can be connected to a computer system processor which is also connected to the brain activity measuring device such that both devices provide data to the system processor, thereby allowing both sets of data to be analyzed together.

SCR measuring devices consist of at least one pair of electrodes which is attached to the skin of the subject. The electrodes can be attached to essentially any surface which provides for good electrical contact. In order to obtain good signals, areas with little or no hair, and areas with higher densities of sweat glands can be preferred (e.g., the palms of the hands). In some embodiments, a device for maintaining substantially constant contact between the SCR electrode and the subject's skin is employed. For example, a clamp can be used to apply substantially constant pressure to the electrodes, or the electrodes can be placed inside a tightly fitted glove or gantlet which is worn by the subject. On some embodiments, the device for maintaining substantially constant contact also immobilizes the area of the contact (e.g., the hand) to prevent any disturbance of the electrodes. For example, in one embodiment, the device for maintaining contact and immobilizing the area fits over the subject's wrist, and is constructed from a section of pipe (e.g., 10" length of 4" diameter PVC pipe) cut in half lengthwise, to which is mounted a flat member (e.g., ¼" thick Lexan sheet) with adjustable bolts to achieve substantially constant pressure to the electrodes. The sheet and pipe can be padded to increased comfort.

In those embodiments in which the brain activity measuring device is an MRI device, the strong magnetic fields generated by that device can interfere with the electrical signal to be conducted from the SCR measuring device to the system processor. Therefore, in those embodiments, non-ferrous connectors (e.g., snap-on ECG connectors) and a shielded cable (e.g., shielded twisted pair cable) is used to reduce such interference. In addition, a low-pass filter (e.g., 1 Hz cut-off) can be used to eliminate some of the interference generated by the MRI device.

In some embodiments, in order to conduct statistical analysis of the combined fMRI and SCR data, it is necessary to adjust the data such that there is one SCR datum for each voxel for each unit of time sampled. Thus, because the SCR data does not map to any particular brain region, the SCR data can be simply repeated for each voxel under consideration. In addition, if the sampling rates of the MRI and SCR devices differ, either the data set with fewer time points can be replicated to provide the missing time points, or the data set with more time points can be averaged over time to reduce the extra time points. Thus, for example, for an SCR device with a sampling rate of 100 per second and an MRI device with a 3 second sampling rate (i.e., TR=3000 ms), there are 300 SCR time points for each MRI time point and, therefore, each set of 300 sequential SCR time points can be averaged and associated with a single MRI time point. The adjusted SCR data can then be statistically analyzed as a co-variate with the brain activity level (e.g., correlated using a Pearson's r-correlation, or producing a z-map as described below in Example 1).

Systems for Detecting Deception by Measuring Brain Activity.

In another aspect, the invention provides systems for detecting deception by measuring brain activity. In some embodiments, the system includes means for providing a stimulus of interest to a subject, a brain activity measuring device (e.g., an MRI, PET, SPECT, qEEG, MEG or DOT device), a response measuring device and a system processor connected to each of the means for providing a stimulus, the brain activity measuring device and the response measuring device for receiving and processing data from them. The system processor can include software which conducts statistical analysis of the brain activity data by generating brain maps which correspond to differences between responses to truthful control questions and deceptive control questions, and between responses to questions of interest and truthful and/or deceptive control questions.

The means for providing a stimulus can be any device which can transmit aural or visual stimuli to the subject. Thus, for example, the device can be an audio speaker, a video screen or video goggles. The device can also include a mirror which allows the subject to view source of stimuli (e.g., a video screen, projection screen, printed matter, or an individual) which is displaced from the subject's line of sight.

The response measuring device can be any device which can receive and transmit the subject's responses to control questions and questions of interest to the system processor. For example, the device can include one or more buttons or switches which are activated by a finger of the subject, or can include a joystick or computer mouse. In other embodiments, the response measuring device can record the subject's responses by video. For example, the subject can respond by making raising one or more fingers or making some other pre-arranged physical movement (e.g., blinking). The response measuring device can record these responses, and the data subsequently can be analyzed in conjunction with the brain activity data.

In some embodiments, the means for providing a stimulus and the response measuring device are integrated to facilitate coordination and analysis of the stimuli/questions and responses. One such integrated device which is commercially available for use with MRI devices is the IFIS™ system (MRI Devices Corporation, Gainesville, Fla.).

In some embodiments, the invention provides a system which includes a brain activity measuring device (e.g., an MRI, PET, SPECT, qEEG, MEG or DOT device), an SCR measuring device and a system processor connected to both the brain activity measuring device and the skin conductance response measuring device for receiving and processing data from them. The system processor can include software which conducts statistical analysis of the brain activity data by generating brain maps which correspond to differences between responses to truthful control questions and deceptive control questions, and between responses to questions of interest and truthful and/or deceptive control questions. In some embodiments, the system can further include a means for providing a stimulus and a response measuring device, as described above. In embodiments employing an MRI device, the system can further include a shielded data cable for transmitting data from the SCR measuring device to the system processor. In some such embodiments, the system can further comprise a low-pass (e.g., 1 Hz) filter for signal from the SCR measuring device.

The SCR measuring device includes at least one pair of electrodes to be attached to an area of the subject's skin. In some embodiments, as described above, the SCR measuring device further includes a device for maintaining substantially constant contact between the SCR electrode and the subject's skin.

In some embodiments, the brain activity measuring device is an MRI device, such as a 1.5 T or 3.0 T device. In these embodiments, the strong magnetic fields generated by the MRI device make it necessary to magnetically isolate other electronic components. Current MRI devices are installed in specially-designed chambers which achieve such isolation. However, such chambers are not designed to accommodate an SCR measuring device and its cable connection to a system processor outside the chamber. Therefore, in some embodiments, the invention provides a partition, hatch, or door including an electrical connection called a penetration panel. The door is an electrically conductive panel, e.g., an aluminum screen or ¼" thick aluminum plate, and in some embodiments includes electrically conductive contact strips attached to the panel and distributed around the door periphery to provide a shielding seal and a mechanical seal between the panel and the doorway. For example, the strips can be contact fingers compressed 70% of their width when the door is closed. The door can be made translucent or transparent to allow a person outside the room to observe activity within the room.

The penetration panel can include a connector for attachment to a shielded data cable on the side exterior to the chamber, where the shielding serves to protect the data from noise induced by the magnetic fields of the MRI device. The penetration panel also includes a connector for attachment of an SCR cable that leads the SCR monitoring device and the electrodes in contact with the subject's skin. Thus the penetration panel serves to pass data from the inside of the chamber to the outside. The connectors can be mounted in a connector enclosure. In some embodiments, the connector enclosure provides for filtering of the signals or other data processing. Such filtering can be performed using passive elements (e.g., capacitors and inductors) or active elements (e.g., transistors and amplifiers).

In some embodiments, the SCR measuring device transmits SCR data with magnitudes ranging from $SCR_{min}$~0.01 µS to $SCR_{max}$~1 µS. In order to ensure adequate resolution in measuring the SCR, the system suppresses interference during operation to a level σ which is at least an order of magnitude below $SCR_{min}$. This can be accomplished by using a low-pass filter with a 3 dB cutoff frequency of approximately 1 Hz. For example, in some embodiments, the SCR measuring device can comprise a Wheatstone bridge (e.g., with a 10-turn potentiometer variable resistor), a differential amplifier (e.g., amplifier gain >610), and a low-pass filter, with all fixed resistors having approximately 1% tolerance and the minimum bridge output voltage being approximately 1 µV.

In each of the foregoing embodiments, the system processor can be adapted to receive brain activity data from the brain activity measuring device and to receive SCR data from the SCR measuring device, and is programmed to determine whether the brain activity of the subject during the response(s) to the question(s) of interest is characteristic of a truthful or a deceptive response. In some embodiments, the system processor is adapted to store the data or statistical analyses on an electronic data storage medium (e.g., a hard disk, floppy disk, compact disk, magnetic tape).

The following examples illustrate certain modes and principles relating to the practice of the invention, but are not intended to limit the scope of the invention claimed.

EXAMPLE 1

Subjects.

Eight healthy men were examined. The subjects were 21-28 years old (mean age 25), and scored 9-12 (mean score 11) on the Annett Handedness scale for right handedness (Annett (1970)). It was also required that the subjects be able to read and write English; and have the capacity to provide informed consent. Potential subjects were excluded if they had (1) a history of any current or past Axis I Psychiatric Disorder other than simple phobias but including substance abuse/dependence as determined by the Structured Clinical Interview for DSM-IV Axis I Disorders (SCID-1) (First et al. (1995)); (2) a history of neurologic disease; (3) a currently unstable medical condition; (4) used psychotropic medication within 5 half-lives of the procedure time; (5) caffeinism; (6) nicotine use; (7) any metal implants or shrapnel which would make an MRI procedure unsafe; (8) irremovable medical devices such as pacemakers or fixed hearing aids; (9) previous inability to tolerate an MRI procedure; or (10) claustrophobia severe enough to induce substantial anxiety in closed spaces.

Brain Activity Measurements.

Brain activity was measured using BOLD fMRI. The images were acquired using a Picker Edge™ 1.5 T MRI scanner (Picker International, Inc., Cleveland, Ohio) equipped with an actively shielded magnet and high performance whole-body gradients (27 mT/m, 72 T/m-sec). A 15-slice Time-to-Echo (TE) 20 ms structural scan was obtained to evaluate for any structural pathology. The BOLD fMRI consisted of 15 coplanar transverse slices (8.0 mm thick/0 mm gap) covering the entire brain and positioned 90° to the Anterior Commissure-Posterior Commissure (AC-PC) line using a sagittal scout image. Each fMRI volume consisted of BOLD weighted transverse scans and used an asymmetric-spin gradient echo, echo-planar (EPI) fMRI sequence (flip angle=90° to the AC-PC line; TE 45.0 ms; Time-to-Repetition (TR) 3000 ms; fifteen 8 mm thick/0 mm gap transverse slices; Field-of-View (FOV) 300×300 mm; in-plane resolution 2.109×2.109 mm; through-plane resolution 8 mm; frequency selective fat suppression). Given these parameters for the fMRI, a set of fifteen 8 mm thick/0 gap transverse slices covering the entire brain was obtained every 3 seconds.

Using BOLD fMRI, brain regions known to be activated during response inhibition (related to the orbitofrontal cortex (OFCx)) (Elliott et al. (2000), divided attention (involving the anterior cingulate (AC)) (Pardo et al. (1991); George et al. (1997); Bush et al. (1998)), and anxiety (involving the amygdala) (Rauch and Savage (1997)) were tested to assess activity during deception. Brain activity was investigated initially as for groups and then for individuals. In order to investigate the correlates of brain activation and psychophysiologic parameters during deception, the relationship between SCR and BOLD-fMRI signal changes were examined.

Deception Test Paradigm.

The subjects were escorted to each of two rooms, one of which was called the "Truth Room" and the other of which was called the "Deception Room." There were five different objects in each room, with objects differing between rooms, for a total of ten unique objects in the two rooms. The order of visits to the two rooms was randomized, with half of the subjects going to the Truth Room first and the other half going to the Deception Room first. Within each room, subjects were instructed to find a fifty-dollar bill which was concealed under one of five objects, to remember the location of the money, and to leave it in place. The subjects were then placed in the MRI scanner and provided with video goggles which were connected to a computer system and which displayed pictures of the objects in the Truth and Deception Rooms. SCR electrodes were attached to each subject's left hand, and the data (sampling rate 100 per second) was recorded using LabView™ 5.0.1 (National Instruments, Inc., Austin, Tex.) on a G4 Macintosh™ (Apple Computer, Inc., Sunnyvale, Calif.), as described in Shastri et al. (2001).

A control question test paradigm was utilized in which the subjects would give both truthful and deceptive answers about the location of the money while the BOLD fMRI scans were being acquired. Through the video goggles, the subjects were shown prompt screens and then pictures of the objects in the rooms in which the money had been concealed. If a subject had first visited the Truth Room, he was first shown only the Truth Room objects, followed by the Deception Room objects. Conversely, if the subject had first visited the Deception Room, he was first shown only the Deception Room objects, followed by the Truth Room objects. The five objects in each room were each shown once in a block, with a total of four blocks per room. The order of the objects was randomized within each block. Before the picture of the first object and between the pictures of each object in the rooms, a prompt screen was displayed that instructed the subject to raise either one finger for "yes" or two fingers for "no" to indicate whether the money was concealed under an object as soon as a picture of the object was displayed in the goggles. The object and the prompt were each displayed for 10.2 seconds, and responses were monitored by an observer.

For the Truth Room, subjects were instructed to accurately report the location of the money by raising the right index finger (one finger) when they were shown an object under which the money had been concealed, and by raising the right index and middle finger (two fingers) when shown an object under which the money was not concealed. These questions served as truthful control questions with which the responses to deceptive control questions were compared.

For the Deception Room, subjects were instructed to choose an object that did not have money concealed under it and to respond affirmatively by raising the right index finger (one finger). This required a deceptive affirmative response about the money location. They were also asked to respond negatively by raising the right index and middle finger (two fingers) to all other objects shown, including the object under which the money was concealed. This required a deceptive negative response about the money location. The money was concealed under the same object for all subjects and, therefore, the subjects were consistently lying when the object with money concealed under it was shown.

Subjects were told that an investigator unaware of the true location of the money would attempt to determine when they were being deceptive by observing their behavior in the scanner through the control room window. Subjects were also told that they would receive $50 if the subjects accurately reported the position of the money in the Truth Room, and an additional $50 if they successfully deceived the investigator regarding the location of the money in the Deception Room. The monetary rewards were included to increase the motivation and the anxiety during deception task.

All subjects correctly responded as instructed for both the Truth Room and Deception Room questions. For the Deception Room questions, each subject consistently provided the same deceptive response for each block of questions, although the object chosen for the affirmative deception varied across the individuals.

Functional Magnetic Resonance Imaging Method.

Functional MRI data were analyzed with MEDx 3.3™ software (Medical Numerics, Inc., Sterling, Va.) for the visualization, processing, and analysis of medical images, and which includes the SPM96 statistical package and Talairach and Tournoux brain template. Initially, the MEDx motion detection function was performed using the center of intensity weighting method. Any motion greater than 2.0 mm from reference volume would have been corrected using the MEDx 3.3 motion correction function, but no subjects required motion correction, with the largest movement being in the range of 0.4 to -1.7 mm. Next, individual volumes were spatially normalized into Talairach space utilizing the SPM Module 96 in MEDx 3.3. Algorithm parameters included Basic functions and smoothing, $x=4$, $y=5$, $z=1$, iteration=2, smoothing=8.0, deformation=0.2, the SPM template corresponding to the original Talairach and Tournoux atlas (Talairach and Tournoux (1988)) and output voxel size 4×4×4 mm. Using the SPM module again, spatial smoothing was performed using an 8×8×8 mm Gaussian kernel. Intensity normalization was performed which first created a "within the brain" mask that only included voxels if they had an intensity greater than 35% the maximum of each image volume for all time points and then scaled the remaining non-zero voxels in each volume in the time series to a mean value of 1000. High pass temporal filtering was then performed to filter-out patterns greater than twice the cycle length of 204 seconds. Due to the SPM module performing another intensity mask during the upcoming SPM statistics step, a software program was written to add 100 to all voxels outside the brain. When the SPM statistics were run, this ensured that no voxels previously defined as within the brain would be eliminated from the analysis but that voxels previously defined as outside the brain would be eliminated.

Identification of Measurement Periods.

Using the SPM module on MEDx 3.3, statistical analysis with a delayed boxcar design without temporal filtering was performed. The epochs were grouped as Lie (the time period when individuals gave a deceptive answer—both indicating that the object did not conceal money when it did {4 epochs} and indicating the object concealed money when it did not {4 epochs}), Lprompt (time period prompt image displayed just prior to each Lie {8 epochs}), True1 (time period subjects answered truthfully the location of the money {4 epochs} and 4 truthful answers that the money was not under an object—temporally surrounding deceptive answers {4 epochs}), Prompt (time period prompt displayed immediately preceding True1 epochs), True (time period of all remaining truthful answers {24 epochs}), and Prompt (time period of prompt immediately preceding True epochs{24}). Using these epochs, Lie minus True1 and True1 minus Lie was computed with no threshold (p=0.05 and uncorrected k (cluster size)=1). The individual unthresholded images were used to obtain group and individual activation profiles.

Group Analyses.

Raw brain activity data for each individual was normalized by transforming the data points to z-scores (i.e., by subtracting from each data point the mean value of all data points and then dividing by the standard deviation, to produce a set of z-scores with a mean vale of 0.0 and a standard deviation of 1.0). The resultant z-scores for each voxel or changes in z-scores for each voxel, were mapped to produce z-maps.

To calculate results for the group of individual subjects, the image calculator in MEDx 3.3 was used to compute unthresholded Lie minus True1 z-maps containing both positive and negative z-scores. That is, the image calculator was used to obtain the results of (Lie minus True1) minus (True1 minus Lie) z-maps for each subject. Once these results were obtained for each individual, images were summed and divided by the square root of the sample size (i.e., eight) to create the group fixed effects analysis unthresholded z-map. The resulting image was then analyzed with MEDx 3.3 cluster detection with a minimum of z=1.645 (i.e., the one-sided value for $p \leq 0.05$ in the z-distribution) and spatial extent threshold of $p \leq 0.05$ (i.e., the probability that the signal is due to chance as opposed to event-related). A low statistical threshold was chosen since the paradigm could have only a limited number of epochs of Lie. The resulting values were used to determine local maxima and visually present the significant clusters. Specifically, the Talairach Daemon interface in MEDx 3.3 was used to identify locations of the local maxima (Lancaster et al. (1997)) and the Talairach atlas (Talairach and Tournoux (1988)) was used to confirm the location of the significant clusters. The definition of the orbitofrontal cortex was based on the Johns Hopkins University BRAID imaging database for the Damasio Talairach space. The MRIcro software was used to identify anatomical areas.

The results are shown in Table 1, in which z-scores are calculated as described above, x, y and z coordinates are based upon the MNI template, and BAs are as reported by the MEDx 3.3 software.

TABLE 1

Group Analysis of Significant Changes in Regional Blood Flow for Lie minus True1

| z-Score | X | Y | Z | BA | Anatomic Area[1] |
|---|---|---|---|---|---|
| 3.49 | −64 | −40 | −4 | 21 | L[2] Middle Temporal Gyrus |
| 3.05 | 56 | 12 | 8 | 44 | R[3] Precentral Gyrus |
| 3.00 | 44 | 44 | −8 | | R Middle Frontal Gyrus (OF)[4] |
| 2.89 | −36 | −48 | −32 | | L Cerebellum Posterior Lobe |
| 2.77 | −48 | −24 | 4 | | L Superior Temporal Gyrus |
| 2.73 | −56 | −56 | −8 | 37 | L Inferior Temporal Gyrus |
| 2.48 | 20 | 56 | 12 | | R Superior Frontal Gyrus |
| 2.32 | −28 | −32 | −28 | | L Cerebellum Anterior Lobe |
| 2.03 | 56 | 8 | 20 | 44 | R Inferior Frontal Gyrus (OF) |
| 2.00 | 12 | 52 | 0 | | R Anterior Cingulate Cortex |

[1]Predominant anatomic area of significant BOLD signal as determined using MRIcro.
[2]L = Left.
[3]R = Right.
[4]OF = Orbitofrontal.

Thus, this study revealed significant activation during deceptive responses compared with truthful responses (z>1.645 with an extent threshold of p<0.05) in the right frontal (superior, middle, and inferior, including the orbitofrontal) areas, right anterior cingulate gyrus, and right precentral gyrus.

Individual Analyses.

For individual analyses, the unthresholded images of True1 minus Lie were subtracted from Lie minus True1 as described above for the group analyses. The resulting image was analyzed using MEDx 3.3 cluster detection with a minimum of z=1.645 and extent threshold of 0.05. The resulting values were used to determine local maxima and generate a visual representation of those significant clusters as described above.

The heterogeneity among the subjects in brain activation during the deception task was examined. Each individual was studied to determine if he had significant activation in any of the regions identified in the group analysis during the deception minus true comparison. Using a minimum statistical threshold of z=1.645 and extent threshold of 0.05, one subject had no significant activation, while seven others showed diverse activation patterns. Within subject BOLD fMRI analysis of Lie minus True1 generated large variations in the areas of significant differences in blood flow across the group, and no one brain region was found activated for all subjects. The mean number of discrete regions identified by the group analysis that were activated was 2 per individual subject, with a range of 0 to 6.

One explanation for this lack of consistency across individuals is the limited number of epochs that could be classified as deception. There were only eight epochs where the subjects attempted to deceive. Increasing the number of epochs can significantly improve the signal to noise ratio within an individual. Therefore, in some embodiments, a greater number of epochs of deception can be measured in order to increase the power for the individual analysis. In addition, the analysis can include a motion correction on all of the subjects regardless of the degree of movement and a more stringent threshold for significance. In addition, stronger magnetic fields and more sensitive RF measurement devices can be employed (e.g., 3.0 T field and sensitivity encoding technology).

Skin Conductance Response Analyses.

In order to correlate SCR with the BOLD fMRI signal, the MEDx 3.3 analysis package requires an equal number of volumes and SCR data points. The SCR data corresponding to each volume (TR=3 seconds) were averaged using STATA®statistical software (UCLA Academic Technology Services, Los Angeles, Calif.). Every sequential 300 SCR data points (sampling rate was 100 per second) were averaged to a single point. A total of 272 means corresponding to functional brain volumes were compared. The volumes utilized were the ones that had been motion detected, spatially normalized, smoothed, intensity normalized, and temporally filtered as described above. Using MEDx 3.3, independent of the deception paradigm, the changes in SCR were correlated with BOLD fMRI changes using Pearson's r-correlation. This analysis was performed for each individual resulting in individual z-maps. One of the correlation z-maps was found to have a significant artifact and, therefore, was excluded from the subsequent individual and group analyses.

For the group analysis, the remaining seven individual z-maps were added using the MEDx 3.3 calculator and divided by the square root of the sample size (i.e., seven). The resulting image was then analyzed with the MEDx 3.3 cluster detection with a minimum of z=1.960 (i.e., the two-sided value for $p \leq 0.05$ in the z-distribution) and spatial extent threshold of $p \leq 0.05$. In the direct BOLD comparison above (Lie minus True1), only eight epochs were used. For the correlational analysis, all time points were used, justifying the use of the larger z value threshold. The resulting values were used to determine local maxima and visually present the significant clusters as described above.

For the individual analyses, the individual correlation z-maps were each analyzed using the MEDx 3.3 cluster detection with a minimum of z=1.960 and spatial extent threshold of $p \leq 0.05$. The resulting values were used to determine local maxima and generate a visual representation of those significant clusters as described above.

The results of the group analyses are shown in Table 2, in which z-scores are calculated as described above, x, y and z coordinates are based upon the MNI template, and BAs are as reported by the MEDx 3.3 software. The MRIcro software was used to identify anatomical areas. Significant activation was found in the orbitofrontal and right anterior cingulate gyrus.

TABLE 2

Group Analysis of Significant Changes in Regional Blood Flow Correlated to SCR

| z-Score | X | Y | Z | BA | Anatomic Area[1] |
|---|---|---|---|---|---|
| 11.04 | 36 | 32 | −16 | | R[2] Inferior Frontal Gyrus (OF)[4] |
| 6.98 | 56 | 28 | −8 | 47 | R Inferior Frontal Gyrus GM[5] (OF) |
| 5.11 | 56 | 32 | 16 | 46 | R Middle Frontal Gyrus GM (OF) |
| 5.01 | 12 | 36 | 24 | 32 | R Anterior Cingulate GM |
| 4.27 | −48 | −48 | 40 | | L[3] Inferior Parietal Lobule WM[6] |
| | | | | 40 | L Inferior Parietal Lobule GM |
| 3.89 | 12 | 8 | 12 | | R Sub-lobar Caudate GM Caudate Body |
| 3.59 | 48 | 32 | 36 | | R Middle Frontal Gyrus |
| | | | | 9 | R Middle Frontal Gyrus GM |
| 3.51 | 64 | −32 | 4 | 22 | R Middle Temporal Gyrus GM |
| 3.30 | 8 | −4 | −4 | | R Sub-lobar GM Hypothalamus |
| 2.73 | −4 | −24 | 40 | 31 | L Cingulate Gyrus GM |
| 2.63 | 56 | −40 | −16 | | R Inferior Temporal Gyrus WM |
| | | | | 20 | R Inferior Temporal Gyrus GM |

[1]Predominant anatomic area of significant BOLD signal as determined using MRIcro.
[2]R = Right.
[3]L = Left.
[4]OF = Orbitofrontal.
[5]GM = Gray matter.
[6]WM = White matter.

The group analysis result correlating changes in SCR and BOLD fMRI signal revealed significant correlations between SCR and brain activity in the same two regions (OFCx and AC) that significantly activated in the Lie minus True1 group analysis.

Of the seven subjects included in the individual analyses, six had significant (z>1.960 and extent threshold <0.05) right orbitofrontal activation, and five had significant (z>1.960 and extent threshold <0.05) right anterior cingulate activation. No other regions consistently activated across individuals.

EXAMPLE 2

Subjects.

Thirteen subjects were scanned, but three were excluded for failure to provide deceptive responses as instructed. Ten healthy subjects (7 men and 3 women) were examined. The subjects were 20-35 years old (mean age 27.8), and scored 10-12 (mean score 11.2) on the Annett Handedness scale for right handedness (Annett (1970)). It was also required that the subjects be able to read and write English; and have the capacity to provide informed consent. Potential subjects were excluded if they had (1) a history of any current or past Axis I Psychiatric Disorder other than simple phobias but including substance abuse/dependence as determined by the Structured Clinical Interview for DSM-IV Axis I Disorders (SCID-I) (First et al. (1995)); (2) a history of neurologic disease; (3) a currently unstable medical condition; (4) used psychotropic medication within 5 half-lives of the procedure time; (5) caffeinism; (6) nicotine use; (7) any metal implants or shrapnel which would make an MRI procedure unsafe; (8) irremovable medical devices such as pacemakers or fixed hearing aids; (9) previous inability to tolerate an MRI procedure; or (10) claustrophobia severe enough to induce substantial anxiety in closed spaces. Prior to scanning, female subjects were given a pregnancy test and excluded if it was positive.

Brain Activity Measurements.

Brain activity was measured using BOLD fMRI. The images were acquired using a Philips Intera 3 T MRI scanner. The BOLD fMRI scans consisted of 26 coplanar transverse slices (4.0 mm thick/1 mm gap) covering the entire brain and positioned 90° to the AC-PC line using a sagittal scout image. Each fMRI volume consisted of BOLD weighted transverse scans and used a single shot gradient EPI sequence (flip angle=90°; TE 30.0 ms; TR 3000 ms; FOV 256×256; matrix 64×64 mm; in-plane resolution 4.0 mm×4.0 mm; through-plane resolution 4 mm). Given these parameters, a set of 120 whole brain volumes was acquired for each run (total of 240 volumes for the study). Following the BOLD fMRI, a structural T1 weighted scan was acquired to insure no major structural abnormalities. The images in these experiments were acquired at a higher field strength (3.0 T versus 1.5 T) than those in Example 1.

Images were displayed to the subjects and responses recorded using an IFIS™ system (MRI Devices Corporation, Gainesville, Fla.).

Deception Test Paradigm.

Subjects were escorted into a room in which six objects were located. Fifty-dollar bills had been placed under two of the objects before the subject entered. The subjects were instructed to find both locations of the two fifty-dollar bills and to leave them in place. The subjects were then made safe to enter the MRI scanner by removing metal objects and by providing hearing protection.

Subjects were instructed that they would see pictures of the six objects from the room just visited while in the MRI scanner. The picture of each object would be presented to them multiple times. For each picture, the subject would respond whether money was concealed below the object. The subject would respond "yes" by pushing the right thumb button and "no" by pressing the right index finger button of the IFIS system. The subjects were instructed to choose one of the two objects concealing a fifty-dollar bill and to respond truthfully (i.e., "yes" with the thumb) when presented with an image of that object. The subjects were informed that they would receive $50 for truthfully responding. This question served as a truthful control question. For the other object concealing the other fifty-dollar bill, the subjects were instructed to respond deceptively (i.e., "no" with the index finger) when presented with an image of that object. In addition, the subjects were instructed to choose one of the objects which had not concealed a fifty-dollar bill and to respond deceptively (i.e., "yes" with the thumb) when presented with an image of that object. These two questions served as deceptive control questions. The subjects were told that a research assistant who did not know the location of the money would attempt to determine whether the subject was being deceptive. The subjects were informed that they would receive an additional $50 if the research assistant could not tell when the subject was being deceptive. The research assistant and the IFIS system recorded the subject's responses.

For each subject, the tests consisted of 2 runs of 10 blocks. During each block, an image of each of the six objects was presented for six seconds in randomized order. Therefore, each block was 36 seconds and each run was six minutes. There was a one-minute break between runs. Each block required two deceptive responses and four truthful responses. Therefore, these tests required a total of 40 deceptive responses and 80 truthful responses. Therefore, this design included 40 deceptive epochs rather than the 8 deceptive epochs in the design of Example 1.

Because each subject chose both one of the two objects concealing money to lie about and one of the four objects not concealing money to lie about, the order and timing of lying and truthful events were different across the group.

Functional Magnetic Resonance Imaging Method.

The image data were analyzed with Statistical Parametric Mapping 2 (SPM 2) software (www.fil.ion.bpmf.ac.uk/spm/). Initially, images were reoriented to the standard orientation for analysis. The volumes were then realigned and spatially normalized using the Montreal Neurologic Institute (MNI) EPI template in SPM 2. The resulting images were smoothed using a 6 mm kernel. An event model was designed for each subject using deceptive and truthful responses convolved with the hemodynamic response function. The data was modeled and estimations created. Individual analysis was performed with two contrasts: Lie (deceptive responses) minus True (truthful responses); and True minus Lie. Significance was defined as $p<0.001$ with a cluster value of p-corrected $<0.05$. A second level (random effects) group analysis was performed using a one-sample t-test ($p<0.001$, cluster-level p-corrected $<0.05$) of contrast images for both Lie minus True and True minus Lie. The statistical threshold used for final display and testing was higher for this study (random effects model, $p<0.001$, cluster p-corrected $<0.05$) than for the study of Example 1 (fixed effects model, $p<0.05$, cluster $p<0.05$). The MRIcro software (available at www.cla.sc.edu/psyc/faculty/rorden/mricro.html; see also Rorden and Brett (2000)) was used to determine the anatomic location and Brodmann areas for significant clusters of activation. The SPM functional map was superimposed on the T1 template skull stripped brain image in MRIcro.

In comparison to the study of Example 1, this study had a more conservative threshold for statistical significance (random-effects model with $p<0.001$ versus fixed-effects model with $p<0.05$) and used an event-related versus a block design. Nonetheless, as shown below (Tables 3 and 4), an increased level of statistical significance was observed for activation in five brain regions. This may be due to the increased number of deceptive epochs measured (8 versus 40) and the increased field strength of the MRI (1.5 T versus 3.0 T). The individual results also showed more consistency than the previous study, with seven of the ten subjects having significant activation in the right prefrontal cortex.

Identification of Measurement Periods.

The events analyzed were defined as Lie (subjects gave deceptive responses regarding whether the object was hiding money) and True (subjects gave truthful responses regarding whether the object was hiding money). Contrast maps of, Lie minus True and True minus Lie were computed. The individual contrast maps were used to obtain group and individual activation profiles.

Group Analyses.

The group analysis for Lie minus True revealed significant activation ($p<0.001$, cluster p-corrected $<0.05$) in five areas (right anterior cingulate, right inferior frontal, right orbitofrontal, right middle frontal, and left middle temporal) that are consistent with the study of Example 1. The group analysis of True minus Lie revealed no areas of significant activation.

The results are shown in Table 3, in which k is the number of voxels in a cluster, t is Student's t statistic, x, y and z coordinates are based upon the MNI template, and BAs are as reported by the MEDx 3.3 software.

TABLE 3

Group Analysis of Lie minus True[1]

| Cluster Level | | Voxel Level | | MNI Coordinates | | | | |
|---|---|---|---|---|---|---|---|---|
| k | p (corrected) | t | p (uncorrected) | X | Y | Z | BA | Anatomic Area[1] |
| 65 | 0.006 | 9.89 | <0.001 | 4 | −28 | 34 | 23 | R[2] Middle Cingulate |
| 81 | 0.001 | 8.53 | <0.001 | −40 | 26 | −8 | 47 | L[3] Inferior Orbitofrontal |
| 56 | 0.013 | 8.03 | <0.001 | 4 | 20 | 20 | 24 | R Anterior Cingulate |
|  |  |  |  | −4 | 24 | 20 | 24 | L Anterior Cingulate |
| 396 | 0.000 | 7.32 | <0.001 | 52 | 20 | 4 | 45 | R Inferior Frontal |
|  |  | 6.17 | <0.001 | 52 | 32 | 0 | 45 | R Inferior Orbitofrontal |
|  |  | 5.84 | <0.001 | 44 | 22 | 0 | 47 | R Insula |
| 67 | 0.005 | 7.07 | <0.001 | −60 | −60 | 8 | 37 | L Middle Temporal |
| 52 | 0.020 | 6.79 | <0.001 | 42 | 44 | 30 | 46 | R Middle Frontal |

TABLE 3-continued

Group Analysis of Lie minus True[1]

| Cluster Level | | Voxel Level | | MNI Coordinates | | | | |
|---|---|---|---|---|---|---|---|---|
| k | p (corrected) | t | p (uncorrected) | X | Y | Z | BA | Anatomic Area[1] |
| 131 | 0.000 | 6.12 | <0.001 | 10 | −78 | 20 | 18 | R Cuneus |
| 79 | 0.001 | 6.08 | <0.001 | −48 | −8 | 54 | 6 | L Post-Central |

[1]Predominant anatomic area of significant BOLD signal as determined using MRIcro.
[2]R = Right.
[3]L = Left.

Individual Analyses.

For the within individual results of Lie minus True, there was a variable degree and pattern of increased BOLD signal. Focusing on the areas that were dignificantly activated in the group analyses during deceptive responses in both this Example 2 and Example 1, 5 subjects had significant activation (p<0.001, cluster p-corrected <0.05) in the right orbitofrontal cortex, as shown in Table 5. Two subjects did not have any significant activation at this threshold. Taking a broader neuroanatomic perspective (i.e., prefrontal cortex versus only a portion of the prefrontal cortex, such as the orbitofrontal cortex), 7 of 10 subjects had significant right prefrontal activation during the Lie minus True contrast.

TABLE 4

Individual Analysis of Lie minus True

| Anatomic Location[1] | Subject | | | | | | | | | |
|---|---|---|---|---|---|---|---|---|---|---|
| | 001 | 002 | 006 | 007 | 008 | 009 | 010 | 011 | 012 | 013 |
| R[2] anterior cingulate | | | | | | | | | | x |
| R inferior frontal | x | | x | | | | | | | |
| R orbitofrontal | x | | x | | | x | | | x | x |
| L[3] middle temporal | | | | | | x | x | x | | |
| R middle frontal | | x | | | | x | | x | | |
| R prefrontal | x | x | x | | | x | | x | x | x |
| Other activation | | | | | x | | | | | |
| No Activation | | | | x | x | | | | | |

[1]Predominant anatomic area of significant BOLD signal as determined using MRIcro.
[2]R = Right.
[3]L = Left.

EXAMPLE 3

Subjects.

A subject of interest (e.g., a criminal defendant, an individual with access to confidential information) is identified for examination. Initially, subjects are assessed to determine that they are appropriate. Subjects of interest are not scanned if they have any metal implants or shrapnel which would make an MRI procedure unsafe; irremovable medical devices such as pacemakers or fixed hearing aids that would make the MRI procedure unsafe; or claustrophobia severe enough to induce overwhelming anxiety in closed spaces. The subject is subjected to extensive testing for the use of psychotropic drugs. In addition, medical history, psychiatric history, and handedness are carefully assessed. If the subject has taken psychotropic drugs within 5 half-lives, the test is delayed if possible until 5 half-lives have elapsed. Female subjects are given pregnancy tests. If the subject is pregnant, the test is delayed if possible until after the pregnancy. The ability of the subject of interest to read and write English is determined. If the subject cannot read and write English, a different language is chosen in which the subject has proficiency. If the subject has characteristics (e.g., sex, age, medical status) consistent with previously studied subjects, the results for the previous subjects can validate the applicability of the methods. If the subject differs substantially from previously studied subjects, a group of individuals with matched characteristics can be recruited to validate the methods for the group.

The day of scanning, the subject is taken through two fMRI examinations in which the method is first verified to be able to detect deception in the individual (the "verification paradigm"), and then the subject is tested for the questions of interest (the "testing paradigm"). For the verification paradigm, truthful and deceptive control questions and additional neutral control questions are randomly presented. The randomness of the questions prevents anticipation of responses. The verification paradigm establishes that the method is able to detect deception by the individual subject on that day. Following the verification paradigm, the subject performs the testing paradigm in which the structure is the same as the verification paradigm, but in which questions of interest are asked. In some circumstances, the subject is instructed to deny and admit during the question of interest. The same neutral control questions are used for both paradigms. Immediately following scanning, a final drug screen is performed to verify that no unknown substances were taken prior to or during scanning. Data analysis will include individual analysis on control questions and questions of interest using a whole-brain analysis and a region of interest approach.

Results will be compared to the group analyses generated from previous studies to determine if the subject uses the canonical deceptive brain regions previously identified. Reported results will consist of the deceptive brain regions that can be identified for the subject and the probability or statistical likelihood that the subject was truthful or deceptive in responding to the questions of interest.

Brain Activity Measurements.

Brain activity measurements are obtained by BOLD fMRI using a 3.0 T MRI scanner (e.g., Philips Intera 3 T) with a sensitivity encoding phased-array head coil (e.g., SENSE™ Head Coil, Philips Electronics, N.V., Amsterdam, Netherlands). The BOLD fMRI scans consist of 36 coplanar transverse slices (3.0 mm thick/0 mm gap) covering the entire brain and positioned 90° to the AC-PC line using a sagittal scout image. Each fMRI volume consists of BOLD weighted transverse scans and uses a single shot gradient EPI sequence (SENSE factor 2, flip angle=90°; TE 30.0 ms; TR 1867 ms; FOV 208×208; matrix 64×64 mm; in-plane resolution 3.25 mm×3.25 mm; through-plane resolution 3 mm). A set of 515 whole brain volumes are acquired for each paradigm. Following the BOLD fMRI, a structural T1 weighted scan is acquired to insure no major structural abnormalities.

Deception Verification Paradigm.

The subject is brought to a room in which there are two objects (e.g., a ring and a watch) which can potentially be "stolen." The subjects are given instructions to take one of the objects and are provided an incentive to successfully deceive the investigator. After the subjects take the chosen object and leave the room, an investigator enters the room to confirm which object was taken. The subjects are then placed in the MRI scanner with a video screen for presenting questions and a unit with finger-activated buttons for recording responses (e.g., IFIS-SA™ System, MRI Devices Corporation, Gainesville, Fla.). A series of questions are asked and the subjects respond "yes" or "no" by pressing a button. The questions are of three types: neutral control questions (e.g., "Are you male?"), truthful and deceptive control questions related to the first item (e.g., "Did you steal a ring?"), and truthful and deceptive control questions related to the second item (e.g., "Did you take the money?"). This protocol provides events of deception and events of truthfulness in the same run. There verification paradigm run is approximately 16 minutes for the subject.

Deception Testing Paradigm.

Testing for the information of interest is performed using the same type of questions and scanning parameters as the verification paradigm. The difference is that questions regarding the matter being tested are substituted for the questions about the ring and the watch. Questions of interest (e.g., "Did you commit the crime of which you are accused?" or "Did you sell the company's confidential information to a competitor?") are randomly interspersed with the neutral control questions. In some situations, subjects are instructed to both admit ("truth") and deny ("lie") the question of interest.

Functional Magnetic Resonance Imaging Method.

The image data are analyzed with SPM 2 software, essentially as described above. An event model is designed for each subject using deceptive and truthful control responses convolved with the hemodynamic response function. For the verification paradigm, individual analysis is performed with four contrasts: Lie (deceptive control responses) minus Control (neutral control responses); Control minus Lie; True (truthful control responses) minus Control; and Control minus True. Significance is defined as $p<0.001$ with a cluster value of p-corrected $<0.05$. The MRIcro software is used to determine the anatomic location and Brodmann Areas for significant clusters of activation and the SPM2 functional map is superimposed on the T1 template skull stripped brain image in MRIcro.

Next, Unknown (responses to questions of interest) minus Control and Control minus Unknown contrasts are performed for each subject. Significance is again defined as $p<0.001$ with a cluster value of p-corrected $<0.05$, and the MRIcro and SPM2 software are used as described above to identify areas of activation.

Regions which show significant activation for the testing paradigm in Unknown minus Control are compared with the regions identified as indicative of deception in the Lie minus Control of the verification paradigm. These regions are also compared with the True minus Control in the verification paradigm. Similarly, the Control minus Unknown of the testing paradigm is compared with the Control minus Lie and the Control minus True of the verification paradigm. Thus, the Unknown condition will be matched with either the truthful or the deceptive response pattern confirmed in the verification task.

EXAMPLE 4

Subjects.

The subjects were healthy unmedicated adults aged 18-50 years who were screened with a Structured Clinical Interview for DSM-IV Axis I Disorders (SCID-I) (First et al. 1995), a pre-MRI screening form, a medical history, and a physical exam. They were evaluated with an Annette Handedness Scale (Annett 1970) and the State-Trait Anxiety Inventory (STAI) (Spielberger et al 1983). A urine sample was obtained for a drug urinalysis and a urine pregnancy test (if a female of child-bearing potential).

Brain Activity Measurements.

All images were acquired with a 3T MRI scanner (Intera, Philips Medical System, The Netherlands) using an eight-channel SENSE head coil. Subjects performed the Motor task (6 minutes), then the Deception task (16 minutes), and finally a Ti-weighted structural scan. For the deception task, 515 echoplanar imaging (EPI) transverse images (TR 1867 ms, TE 30 ms, Flip Angle 90 deg, FOV 208 mm, matrix 64×64, SENSE factor 2, 36 slices, 3 mm with 0 mm gap, giving a voxel size of $3.25 \times 3.25 \times 3.00$ mm$^3$) were acquired that covered the entire brain and were positioned with reference to the anterior commissure-posterior commissure (AC-PC) line using a sagittal scout image.

Deception Test Paradigm.

Subjects were recruited from the university community at large to participate in a mock crime and then deny performing that crime while in an MR scanner. At the initial screening visit, informed written consent (approved by the Medical University of South Carolina's Office of Research Integrity) was obtained. Subjects were screened and excluded for taking medications/drugs, being pregnant, or having a medical or psychiatric illness. Further, subjects were given an opportunity to read the questions that they would be asked during the scanning day.

On the scanning day, subjects were taken to a specific room and instructed to "steal" a watch or a ring located in a drawer. The subjects placed the "stolen" object in a locker along with their other belongings while being observed by ELG. Subjects practiced a simple motor task and the deception task outside of the scanner. Images were visually displayed to the subjects and button press responses and response times recorded using an Integrated Functional Imaging System (IFIS) (MRI Devices Corp., Gainesville, Fla.). During the deception task, four types of questions were visually displayed to subjects: "ring"—regarding whether they took the ring; "watch"—regarding whether they took the watch; "neutral"—general questions with clear yes and no answers; and "control"—questions about doing minor wrongful acts. Subjects were instructed to answer the ring and watch questions as if they had stolen neither object and the control and neutral questions truthfully. Subjects were further informed that they would receive an additional $50 if the test administrator could not tell when they were lying while being observed answering questions in the scanner. This provided an incentive for subjects to attempt countermeasures when lying. Because of the inability to detect deception immediately during the scanning session, all subjects received the additional $50. After scanning, subjects completed a questionnaire about the study, including what types of countermeasures they attempted, if any.

The Motor task enabled the subjects to become familiar with the testing environment and to practice their responses of "Yes" and "No" with thumb and index finger respectively. For the Deception task, questions were presented visually for 3.5 seconds. After a question, there was a visual prompt for the subject to answer "Yes or No" for 2 seconds followed by a "+" for 0.5 seconds. Subjects were instructed not to answer until they saw the visual prompt of "Yes or No". The delayed response was to reduce the variability of response timing due to differences in reading speeds across questions and across subjects. Thus, each question took 6 seconds. There were 20 questions for each category (80 unique questions total). The order of the type of question (i.e., ring, watch, neutral, control) was pseudo-randomized using randomization.com. The randomization feature presented a control, neutral, ring or watch question, but did not specify the specific question, but consistent across subjects. The IFIS system pseudo-randomly chose the actual question for the appropriate category. Thus, the order of the type of questions was consistent across subjects, but the order of the actual questions asked was varied. The 80 questions were presented once for the practice and in two separate sets that were administered consecutively for the scanning.

Functional Magnetic Resonance Imaging Method.

For the behavioral data, responses (thumb pressed for "Yes", index finger pressed for "No") and reaction times were acquired via the IFIS. Data was inspected to verify subject behavioural participation in both the motor and deception tasks and to screen for irregularities. Responses that were not consistent, not answered, or not as specified in the protocol, were identified and modelled as separate "non protocol" events.

The analysis of the functional MRI data was performed using Statistical Parametric Mapping software (SPM 2, Wellcome Department of Cognitive Neurology, London, UK—run on Matlab version 6.5 Release 13.0.1). Pre-processing of the functional MRI data used the same SPM2 procedures and settings for both the Model-Building Group (MBG) and the Model-Testing Group (MTG). The MTG's pre-processing was performed using a script (modified from Rorden et al., http://www.psychology.nottingham.ac.uk/staff/cr1/spm2_batch/). The images were reoriented to match the SPM2 EPI template and then realigned and unwarped to correct head movements and resulting susceptibility distortions. Slice timing was performed to correct for differences in slice acquisition time. Functional images were then spatially normalized to the SPM EPI template and resampled with a voxel size of 3×3×3 mm (Ashburner and Friston 1999). After normalization, functional images were spatially smoothed using a Gaussian kernel with 8 mm full width at half maximum based on the suggested standard of 2 to 3 times the output spatially normalized voxel size. A general linear model within SPM2 was specified and estimated for the MBG and MTG to create individual t-maps. The event-related design was convolved with a hemodynamic response function that approximated the expected activation patterns. Effects at each and every voxel were estimated using the general linear model at the first statistical level. The motion-recorded parameters generated during the "Realign" process were included as six user-specified regressors. The non-protocol events were also included as a regressor. A high pass filter (cut off frequency=128 Hz) was used to remove possible effects of low-frequency changes. Individual activated t-maps were generated by defining the following contrasts and their inverse: Lie-Truth, Lie-Neutral, Lie-Control, Truth-Neutral, Truth-Control, and Neutral-Control. Individual contrast images generated at the first statistical level were then used to create group t-maps at the second level in a random effects model (Friston and Frackowiak 1997). Cluster analyses were performed at identical corrected threshold of $p<0.05$ (false discovery rate, FDR) for each group map with a spatial extent threshold of 25 voxels to correct for multiple comparisons (Friston et al 1994). A "3dmerge" program from Analysis of Functional Neuroimaging (AFNI, 2.56b)(Cox 1996) was used to label each cluster based on sizes of clusters from each cluster mask. Another AFNI program "3dcalc" was also used to separate each labeled cluster. Seven Lie-minus-True clusters from the group analysis were thus individually separated in this way. The clusters defined by the group statement were used as region of interests (ROIs) on each of the subject's individual t-maps. AFNI program "ROIstats" was used to determine the number of significantly activated voxels and average t-value for each cluster in each individual. MRIcro was used to display the group functional MRI maps, SPSS 11.0 was used to calculate t-tests and $102^2$, and Prism 4.0 to generate FIGS. 1 and 2.

Defining the Regions of Interest.

For the MBG, 31 subjects out of 34 who signed a written informed consent (Table 5) were enrolled in the study and 30 were successfully scanned. For the deception task, the group level analysis of Lie-minus-True revealed significant activation ($p<0.05$, FDR, cluster minimum 25) in seven clusters. All five hypothesis-driven brain regions (right anterior cingulate; right inferior orbitofrontal; right inferior frontal; right middle frontal and left middle temporal lobe) were significantly activated—consistent with two prior-studies (Kozel et al 2004a; Kozel et al 2004b) (FIG. 1 and Table 6).

For the seven clusters, the number of significantly activated voxels ($p<0.001$) was determined for each individual subject with the contrast of Lie-minus-True. The purpose was to identify the clusters that could be used as regions of interest that most consistently differentiated when an individual was being deceptive. The results revealed that significant activations in cluster 1 (28 subjects), cluster 2 (30 subjects), and cluster 4 (27 subjects) accounted for the majority of subjects' activations. Twenty-six subjects had significant activation in at least one of these three clusters. If the significance threshold was lowered ($p<0.05$), then all 30 subjects had activation in one of these clusters. The determination of which clusters to use was not based on an anatomic location but rather on the group activation map of Lie-minus-True. The three clusters chosen corresponded to areas that were hypothesized to be correlated with deception (i.e. Cluster 1—right anterior cingulate; Cluster 2—right orbitofrontal and inferior frontal; and Cluster 4—right middle frontal) and which overlapped with previous studies (Kozel et al 2004a; Kozel et al 2004b).

Determining the Contrast and Statistical Threshold.

Clusters 1, 2, and 4 were used as regions of interest for the individual analysis. Using the contrasts of Lie-minus-Control, True-minus-Control, Lie-minus-Neutral and True-minus-Neutral, the number of activated voxels and average t-values for each region (clusters 1, 2, and 4) were generated for each subject at various levels of significance ($p<0.05$, $p<0.01$, $p<0.005$, $p<0.001$, $p<0.0005$, and $p<0.0001$). Using Lie and True contrasts similar results were obtained (see FIG. 4, Tables 11, 12, and 13).

A number of differences were compared; the Neutral and Control Comparisons were analyzed separately (i.e. Lie and Truth versus Control questions [Control Comparisons]; Lie and Truth versus the Neutral questions [Neutral Comparisons] and Lie and Truth to each other. A number of methods were investigated to maximize the accuracy of detecting deceptive versus truthful responses. The resulting two models with the best predictability were tested in the MTG.

Large differences were observed in the degree of activation for each individual and therefore a single reference threshold of the number of activated voxels could not be set to accurately predict deception for the Lie contrasts (Lie-minus-Neutral, Lie-minus-Control, Lie-True) versus the True contrasts (True-minus-Neutral, True-minus-Control, True-Control). In order to account for the individual differences in activation, the number of significantly ($p<0.05$) activated voxels for the Lie contrasts was subtracted from the True contrasts using both Cluster 1, Cluster 2, Cluster 4 and the combined Clusters 1, 2, and 4 (FIG. 2 and FIG. 4, Table 10). If the resulting value was positive, then it correctly identified a lie. If the resulting value was zero, then it was called indeterminate. If the resulting value was negative, then it was falsely identified as a truth.

The Neutral questions were used in the Model-Testing Group because the mean differences in the number of activated voxels in the truth and lie conditions was greatest, and they provided questions whose accuracy could more easily be determined—though the ability to predict deception was similar in the control and neutral questions.

Applying this method to the MBG, on of ordinary skill in the art could accurately predict the object taken in 27 of 29 subjects, with one indeterminate (93% accurate, $\chi^2=19.20$, $p<0.0001$) for Cluster 1, 26 of 30 subjects (87% accurate, $\chi^2=16.13$, $p<0.0001$) for Cluster 2, 23 of 26 subjects and 4 indeterminate (88% accurate, $\chi^2=8.53$, $p<0.005$) for Cluster 4, and 28 of 30 subjects (93% accurate, $\chi^2=22.53$, $p<0.00001$) for Clusters 1, 2, and 4 (FIG. 3, Table 8).

Cluster 1 and the combined Clusters 1, 2, and 4 were used to test this analysis method in the MTG. The data from the MBG were used to develop a method of analysis—not to test a method or determine its predictive power. Testing of the method was done with the MTG.

Reaction times, belief they were participating in a theft, countermeasures and motivation by money were all analyzed to see if these could improve the model. None provided any better discriminatory power. Though reaction times have differentiated between truths and lies in previously published studies, this effect was not observed in this study. The likely explanation is that the delay between questions and responses in this paradigm normalizes any differences that may exist (Table 5).

To determine the appropriateness of this model Lie-Neutral and True-Neutral contrasts were compared to Lie-True and True-Lie contrasts. The mean and median number of activated voxels at a $p<0.05$ were determined for each individual in the MBG and calculated for the Lie-True, True-Lie, Lie-Neutral and True-Neutral contrasts (Table 12). A t-test was used to determine if a difference existed in the mean number of activated voxels in the Lie-True versus the True-Lie contrast and the Lie-Neutral versus the True-Neutral contrast. For clusters 1, 2, 4 and the combination of 1, 2 and 4 there were significantly more voxels activated in the Lie groups (Lie-Neutral and Lie-True) for each comparison (Table 12).

One of ordinary skill in the art will recognize that these methods are not only useful for detecting deception but provide a general procedure for detecting brain activation using functional magnetic resonance imaging for individuals.

Testing the fMRI Detection of Deception Model—Model Testing Group (MTG).

31 out of 32 subjects who signed a written informed consent for the MTG were enrolled in this study (Table 5). No significant demographic differences were identified between the MTG and the MBG. In this latter group, one subject was found to have a calcification of the falx cerebri, one subject did the reverse of the instructions, answering that he stole both the watch and the ring, and one subject started the paradigm, but was not scanned due to a concern about metal but was later determined not to have metal. The subject who did the reverse of instructions was included because he did lie. The subject with concerns about metal was started from the beginning of the protocol at a later date. The second time through the paradigm, she "stole" a different object from the first time. All subjects were included in the analysis, including the subject that started at a later date.

For the deception task, the group level analysis of Lie-minus-True revealed significant activation ($p<0.05$, FDR, cluster minimum 25) in seven clusters. Once again, the five brain regions consistent with the prior two studies (Kozel et al 2004a; Kozel et al 2004b) and the model-building group were significantly activated (FIG. 1 and Table 7, Table 10). Additionally, no significant difference between the MBG and MTG group maps of the Lie-minus-True analyses (two sample t-test, FDR $p<0.05$) was observed, though this study was not specifically designed to detect such a difference.

The MBG method using only Cluster 1 was able to successfully determine when the MTG subjects were being deceptive for 83% (25/30 with one indeterminate—$\chi^2=11.65$, $p<0.001$) of the subjects, while the combination of Clusters 1, 2, and 4 achieved a higher accuracy of 90% (28/31—$\chi^2=20.16$, $p<0.00001$) (FIG. 3).

EXAMPLE 5

Subjects.

Healthy men and women were included in the study if they were between the ages of 18-50, able to read and write in English and provided competent informed consent. Subjects were excluded if they had a history of any current or past Axis I Psychiatric Disorder except simple phobia, including substance abuse/dependence as determined by the SCID and DSM-IV (Diagnostic and Statistical Manual of Mental Disorders, Fourth Edition), had a history of CNS disease, including traumatic brain injury (i.e., any head trauma resulting in loss of consciousness, concussion, overnight hospitalization, or other neurologic sequelae), cerebrovascular disease, tumors, seizures (other than febrile seizures of childhood), meningitis, encephalitis, or abnormal CT or MRI of the brain, were currently in unstable medical condition which would preclude participation in the study, had a history of a continuing significant laboratory abnormality, had taken any psychotropic medication within 5 half-lives of procedure time, had caffeinism, were smokers, were lactating or pregnant females, had any metal implants (not including dental fillings), irremovable medical devices such as pacemakers or fixed hearing aids, or presence of shrapnel, had a previous inability to tolerate MRI procedure, were claustrophobic severely enough to induce substantial anxiety in closed spaces, or were not using one of the following methods of birth control: abstinence, condom plus spermicidal foam, or diaphragm plus spermicidal foam.

During the first visit the subjects were screened with clinical rating scales that required them to answer questions regarding their past and present medical histories. They were evaluated with an Annette Handedness Scale, the State-Trait Anxiety Inventory (STAI), and a Structured Clinical Interview for DSM-IV Axis I Disorders (SCID). A pre-MRI screening form was filled out to ensure the subject did not have any metal in or on his or her body, was not pregnant or lactating, or on any type of medication. They were then given a physical exam with an emphasis on neurologic function. A urine sample was obtained for a drug urinalysis and a urine pregnancy test (if the subject was a female of child-bearing potential).

During the second visit, the subjects performed the fMRI portion of the study. Upon arrival the subjects filled out the State Trait Anxiety Inventory. They were then led to a drawer in which a ring and a watch were kept. The subjects were instructed to choose one of the two objects to "steal" while a research assistant watched to ensure that the subjects took one object. The subjects were instructed to put the "stolen" object in a locker with the rest of their belongings.

The subjects were then taken to a computer where they ran through the question-and-answer paradigm and practiced answering the questions just as they would in the scanner. The subjects were told to respond "yes" or "no" by pressing a button on an IFIS system (MRI Devices, Gainesville, Fla.). The questions were of four types: neutral (e.g., "Do you live in South Carolina?"), control (e.g., "Have you ever lied to a loved one?"), related to stealing item one (e.g., "Did you steal the ring?"), or related to stealing item two (e.g., "Did you take the watch?").

The subjects were instructed to answer all questions as if they did not steal either object. They were told to lie only to the questions asked about the specific object they stole and to answer truthfully to the questions about the other object, the neutral and control questions. The subjects were told that, while they were answering the questions, a researcher would be watching their responses and trying to determine when they were lying. They were told that, if the researcher could not tell when they were lying, they would receive additional compensation (although every subject actually received the extra compensation). This provided an incentive for the subjects to lie successfully. After answering the deception questions, the subjects practiced a motor task. This task required the subjects to press their right thumb when they saw "Yes" and their right forefinger when they saw "No" on the IFIS screen. Then each subject was checked for metal and entered the scanner. The subjects were given earplugs, an IFIS glove was placed on their right hands and a pulse oximeter was placed on their left.

For the scanning, two BOLD fMRI paradigms (Motor and Deception) were run, as well as a structural scan. The BOLD fMRI covered the entire brain and was positioned with reference to the Anterior Commissure-Posterior Commissure line using a sagittal scout image. While the BOLD fMRI scans were acquired the subjects performed the motor task (6 minutes) and answered the deception questions (16 minutes, two eight minute blocks combined). After this, a 2 ½ minute high-resolution T1-weighted structural scan was performed to ensure there were no large artifacts or tumors.

After the MRI, each subject filled out a post-scanning questionnaire. Then the subjects were told the doctor could not tell when they were lying, and they received compensation for the scan and the screening.

Brain Activity Measurements.

Brain activity measurements are obtained by BOLD fMRI using a 3.0 T MRI scanner (e.g., Philips Intera 3 T) with a sensitivity encoding phased-array head coil (e.g., SENSE™ Head Coil, Philips Electronics, N.V., Amsterdam, Netherlands). The BOLD fMRI scans consist of 36 coplanar transverse slices (3.0 mm thick/0 mm gap) covering the entire brain and positioned 90° to the AC-PC line using a sagittal scout image. Each fMRI volume consists of BOLD weighted transverse scans and uses a single shot gradient EPI sequence (SENSE factor 2, flip angle=90°; TE 30.0 ms; TR 1867 ms; FOV 208×208; matrix 64×64 mm; in-plane resolution 3.25 mm×3.25 mm; through-plane resolution 3 mm). A set of 515 whole brain volumes are acquired for each paradigm. Following the BOLD fMRI, a structural T1 weighted scan is acquired to insure no major structural abnormalities.

Deception Testing Paradigm.

State and Trait Anxiety Inventory (STAI) scores were obtained from subjects before the fMRI. The STAI was used to determine whether the fMRI portion of the study caused a significant change in the subjects' anxiety reports. For the 20 state items, the subjects were asked to rate the intensity of their feelings of anxiety "right now, that is, at this moment" using the following scale: (1) not at all; (2) somewhat; (3) moderately so; (4) very much so. For the 20 trait items, the subjects were asked to rate the frequency of their feelings of anxiety in general. All anxiety-absent items were reverse scored. A paired-samples t-test was performed to determine whether there was a significant difference between the subjects' state and trait anxiety levels at baseline and at the time of scanning. Z scores were computed to determine whether or not the current sample differed from the normative sample of working adults ages 19-39.

Behavioral Data

Responses (thumb pressed for "Yes", index finger pressed for "No") and reaction times were acquired via the IFIS hand pad and the EPrime psychophysical recording software. Data were inspected to verify subject behavioral participation in both the motor and deception tasks and to screen for irregularities.

Functional MRI Data

Motor—Motor data were acquired to control for individual variability that may arise from scanner noise or differences in physiologic state. Image preprocessing was performed identical to preprocessing of the deception data. Statistical analysis was also similar to analysis for the deception task, with the exception that the motor paradigm is a block-design (alternating 12 seconds of thumb/finger presses with 12 seconds of rest, over the course of 6 minutes). It was hypothesized that activation should be seen in left motor/somatosensory cortical regions and in the right cerebellum.

Deception—All functional scans were transferred to a Dell Precision 650 running Red Hat Linux release 8.0 where the Statistical Parametric Mapping software (SPM 2, Wellcome Department of Cognitive Neurology, London, UK) was employed to analyze the data (run on Matlab version 6.5 Release 13.0.1). EPI scans were realigned and unwarped to correct head movements and resulting susceptibility distortions. After motion correction, all functional scans had residual motion less than 1 mm in any of the three planes and were thus included for further analysis. Slice timing was performed to correct for differences in slice acquisition time. Functional images were then spatially normalized to the SPM template and resampled with a voxel size of 3×3×3 mm Ashburner and Friston (1999)). After normalization, functional images were spatially smoothed using a Gaussian kernel with 8 mm full width at half maximum based on the suggested standard of 2 to 3 times the output spatially normalized voxel size. For creating individual t-maps, the event-related design was convolved with a hemodynamic response function that approximated the expected activation patterns. Effects at each voxel were estimated using the general linear model at the first statistical level. The motion-recorded parameters generated during the "realign" process were included as six user-specified regressors. A high pass filter (cut-off frequency=128s) was used to remove possible effects of low-frequency changes. Individual activated t-maps were generated by defining the following contrasts: Lie minus True, Lie minus Neutral, Lie minus Control, True minus Neutral, True minus Control, and Neutral minus Control. Individual deactivated t-maps were also created by defining the corresponding opposite contrasts: True minus Lie, Neutral minus Lie, Control minus Lie, Neutral minus True, Control minus True, and Control minus Neutral. Thirty individual contrast images generated at the first statistical level were then used to create group t-maps at the second level in a random effects model (Friston and Frackowiak (1997)) for each contrast. Cluster analyses were performed at the identical corrected threshold of $p<0.05$ (false discovery rate ("FDR")) for each group map with a spatial extent threshold of 20 voxels ($p<0.05$) to correct for multiple comparisons (Friston et al. (1994)). A program, "3dmerge," from Analysis of Functional Neuroimaging (AFNI, 2.56b) (Cox (1996)) was used to label each cluster based on sizes of clusters from each cluster mask. Another AFNI program, "3dcalc," was also used to separate each labeled cluster. Eleven Lie minus True clusters from the group analysis were thus individually separated in this way. The clusters defined by the group statement were used as region of interests (ROIs) on each of the 30 subject's individual t-maps. Thus, for each of these 11 ROIs, the number of activated voxels, averaged t-values, and standard deviations were extracted from all 30 individual t-maps of Lie minus True. The number of activated voxels, averaged t-values, and standard deviations for each subject for each cluster was used to build predictive models of which regions (based on clusters) would most likely differentiate lies from truth.

To determine which clusters were most likely to have the greatest predictive value, the number of subjects who had significant activation ($p<0.001$) in each cluster was determined for the contrast Lie minus True. The resulting data revealed that clusters 1 (20 subjects with significant voxels), 2 (16 subjects with significant voxels—4 unique from Cluster 1), and 4 (16 subjects with significant voxels—2 unique from Clusters 1 and 2), accounted for 26 subjects having a positive result (see Table 10). Thus, Clusters 1, 2 and 4 were used to determine number of activated voxels and mean t-values for each subject using the contrasts of Lie minus Control, True minus Control, Lie minus Neutral and True minus Neutral. A number of methods to determine sensitivity and specificity were performed.

Determination of Sensitivity and Specificity.

At the individual level, a number of methods were explored to provide a prediction of deception. Using the contrasts of Lie minus Control, True minus Control, Lie minus Neutral and True minus Neutral, the number of activated voxels and average t-values for each region (clusters 1, 2, 3, 4, 5, 6, and 7, see Table 6 for the definition) were generated for each subject at various thresholds ($p<0.05$, $p<0.01$, $p<0.005$, $p<0.001$, $p<0.0005$, and $p<0.0001$). Table 9 is a table of group analysis (n=30) of contrast Lie minus True with $p<0.05$ using FDR and cluster minimum of 20 voxels to correct for multiple comparisons. Anatomic regions highlighted by bold indicate brain areas that have replicated in all three Kozel et al. studies.

Two methods were explored to determine individual predictability of deception versus truth. Both methods were applied to the contrast of Lie and Truth with the Control (Control Comparisons) questions and Lie and Truth with the Neutral (Neutral Comparisons) questions.

Method 1—Subtraction Technique: Investigating the Neutral and Control Comparisons separately, one method took the number of activated voxels for each cluster (1, 2, 3, 4, 5, 6 and 7, see Table 6 for the definition) for the Lie contrasts and subtracted the number of activated voxels for the True contrasts. If the resulting value was positive, then it correctly identified a lie. If the resulting value was zero, then it was called indeterminate. If the resulting value was negative, then it was falsely identified as a truth. These numbers were calculated for the various probability thresholds. (See Table 8). Using this method, a sensitivity of 93% and specificity of 93% could be achieved looking only at cluster 1 using a threshold of $p<0.05$ for the Neutral Comparisons. If subjects with indeterminate results are not considered in the sensitivity/specificity analysis, then the method could achieve a sensitivity of 96% and a specificity of 96% with 10% unknown using Cluster 1 at $p<0.005$ for Neutral Comparison. This technique was also used for the average t-values instead of number of activated voxels with similar results. The (Lie-True) contrast was compared to the (True-Lie) contrast and it was similar results were obtained (Table 13).

Method 2—Threshold Technique: Analyzing the Neutral and Control Comparisons separately, it was determined whether subjects had a significant activation in Clusters 1, 2 and 4 at various thresholds ($p<0.05$, $p<0.01$, $p<0.005$, $p<0.001$, $p<0.0005$, and $p<0.0001$). For both the Lie and the Truth contrasts, if there was a significant voxel in the cluster(s) being considered, then it was considered an indication of a lie. Sensitivity and specificity values were generated considering various combinations of clusters (Clusters 1, 2 and 4 or Clusters 1 and 2 or Cluster 1). See Table 10. Using this method for the Neutral Comparison, a sensitivity of 80% and specificity of 47% was achieved including Clusters 1, 2 and 4 at the threshold of $p<0.0001$. Using Clusters 1 and 2, a sensitivity of 70% with a specificity of 60% was achieved at a threshold of $p<0.0001$.

Functional Magnetic Resonance Imaging Method.

The image data are analyzed with SPM 2 software, essentially as described above. An event model is designed for each subject using deceptive and truthful control responses convolved with the hemodynamic response function. For the verification paradigm, individual analysis is performed with four contrasts: Lie (deceptive control responses) minus Control (neutral control responses); Control minus Lie; True (truthful control responses) minus Control; and Control minus True. Significance is defined as $p<0.001$ with a cluster value of p-corrected $<0.05$. The MRIcro software is used to determine the anatomic location and Brodmann Areas for significant clusters of activation and the SPM2 functional map is superimposed on the Ti template skull stripped brain image in MRIcro.

Equivalents.

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize, or be able to ascertain using no more than routine experimentation, many equivalents to the specific embodiments of the invention described specifically herein. Such equivalents are intended to be encompassed in the scope of the appended claims.

REFERENCES

Adler et al. (2000), *Health Psychol.*, 19(6):586-592.
Alary et al. (2002), *NeuroImage*, 15(3):691-6.
American Polygraph Association (1996), *Polygraph: Issues and Answers*, American Polygraph Association, Severa Park, Md.
Annett (1970), *Brit. J. Psychol.*, 61:303-321.
Ashburner and Friston (1999), *Hum. Brain Mapp.* 7:254-266.
Babiloni et al. (2004), *NeuroImage*, 21(4):1576-84.
Binder et al. (1997), *J. Neurosci.*, 17:353-362.
Brodmann (1909), *Vergleichende Lokalisationslehre der Großhirnrinde*, Barth, Leipzig.
Bush et al. (1998), *Hum. Brain Mapp.*, 6:270-282.
Cohen et al. (1990), *Psychological Rev.*, 97:332-361.
Collins et al. (1994), *J. Comput. Assist. Tomogr.* 18:192-205.
Collins et al. (1998), *IEEE Trans. Med. Imag.* 17:463-468.
Cox (1996), *Comput. Biomed. Res.* 29:162-73.
Critchley et al. (2002), *NeuroImage*, 16:909-918.
Ekman et al. (1991), *J. Nonverbal Behav.* 15:125-135.
Elliott et al. (2000), *Neuroreport*, 11:1739-1744.
Farwell and Donchin (1991), *Psychophysiol.*, 28:531-547.
Feng et al. (2004), *NeuroImage* 22:443-446.
Fernandez et al. (2001), *NeuroImage*, 14:585-94.
First et al. (1995), *Structured Clinical Interview for DSM-IV (SCID)*, American Psychiatric Press, Washington, D.C.
Friston et al. (1994), *Hum. Brain Mapp.* 1:210-220.
Friston et al. (1995), *Hum. Brain Mapp.* 2:189-210.
Friston and Frackowiak (1997), *Human Brain Function*. San Diego, Calif.: Academic Press:487-517.
Furedy (1986), in *Psychophysiology Systems, Processes and Applications—A handbook*, Coles, Donchin and Porges (Eds.), Guilford Press, New York, pp. 683-700.
Ganis et al. (2003), *Cerebral Cortex*, 13:830-836.
George et al. (1997), *J. Neuropsychiatry Clin. Neurosci.*, 9:55-63.
Graham (1999), *MMPI-2: Assessing Personality and Psychopathology*. 3rd ed., Oxford University Press, New York.
Kozel et al. (2003), *Hum. Brain Mapp.*, 19:S33 (Abstract #455).
Kozel et al. (2004a), *J. Neuropsychiatry Clin. Neurosci.*, 16:295-305.
Kozel et al. (2004b), *Behav. Neurosci.*, 118:852-6.
Lancaster et al. (1997), *Hum. Brain Mapp.*, 5:238-242.
Langleben et al. (2002), *NeuroImage*, 15(3):727-732.
Lee et al. (2002), *Hum. Brain Mapp.*, 15(3):157-164.
Lorberbaum et al. (1999), *Depression and Anxiety*, 10:99-104
Lubow and Fein (1996), *J. Exp. Psychol.: Applied*, 2:164-177.
MacDonald et al. (2000), *Science*, 288:1835-8
Martin (2003), *Neuroanatomy Text and Atlas*, 3rd ed., McGraw-Hill, New York.
McGonigle et al. (2000), *NeuroImage*, 11:708-734.
Moule et al. (2003) *Proc. Natl. Acad. Sci. (USA)* 100 (16): 9122-7.
Noguchi et al. (2003), *NeuroImage*, 19(1):156-162
O'Doherty et al. (2001), *Nature Neurosci.*, 4(1):95-102.
Ogawa et al. (1990), *Proc. Natl. Acad. Sci. (USA)*, 87(24): 9868-9872.
Oldfield (1971), *Neuropsychologia*, 9:97-113.
Pardo et al. (1991), *Nature* 349:61-64.
Pavlidis et al. (2002), *Nature* 415:35.
Rain et al. (2000), *Arch. Gen. Psychiatry*, 57:119-127.
Rauch and Savage (1997), *Psychiatric Clin. N. Amer.*, 20:741-768.
Rorden and Brett (2000), *Behavioural Neurology*, 12:191-200.
Samuel et al. (1998). *Neurology* 51: 1567-1575.
Shastri et al. (2001), *J. Magnet. Reson. Imaging*, 14:187-193.
Sheehan and Statham (1988), *Brit. J. Exper. Clin. Hypnosis*, 5:87-94.
Spence et al. (2001a), *NeuroImage* 13:Abstract #S477.
Spence et al. (2001b), *Neuroreport*, 12(13):2849-53.
Spielberger et al. (1983), *Manual for the State-Trait Anxiety Inventor*. Redwood City, Calif.: Mind Garden, Inc.
Sporer (1997), *Applied Cog. Psychol.*, 11:373-397.
Steenhuis and Bryden (1989), *Cortex*, 25:289-304.
Sugiura et al. (2001), *Soc. Neurosci.* 31$^{st}$ *Ann. Mtg.*, Abstract #80.5.
Taga et al. (2003), *Proc. Natl. Acad. Sci. (USA)*, 100(19): 10722-7.
Talairach and Tournox (1988), *Co-Planar Stereotaxic Atlas of the Human Brain*, Georg Thieme Verlag, Stuttgart.
Tardif et al. (2000), *Intl. J. Psychophysiology*, 36:1-9.
Taylor et al. (1997), *NeuroImage*, 6(2):81-92.
Thompson et al. (1996), *J. Neurosci.*, 16: 4261-4274.
Turner et al. (2003), *NeuroImage*, 19(3):1145-62.
Tzourio-Mazoyer et al. (2002), *NeuroImage*, 15:273-89.
van Honk et al. (2001), *Arch. Gen. Psychiatry*, 58:973-974.
Wicker et al. (1998), *NeuroImage*, 8(2):221-7.
Wiley (1998), *Psychiatric Clin. N. Amer.*, 21:870-893.
Yankee (1995), *J. Forensic Sci.*, 40:63-68.

TABLE 5

Subject Demographics and Behavioural Results

| Demographics | Model-Building | Model-Testing | Significance |
| --- | --- | --- | --- |
| Screened/Scanned/Imaged | 34/31/30 | 32/31/31 | $X^2 = 0.07, p = 0.97$ |
| Sex (M/F) | 17/13 | 12/19 | $X^2 = 2.0, p = 0.16$ |
| Mean Age (SD, range) | 30.4 yrs (±8.3, 19-50) | 33.4 yrs (±9.7, 18-50) | $t = 1.3, p = 0.20$ |
| Handedness (R/L/Mixed) | 28/1/1 | 24/3/3 | $X^2 = 2.3, p = 0.32$ |
| Ethnicity (AA/A/C) | 6/1/23 | 12/2/17 | $X^2 = 3.2, p = 0.20$ |

TABLE 5-continued

Subject Demographics and Behavioural Results

| Demographics | Model-Building | Model-Testing | Significance |
|---|---|---|---|
| Employment (FT/PT/U/S) | 21/3/1/5 | 24/1/0/6 | $X^2 = 1.9, p = 0.52$ |
| Mean Education (SD, range) | 16.2 yrs (±2.5, 12-20) | 16.3 yrs (±2.5, 12-21) | $t = 0.16, p = 0.88$ |

Behavioural Results

| | Model-Building | Model-Testing | Significance |
|---|---|---|---|
| Object Taken (ring/watch) | 16/14 | 15/16 | $X^2 = 0.15, p = 0.70$ |
| Mean Percent Questions Responded Per Protocol (SD, range) | 96.7% (±2.5, 89.5-100) | 96.1% (±3.4, 83.8-100) | $t = 0.7: p = 0.50$ |
| Average Subject Reaction Time for Questions Responded Per Protocol | | | |
| Deceptive Mean (SD, range) | 712 ms (±135, 459-988) | 750 (±189, 457-1213) | $t = 0.9, p = 0.4$ |
| Truthful Mean (SD, range) | 747 ms (±161, 452-1067) | 773 (±206, 474-1308) | $t = 0.6, p = 0.6$ |
| Control Mean (SD, range) | 722 ms (±137, 461-1015) | 744 (±185, 490-1188) | $t = 0.5, p = 0.6$ |
| Neutral Mean (SD, range) | 673 ms (±123, 425-938) | 710 (±169, 449-1011) | $t = 1.0, p = 0.3$ |
| Statistical Significance of Average Subject Reaction Time for Deceptive versus Truthful Responses | $t = 0.9, p = 0.4$ | $t = 0.4, p = 0.6$ | |

Significance = testing the statistical difference between Model-Testing Group and Model-Building Group.
M = Male,
F = Female,
SD = Standard Deviation,
R = Right,
L = Left,
AA = African-American,
A = Asian,
C = Caucasian,
FT = Full Time,
PT = Part Time,
U = Unemployed,
S = Student,
Screen = Day of Screening,
Scan = Day of MRI Scanning,
t = Student t-test, two-tailed

TABLE 6

Group Analysis of Lie-minus-True Model-Building Group (n = 30)
Statistical Threshold is False Discovery Rate $p < 0.05, k > 25$

| Cluster | k | Complete Anatomic Area of Cluster | MNI Coordinates of Voxel with Largest t-value | Anatomic Location of Voxel with Largest t-value | Brodmann's Area of Voxel with Largest t-value |
|---|---|---|---|---|---|
| 1 | 327 | R Anterior Cingulate* | −3, 21, 48 | L supplementary motor area | 8 |
| | | L Anterior Cingulate | 9, 18, 42 | R cingulate | 32 |
| | | R Middle Cingulate | 9, −3, 66 | R supplementary motor area | 6 |
| | | R Superior Medial Frontal | | | |
| | | L Superior Medial Frontal | | | |
| | | R Supplementary Motor Area | | | |
| 2 | 271 | R Orbitofrontal* | 36, 27, 0 | R insula | 47 |
| | | R Inferior Frontal* | 48, 15, −9 | R insula | 38 |
| | | R Insula | 51, 24, −6 | R orbitofrontal | 38 |
| | | R Superior Temporal Pole | | | |
| 3 | 231 | R Olfactory | −9, −3, 6 | L thalamus | N/A |
| | | R Caudate | 12, 0, 9 | R internal capsule | N/A |
| | | R Putamen | 12, 3, −3 | R pallidum | N/A |
| | | R Pallidum | | | |
| | | L Pallidum | | | |
| | | L Caudate | | | |
| | | R Thalamus | | | |
| | | L Thalamus | | | |
| 4 | 140 | R Middle Frontal* | 27, 51, 33 | R middle frontal | 46 |
| | | R Superior Frontal | 36, 42, 21 | R middle frontal | 46 |
| | | | 33, 45, 33 | R middle frontal | 46 |
| 5 | 39 | R Middle Temporal | 60, −45, 21 | R superior temporal | 42 |
| | | R Superior Temporal | 66, −48, 12 | R middle temporal | 22 |
| | | R Supramarginal | | | |
| | | R Angular | | | |
| 6 | 35 | L Middle Temporal* | −57, −42, 30 | L supramarginal | 48 |
| | | L Superior Temporal | −57, −51, 39 | L inferior parietal | 40 |
| | | L Supramarginal | | | |
| | | L Inferior Parietal | | | |

TABLE 6-continued

Group Analysis of Lie-minus-True Model-Building Group (n = 30)
Statistical Threshold is False Discovery Rate p < 0.05, k > 25

| Cluster | k | Complete Anatomic Area of Cluster | MNI Coordinates of Voxel with Largest t-value | Anatomic Location of Voxel with Largest t-value | Brodmann's Area of Voxel with Largest t-value |
|---|---|---|---|---|---|
| 7 | 27 | L Putamen | −30, 12, 9 | L insula | 48 |
|   |    | L Insula  | −30, 21, 6 | L insula | 48 |

*Regions indicate brain areas of significant activations replicated from prior two studies.
R—Right,
L—Left,
k = minimum number of voxels in cluster

TABLE 7

Group Analysis of Lie-minus-True Model-Testing Group (n = 31)

| Cluster | k | Complete Anatomic Area of Cluster | MNI Coordinates of Voxel with Largest t-value | Anatomic Location of Voxel with Largest t-value | Brodmann's Area of Voxel with Largest t-value |
|---|---|---|---|---|---|
| 1 | 1020 | R Anterior Cingulate* | 3, 16, 60 | R supplementary motor area | 6 |
|   |      | R Middle Frontal* | 15, 36, 21 | R anterior cingulate | 32 |
|   |      | R Superior Frontal | 15, 21, 66 | R supplementary motor area | 8 |
|   |      | L Middle Frontal | | | |
|   |      | L Superior Frontal | | | |
|   |      | R Superior Medial Frontal | | | |
|   |      | L Superior Medial Frontal | | | |
|   |      | L Anterior Cingulate | | | |
|   |      | L Supplementary Motor Area | | | |
|   |      | R Supplementary Motor Area | | | |
| 2 | 598 | R Orbitofrontal* | 45, 39, −6 | R orbitofrontal | 47 |
|   |     | R Inferior Frontal* | 42, 24, −9 | R insula | 47 |
|   |     | R Middle Frontal* | 57, 15, 12 | R inferior frontal | 44 |
|   |     | R Superior Temporal Pole | | | |
|   |     | R Insula | | | |
| 3 | 187 | L Orbitofrontal | −45, 36, −6 | L orbitofrontal | 47 |
|   |     | L Inferior Frontal | −36, 42, −12 | L orbitofrontal | 47 |
|   |     | L Middle Frontal | −51, 21, −3 | L orbitofrontal | 38 |
|   |     | L Superior Temporal Pole | | | |
|   |     | L Insula | | | |
| 4 | 186 | L Middle Temporal* | −57, −51, 33 | L angular | 40 |
|   |     | L Supramarginal | −48, −54, 33 | L angular | 39 |
|   |     | L Superior Temporal | | | |
|   |     | L Angular | | | |
|   |     | L Inferior Parietal | | | |
| 5 | 108 | R Middle Temporal | 60, −54, 33 | R angular | 40 |
|   |     | R Supramarginal | | | |
|   |     | R Superior Temporal | | | |
|   |     | R Angular | | | |
|   |     | R Inferior Parietal | | | |
| 6 | 99 | L Pallidum | −12, 9, 6 | L caudate | N/A |
|   |    | L Caudate | | | |
|   |    | L Putamen | | | |
|   |    | L Thalamus | | | |
| 7 | 49 | R Pallidum | 12, 6, 9 | R caudate | N/A |
|   |    | R Caudate | | | |
|   |    | R Putamen | | | |
|   |    | R Thalamus | | | |

Statistical Threshold is False Discovery Rate p < 0.05, k > 25
*Regions indicate brain areas of significant activations replicated from prior two studies.
R—Right,
L—Left,
k = minimum number of voxels in cluster

TABLE 8

Subtraction Technique - Voxels

MODEL BUILDING-GROUP

| Contrast | 1-N | 0-N | | | 1-N | 0-N | | | 1-N | 0-N | |
|---|---|---|---|---|---|---|---|---|---|---|---|
| Cluster | 1 | 1 | | | 2 | 2 | | | 4 | 4 | |
| p-Value | P0.05 | P0.05 | | | P0.05 | P0.05 | | | P0.05 | P0.05 | |
| Subject | No. Voxels | No. Voxels | Lie – True | Normalized | No. Voxels | No. Voxels | Lie – True | Normalized | No. Voxels | No. Voxels | Lie – True |
| AKM | 143 | 233 | 90 | 0.13513514 | 43 | 187 | 144 | 0.23529412 | 5 | 41 | 36 |
| ALS | 53 | 105 | 52 | 0.07807808 | 32 | 240 | 208 | 0.33986928 | 19 | 76 | 57 |
| AMD | 0 | 308 | 308 | 0.46246246 | 0 | 178 | 178 | 0.29084967 | 0 | 76 | 76 |
| ARG | 0 | 3 | 3 | 0.0045045 | 0 | 75 | 75 | 0.12254902 | 0 | 6 | 6 |
| ASF | 0 | 1 | 1 | 0.0015015 | 0 | 43 | 43 | 0.07026144 | 0 | 0 | 0 |
| BJM | 14 | 8 | | | 22 | 18 | | | 1 | 9 | 8 |
| BVM | 55 | 147 | 92 | 0.13813814 | 69 | 135 | 66 | 0.10784314 | 0 | 38 | 38 |
| CAP | 29 | 65 | 36 | 0.05405405 | 17 | 0 | | | 58 | 58 | 0 |
| CMB | 30 | 125 | 95 | 0.14264264 | 15 | 96 | 81 | 0.13235294 | 70 | 43 | |
| CRJ | 0 | 38 | 38 | 0.05705706 | 1 | 138 | 137 | 0.22385621 | 0 | 0 | 0 |
| DCM | 73 | 181 | 108 | 0.16216216 | 148 | 195 | 47 | 0.07679739 | 37 | 30 | |
| DLR | 81 | 199 | 118 | 0.17717718 | 30 | 49 | 19 | 0.03104575 | 0 | 21 | 21 |
| DMH | 198 | 218 | 20 | 0.03003003 | 113 | 176 | 63 | 0.10294118 | 59 | 102 | 43 |
| EBW | 20 | 285 | 265 | 0.3978979 | 13 | 133 | 120 | 0.19607843 | 37 | 116 | 79 |
| ERB | 301 | 329 | 28 | 0.04204204 | 249 | 241 | | | 88 | 140 | 52 |
| KTM | 61 | 140 | 79 | 0.11861862 | 60 | 86 | 26 | 0.04248366 | 53 | 92 | 39 |
| KWW | 0 | 125 | 125 | 0.18768769 | 3 | 51 | 48 | 0.07843137 | 3 | 102 | 99 |
| LPF | 36 | 180 | 144 | 0.21621622 | 43 | 78 | 35 | 0.05718954 | 4 | 37 | 33 |
| MKS | 231 | 321 | 90 | 0.13513514 | 95 | 217 | 122 | 0.19934641 | 128 | 158 | 30 |
| MLW | 159 | 326 | 167 | 0.25075075 | 195 | 278 | 83 | 0.13562092 | 89 | 126 | 37 |
| MSW | 177 | 222 | 45 | 0.06756757 | 211 | 229 | 18 | 0.02941176 | 87 | 138 | 51 |
| NDP | 118 | 240 | 122 | 0.18318318 | 147 | 269 | 122 | 0.19934641 | 7 | 42 | 35 |
| PJK | 277 | 328 | 51 | 0.07657658 | 267 | 294 | 27 | 0.04411765 | 125 | 152 | 27 |
| QLB | 31 | 89 | 58 | 0.08708709 | 9 | 47 | 38 | 0.0620915 | 0 | 26 | 26 |
| RJA | 85 | 240 | 155 | 0.23273273 | 21 | 109 | 88 | 0.14379085 | 43 | 66 | 23 |
| SMJ | 239 | 23 | | | 29 | 54 | 25 | 0.04084967 | 85 | 50 | |
| SRB | 77 | 194 | 117 | 0.17567568 | 109 | 109 | 0 | | 64 | 97 | 33 |
| SWS | 32 | 141 | 109 | 0.16366366 | 44 | 58 | 14 | 0.02287582 | 33 | 97 | 64 |
| VRC | 150 | 260 | 110 | 0.16516517 | 41 | 184 | 143 | 0.23366013 | 0 | 27 | 27 |
| WCB | 180 | 230 | 50 | 0.07507508 | 98 | 85 | | | 35 | 55 | 20 |

MODEL TESTING-GROUP

| Contrast | 1-N | 0-N | | | 1-N | 0-N | | | 1-N | 0-N | |
|---|---|---|---|---|---|---|---|---|---|---|---|
| Cluster | 1 | 1 | | | 2 | 2 | | | 4 | 4 | |
| p-Value | P0.05 | P0.05 | | | P0.05 | P0.05 | | | P0.05 | P0.05 | |
| Subject | No. Voxels | No. Voxels | Lie – True | Normalized | No. Voxels | No. Voxels | Lie – True | Normalized | No. Voxels | No. Voxels | Lie – True |
| 1 | 310 | 112 | 198 | 0.2972973 | 289 | 67 | 222 | 0.3627451 | 149 | 3 | 146 |
| 2 | 272 | 0 | 272 | 0.40840841 | 159 | 2 | 157 | 0.25653595 | 103 | 1 | 102 |
| 3 | 308 | 165 | 143 | 0.21471471 | 256 | 67 | 189 | 0.30882353 | 148 | 102 | 46 |
| 4 | 318 | 143 | 175 | 0.26276276 | 301 | 141 | 160 | 0.26143791 | 100 | 73 | 27 |
| 5 | 304 | 267 | 37 | 0.05555556 | 276 | 249 | 27 | 0.04411765 | 148 | 115 | 33 |

| | | Cluster | | | | | | |
|---|---|---|---|---|---|---|---|---|
| | | 1 | | 2 | | 4 | | |
| Model Building Group Each Cluster | TRUE | 28 | 93% | TRUE | 25 | 83% | TRUE | 24 | 80% |
| | FALSE | 2 | 93% | FALSE | 4 | 87% | FALSE | 3 | 90% |
| | UNKNOWN | 0 | 0% | UNKNOWN | 1 | 3% | UNKNOWN | 3 | 10% |
| | TOTAL | 30 | | TOTAL | 30 | | TOTAL | 30 | |
| | | n | % | | n | % | | n | % |
| Model Testing Group Each Cluster | TRUE | 25 | 83% | TRUE | 26 | 84% | TRUE | 25 | 81% |
| | FALSE | 5 | 83% | FALSE | 5 | 84% | FALSE | 6 | 81% |
| | UNKNOWN | 1 | 3% | UNKNOWN | 0 | 0% | UNKNOWN | 0 | 0% |
| | TOTAL | 30 | | TOTAL | 31 | | TOTAL | 31 | |
| Model Building Group Each Cluster | TRUE | 25 | 83% | TRUE | 26 | 84% | TRUE | 25 | 81% |
| | FALSE | 5 | 83% | FALSE | 5 | 84% | FALSE | 6 | 81% |
| | UNKNOWN | 1 | 3% | UNKNOWN | 0 | 0% | UNKNOWN | 0 | 0% |
| | TOTAL | 30 | | TOTAL | 31 | | TOTAL | 31 | |

TABLE 8-continued

Subtraction Technique - Voxels

| | | | | | | | | | |
|---|---|---|---|---|---|---|---|---|---|
| Model Testing Group | TRUE | 20 | 87% | TRUE | 20 | 87% | TRUE | 21 | 88% |
| Each Cluster | FALSE | 3 | 87% | FALSE | 3 | 87% | FALSE | 3 | 88% |
| | UNKNOWN | 1 | 4% | UNKNOWN | 1 | 4% | UNKNOWN | 0 | 0% |
| | TOTAL | 23 | | TOTAL | 23 | | TOTAL | 24 | |
| Model Building Group | TRUE | 25 | 83% | TRUE | 26 | 84% | TRUE | 25 | 81% |
| Each Cluster | FALSE | 5 | 83% | FALSE | 5 | 84% | FALSE | 6 | 81% |
| Model Testing Group | UNKNOWN | 1 | 3% | UNKNOWN | 0 | 0% | UNKNOWN | 0 | 0% |
| Each Cluster | TOTAL | 30 | | TOTAL | 31 | | TOTAL | 31 | |
| Model Building Group | TRUE | 23 | 88% | TRUE | 22 | 88% | TRUE | 23 | 92% |
| Each Cluster | FALSE | 3 | 88% | FALSE | 3 | 88% | FALSE | 2 | 92% |
| | UNKNOWN | 1 | 4% | UNKNOWN | 2 | 8% | UNKNOWN | 2 | 8% |
| | TOTAL | 26 | | TOTAL | 25 | | TOTAL | 25 | |

TABLE 9

Voxel Subtraction Method Using Lie – True
Clusters 1, 2, 3, 4, 5, 6 and 7 as defined in Table 6

| Subject | Cluster1 P1 Mean_T | Cluster1 P1 No. Voxels | Cluster1 P1 SD | Cluster1 P0.05 Mean_T | Cluster1 P0.05 No. Voxels | Cluster1 P0.05 SD | Cluster1 P0.01 Mean_T | Cluster1 P0.01 No. Voxels | Cluster1 P0.01 SD | Cluster1 P0.005 Mean_T | Cluster1 P0.005 No. Voxels |
|---|---|---|---|---|---|---|---|---|---|---|---|
| AKM | 1.045112 | 333 | 0.899593 | 2.41086 | 69 | 0.591059 | 2.939856 | 33 | 0.399343 | 3.065539 | 27 |
| ALS | 1.104946 | 333 | 0.961192 | 2.346237 | 94 | 0.498367 | 2.815301 | 41 | 0.353546 | 2.9862 | 28 |
| AMD | 4.156535 | 333 | 1.167217 | 4.231534 | 325 | 1.075718 | 4.307217 | 314 | 1.014713 | 4.386121 | 301 |
| ARG | 0.540944 | 333 | 0.51805 | 1.793187 | 9 | 0.098872 | | | | | |
| ASF | −0.06029 | 333 | 0.64835 | 1.895157 | 1 | 1E+30 | | | | | |
| BJM | 0.618533 | 333 | 1.129742 | 2.205745 | 71 | 0.395721 | 2.647699 | 25 | 0.276622 | 2.877921 | 12 |
| BVM | 0.702765 | 333 | 0.936765 | 2.281654 | 53 | 0.464195 | 2.798532 | 20 | 0.242724 | 2.903278 | 15 |
| CAP | 0.343679 | 333 | 0.636765 | 1.838448 | 8 | 0.12654 | | | | | |
| CMB | 0.666172 | 333 | 1.014858 | 2.202194 | 61 | 0.349936 | 2.599899 | 21 | 0.202378 | 2.813142 | 9 |
| CRJ | 2.123771 | 333 | 0.817741 | 2.516362 | 237 | 0.58314 | 2.955981 | 127 | 0.428215 | 3.102688 | 98 |
| DCM | 0.627256 | 333 | 0.73555 | 2.274154 | 20 | 0.623585 | 2.890716 | 8 | 0.524446 | 3.316044 | 4 |
| DLR | 0.931316 | 333 | 0.959339 | 2.363436 | 74 | 0.482889 | 2.761542 | 39 | 0.268152 | 2.905685 | 26 |
| DMH | 0.56813 | 333 | 1.063037 | 2.175225 | 51 | 0.396302 | 2.7015 | 14 | 0.316019 | 2.969023 | 7 |
| EBW | 2.510804 | 333 | 1.278711 | 3.062289 | 230 | 1.159356 | 3.709116 | 144 | 1.001783 | 3.932885 | 122 |
| ERB | 1.146497 | 333 | 0.731889 | 2.086044 | 83 | 0.293118 | 2.49868 | 21 | 0.113992 | 2.667428 | 4 |
| KTM | 0.872957 | 333 | 1.065585 | 2.014548 | 87 | 0.276327 | 2.526115 | 14 | 0.149371 | 2.663781 | 7 |
| KWW | 1.683025 | 333 | 0.775415 | 2.279454 | 174 | 0.427507 | 2.720574 | 69 | 0.284415 | 2.893576 | 41 |
| LPF | 1.190339 | 333 | 0.96614 | 2.150549 | 125 | 0.37791 | 2.655862 | 35 | 0.260989 | 2.805961 | 21 |
| MKS | 1.433943 | 333 | 1.082771 | 2.628146 | 117 | 0.684027 | 3.118459 | 66 | 0.497667 | 3.257388 | 54 |
| MLW | 1.71761 | 333 | 0.734317 | 2.2933 | 170 | 0.476127 | 2.782487 | 66 | 0.374221 | 2.960518 | 44 |
| MSW | 0.614518 | 333 | 0.906634 | 2.276461 | 33 | 0.388858 | 2.672397 | 14 | 0.189961 | 2.791801 | 9 |
| NDP | 0.927054 | 333 | 1.02487 | 2.241 | 95 | 0.452677 | 2.742276 | 35 | 0.291807 | 2.910938 | 22 |
| PJK | 1.191083 | 333 | 0.776761 | 2.239354 | 86 | 0.506865 | 2.877714 | 28 | 0.3439 | 3.012685 | 21 |
| QLB | 0.684655 | 333 | 0.963813 | 2.23223 | 57 | 0.45954 | 2.710697 | 22 | 0.330212 | 2.922358 | 12 |
| RJA | 1.423027 | 333 | 0.726265 | 2.10385 | 135 | 0.332784 | 2.569153 | 34 | 0.195419 | 2.759194 | 14 |
| SMJ | −1.704493 | 333 | 0.709732 | | | | | | | | |
| SRB | 1.321325 | 333 | 1.15787 | 2.484822 | 130 | 0.623652 | 2.92072 | 73 | 0.478728 | 3.194832 | 45 |
| SWS | 1.211409 | 333 | 1.104749 | 2.333522 | 125 | 0.475016 | 2.775506 | 56 | 0.327638 | 2.971011 | 34 |
| VRC | 1.361626 | 333 | 0.880754 | 2.241679 | 129 | 0.390968 | 2.646951 | 52 | 0.231228 | 2.849906 | 25 |
| WCB | 0.237146 | 333 | 0.900554 | 1.987427 | 13 | 0.300616 | 2.556302 | 2 | 0.317395 | 2.780734 | 1 |
| 0.05 | 5 | | | 29 | | | 26 | | | 26 | |
| 0.025 | 3 | | | 25 | | | 25 | | | 25 | |
| 0.01 | 2 | | | 7 | | | 24 | | | 24 | |
| 0.005 | 0 | | | 2 | | | 19 | | | 23 | |

| Subject | Cluster1 P0.005 SD | Cluster1 P0.001 Mean_T | Cluster1 P0.001 No. Voxels | Cluster1 P0.001 SD | Cluster1 P0.0005 Mean_T | Cluster1 P0.0005 No. Voxels | Cluster1 P0.0005 SD | Cluster1 P0.0001 Mean_T | Cluster1 P0.0001 No. Voxels | Cluster1 P0.0001 SD | Cluster2 P1 Mean_T |
|---|---|---|---|---|---|---|---|---|---|---|---|
| AKM | 0.328477 | 3.404334 | 11 | 0.188619 | 3.534828 | 7 | 0.092606 | | | | 1.79374 |
| ALS | 0.29667 | 3.328748 | 10 | 0.15338 | 3.433509 | 6 | 0.100693 | | | | 1.884652 |
| AMD | 0.960967 | 4.531022 | 275 | 0.875008 | 4.629174 | 256 | 0.826292 | 4.80471 | 221 | 0.750834 | 3.771539 |
| ARG | | | | | | | | | | | 1.033464 |
| ASF | | | | | | | | | | | 1.477017 |
| BJM | 0.22958 | 3.202912 | 3 | 0.036983 | | | | | | | 0.473609 |
| BVM | 0.183002 | 3.177068 | 3 | 0.028557 | | | | | | | 0.779257 |
| CAP | | | | | | | | | | | 0.233351 |
| CMB | 0.093806 | | | | | | | | | | 1.3009 |
| CRJ | 0.376911 | 3.472888 | 41 | 0.262108 | 3.649221 | 25 | 0.17559 | 3.887378 | 7 | 0.081567 | 2.252034 |
| DCM | 0.431351 | 3.693733 | 2 | 0.340162 | 3.693733 | 2 | 0.340162 | 3.934264 | 1 | 1E+30 | 0.202914 |

TABLE 9-continued

Voxel Subtraction Method Using Lie − True
Clusters 1, 2, 3, 4, 5, 6 and 7 as defined in Table 6

| | | | | | | | | | | |
|---|---|---|---|---|---|---|---|---|---|---|
| DLR | 0.207159 | 3.246811 | 5 | 0.068189 | 3.35456 | 1 | 1E+30 | | | 0.509161 |
| DMH | 0.225591 | 3.231095 | 2 | 0.103434 | | | | | | 0.891299 |
| EBW | 0.924888 | 4.271715 | 93 | 0.796532 | 4.399269 | 83 | 0.747824 | 4.630241 | 66 | 0.662432 | 2.215695 |
| ERB | 0.080221 | | | | | | | | | 0.366049 |
| KTM | 0.067301 | | | | | | | | | 0.508287 |
| KWW | 0.241553 | 3.286913 | 8 | 0.123074 | 3.475944 | 2 | 0.046352 | | | | 0.717543 |
| LPF | 0.231908 | 3.337104 | 2 | 0.145306 | 3.439851 | 1 | 1E+30 | | | | 0.528765 |
| MKS | 0.442159 | 3.593285 | 30 | 0.28274 | 3.692789 | 24 | 0.223489 | 3.88194 | 12 | 0.103795 | 1.235026 |
| MLW | 0.335894 | 3.379578 | 14 | 0.230909 | 3.588233 | 7 | 0.127229 | | | | 1.263474 |
| MSW | 0.12465 | | | | | | | | | | 0.439591 |
| NDP | 0.235307 | 3.305199 | 4 | 0.1844 | 3.605814 | 1 | 1E+30 | | | | 1.558917 |
| PJK | 0.290356 | 3.426636 | 5 | 0.248117 | 3.626755 | 3 | 0.049835 | | | | 0.782803 |
| QLB | 0.312458 | 3.556056 | 2 | 0.04797 | 3.556056 | 2 | 0.04797 | | | | 0.831965 |
| RJA | 0.14582 | | | | | | | | | | 0.847224 |
| SMJ | | | | | | | | | | | 0.080486 |
| SRB | 0.415071 | 3.556093 | 21 | 0.311718 | 3.692535 | 15 | 0.261989 | 3.993061 | 5 | 0.207729 | −0.141422 |
| SWS | 0.276467 | 3.414881 | 7 | 0.176155 | 3.476648 | 5 | 0.168248 | 3.794171 | 1 | 1E+30 | 0.151519 |
| VRC | 0.15617 | 3.211592 | 1 | 1E+30 | | | | | | | 1.646863 |
| WCB | 1E+30 | | | | | | | | | | −0.150562 |
| 0.05 | | 20 | | | 16 | | | 7 | | | 6 |
| 0.025 | | 19 | | | 15 | | | 7 | | | 3 |
| 0.01 | | 18 | | | 14 | | | 7 | | | 1 |
| 0.005 | | 17 | | | 13 | | | 6 | | | 0 |

| Subject | Cluster2 P1 No. Voxels | Cluster2 P1 SD | Cluster2 P0.05 Mean_T | Cluster2 P0.05 No. Voxels | Cluster2 P0.05 SD | Cluster2 P0.01 Mean_T | Cluster2 P0.01 No. Voxels | Cluster2 P0.01 SD | Cluster2 P0.005 Mean_T | Cluster2 P0.005 No. Voxels | Cluster2 P0.005 SD |
|---|---|---|---|---|---|---|---|---|---|---|---|
| AKM | 306 | 1.016918 | 2.427689 | 190 | 0.589276 | 2.953579 | 87 | 0.454912 | 3.103553 | 67 | 0.411215 |
| ALS | 306 | 0.866856 | 2.412556 | 179 | 0.700164 | 2.974672 | 78 | 0.716254 | 3.24867 | 51 | 0.751357 |
| AMD | 306 | 1.861706 | 4.305533 | 259 | 1.483142 | 4.674806 | 223 | 1.251745 | 4.799026 | 211 | 1.17003 |
| ARG | 306 | 0.839704 | 2.068455 | 78 | 0.337563 | 2.644686 | 14 | 0.162766 | 2.791431 | 7 | 0.096229 |
| ASF | 306 | 0.915368 | 2.305513 | 136 | 0.469606 | 2.750272 | 62 | 0.280678 | 2.901105 | 41 | 0.2218 |
| BJM | 306 | 1.230687 | 2.533685 | 47 | 0.566277 | 2.947625 | 27 | 0.364083 | 3.092742 | 21 | 0.272494 |
| BVM | 306 | 0.97285 | 2.112001 | 61 | 0.33721 | 2.625435 | 14 | 0.123898 | 2.680851 | 10 | 0.098112 |
| CAP | 306 | 0.973012 | 1.842714 | 9 | 0.160605 | | | | | | |
| CMB | 306 | 1.065339 | 2.318463 | 124 | 0.533732 | 2.873149 | 48 | 0.423097 | 3.09539 | 32 | 0.342892 |
| CRJ | 306 | 0.919546 | 2.679154 | 223 | 0.655549 | 3.038567 | 147 | 0.498341 | 3.201393 | 116 | 0.433297 |
| DCM | 306 | 0.77911 | 1.936137 | 8 | 0.132107 | | | | | | |
| DLR | 306 | 1.109772 | 2.075827 | 27 | 0.273884 | 2.450582 | 7 | 0.085677 | | | |
| DMH | 306 | 1.034246 | 2.046509 | 79 | 0.29145 | 2.552888 | 13 | 0.15049 | 2.703639 | 5 | 0.125851 |
| EBW | 306 | 1.104784 | 2.79892 | 207 | 0.784311 | 3.272361 | 131 | 0.582581 | 3.376856 | 116 | 0.535887 |
| ERB | 306 | 1.159728 | 2.098857 | 47 | 0.394249 | 2.742516 | 10 | 0.279889 | 2.921097 | 6 | 0.215777 |
| KTM | 306 | 0.602732 | 2.277954 | 28 | 0.442744 | 2.775442 | 10 | 0.255016 | 2.890674 | 7 | 0.219086 |
| KWW | 306 | 1.417701 | 2.363641 | 95 | 0.509934 | 2.783119 | 46 | 0.405584 | 3.08736 | 24 | 0.340098 |
| LPF | 306 | 0.955523 | 2.231622 | 38 | 0.429004 | 2.749259 | 13 | 0.282341 | 2.890658 | 9 | 0.216606 |
| MKS | 306 | 0.712784 | 1.985054 | 99 | 0.24933 | 2.460382 | 12 | 0.130435 | 2.830825 | 1 | 1E+30 |
| MLW | 306 | 0.67888 | 1.950563 | 89 | 0.288463 | 2.556955 | 10 | 0.125687 | 2.673899 | 5 | 0.040218 |
| MSW | 306 | 0.963699 | 1.98075 | 35 | 0.22715 | 2.51097 | 3 | 0.082864 | 2.626049 | 1 | 1E+30 |
| NDP | 306 | 1.143774 | 2.484555 | 156 | 0.594988 | 2.997662 | 76 | 0.41891 | 3.160822 | 58 | 0.340484 |
| PJK | 306 | 0.844525 | 2.082415 | 45 | 0.332908 | 2.676329 | 8 | 0.187011 | 2.768185 | 5 | 0.108924 |
| QLB | 306 | 1.326661 | 2.424952 | 93 | 0.510324 | 2.835746 | 48 | 0.338822 | 2.997623 | 34 | 0.265136 |
| RJA | 306 | 0.842184 | 2.220567 | 51 | 0.377948 | 2.616423 | 21 | 0.186173 | 2.745588 | 12 | 0.133466 |
| SMJ | 306 | 1.097901 | 2.088282 | 31 | 0.33972 | 2.650454 | 7 | 0.129344 | 2.754731 | 4 | 0.046617 |
| SRB | 306 | 1.117644 | 2.181917 | 23 | 0.279114 | 2.469585 | 9 | 0.143303 | 2.715508 | 2 | 0.098238 |
| SWS | 306 | 0.822978 | 2.121365 | 15 | 0.471698 | 2.696374 | 5 | 0.339207 | 2.906246 | 3 | 0.285621 |
| VRC | 306 | 0.808814 | 2.299222 | 158 | 0.431643 | 2.700796 | 71 | 0.276701 | 2.888526 | 41 | 0.210714 |
| WCB | 306 | 0.715958 | 1.942814 | 7 | 0.270565 | 2.541731 | 1 | 1E+30 | | | |
| 0.05 | | | | 30 | | | 28 | | | 26 | |
| 0.025 | | | | 25 | | | 27 | | | 25 | |
| 0.01 | | | | 7 | | | 26 | | | 24 | |
| 0.005 | | | | 2 | | | 18 | | | 23 | |

| Subject | Cluster2 P0.001 Mean_T | Cluster2 P0.001 No. Voxels | Cluster2 P0.001 SD | Cluster2 P0.0005 Mean_T | Cluster2 P0.0005 No. Voxels | Cluster2 P0.0005 SD | Cluster2 P0.0001 Mean_T | Cluster2 P0.0001 No. Voxels | Cluster2 P0.0001 SD | Cluster2 P1 Mean_T | Cluster2 P1 No. Voxels |
|---|---|---|---|---|---|---|---|---|---|---|---|
| AKM | 3.608095 | 22 | 0.295767 | 3.699699 | 18 | 0.24601 | 3.938905 | 8 | 0.146644 | 1.79374 | 306 |
| ALS | 4.415851 | 14 | 0.345234 | 4.415851 | 14 | 0.345234 | 4.415851 | 14 | 0.345234 | 1.654652 | 306 |
| AMD | 4.968338 | 194 | 1.063419 | 5.052826 | 185 | 1.015786 | 5.23802 | 165 | 0.915265 | 3.771539 | 306 |
| ARG | | | | | | | | | | 1.033464 | 306 |
| ASF | 3.238879 | 8 | 0.077085 | 3.355881 | 2 | 0.017966 | | | | 1.477017 | 306 |
| BJM | 3.363983 | 9 | 0.156344 | 3.496061 | 5 | 0.05423 | | | | 0.473609 | 306 |
| BVM | | | | | | | | | | 0.779257 | 306 |
| CAP | | | | | | | | | | 0.233351 | 360 |

TABLE 9-continued

Voxel Subtraction Method Using Lie – True
Clusters 1, 2, 3, 4, 5, 6 and 7 as defined in Table 6

| Subject | | | | | | | | | | |
|---|---|---|---|---|---|---|---|---|---|---|
| CMB | 3.410126 | 15 | 0.219044 | 3.555864 | 9 | 0.155843 | 3.811553 | 1 | 1E+30 | 1.3009 | 306 |
| CRJ | 3.533499 | 61 | 0.320913 | 3.714888 | 39 | 0.260519 | 3.928637 | 21 | 0.133405 | 2.252034 | 306 |
| DCM | | | | | | | | | | 0.202914 | 306 |
| DLR | | | | | | | | | | 0.509161 | 306 |
| DMH | | | | | | | | | | 0.891299 | 306 |
| EBW | 3.695935 | 73 | 0.410263 | 3.758802 | 64 | 0.400453 | 4.138739 | 26 | 0.362526 | 2.215695 | 306 |
| ERB | 3.19661 | 2 | 0.08104 | | | | | | | 0.366049 | 306 |
| KTM | 3.168498 | 2 | 0.067902 | | | | | | | 0.508287 | 306 |
| KWW | 3.467873 | 9 | 0.221553 | 3.58804 | 6 | 0.171299 | 3.806805 | 2 | 0.026124 | 0.717543 | 306 |
| LPF | 3.336238 | 1 | 1E+30 | 3.336238 | 1 | 1E+30 | | | | 0.528765 | 306 |
| MKS | | | | | | | | | | 1.235026 | 306 |
| MLW | | | | | | | | | | 1.263474 | 306 |
| MSW | | | | | | | | | | 0.439591 | 306 |
| NDP | 3.40541 | 32 | 0.242429 | 3.646513 | 14 | 0.160779 | 3.884563 | 3 | 0.075832 | 1.558917 | 306 |
| PJK | | | | | | | | | | 0.782803 | 306 |
| QLB | 3.374912 | 9 | 0.110621 | 3.437442 | 6 | 0.079111 | | | | 0.831965 | 306 |
| RJA | | | | | | | | | | 0.847224 | 306 |
| SMJ | | | | | | | | | | 0.080486 | 306 |
| SRB | | | | | | | | | | −0.141422 | 306 |
| SWS | 3.309849 | 1 | 1E+30 | | | | | | | 0.151519 | 306 |
| VRC | 3.276453 | 5 | 0.090839 | 3.383429 | 2 | 0.027197 | | | | 1.646863 | 306 |
| WCB | | | | | | | | | | −0.150562 | 306 |
| 0.05 | 16 | | | 13 | | | 8 | | | 6 | |
| 0.025 | 15 | | | 12 | | | 7 | | | 3 | |
| 0.01 | 14 | | | 11 | | | 6 | | | 1 | |
| 0.005 | 13 | | | 10 | | | 5 | | | 0 | |

| Subject | Cluster2 P1 SD | Cluster3 P1 Mean_T | Cluster3 P1 No. Voxels | Cluster3 P0.05 SD | Cluster3 P0.05 Mean_T | Cluster3 P0.05 No. Voxels | Cluster3 P0.01 SD | Cluster3 P0.01 Mean_T | Cluster3 P0.01 No. Voxels | Cluster3 P0.005 SD | Cluster3 P0.005 Mean_T |
|---|---|---|---|---|---|---|---|---|---|---|---|
| AKM | 1.016918 | 1.765639 | 165 | 0.729689 | 2.27023 | 95 | 0.468567 | 2.83775 | 31 | 0.330074 | 2.997746 |
| ALS | 0.866856 | 1.429239 | 165 | 0.956106 | 2.249658 | 80 | 0.405895 | 2.682171 | 31 | 0.240691 | 2.867718 |
| AMD | 1.851706 | 4.049112 | 165 | 1.513243 | 4.212054 | 156 | 1.386996 | 4.482454 | 139 | 1.218778 | 4.622797 |
| ARG | 0.839704 | 0.41671 | 165 | 0.861466 | 1.677535 | 2 | 0.00254 | | | | |
| ASF | 0.915368 | 1.263218 | 165 | 0.956564 | 2.195584 | 65 | 0.368012 | 2.619205 | 23 | 0.206793 | 2.773443 |
| BJM | 1.230687 | 0.210831 | 165 | 0.809576 | 1.793477 | 2 | 0.001647 | | | | |
| BVM | 0.97285 | 0.009837 | 165 | 0.757885 | 1.685147 | 2 | 0.008021 | | | | |
| CAP | 0.973012 | 0.685236 | 165 | 0.546048 | 1.772936 | 3 | 0.099004 | | | | |
| CMB | 1.065339 | 1.588706 | 165 | 0.843647 | 2.317494 | 80 | 0.360921 | 2.524984 | 40 | 0.183369 | 2.766111 |
| CRJ | 0.919546 | 1.46158 | 165 | 0.723263 | 2.19412 | 68 | 0.314393 | 2.547299 | 23 | 0.190057 | 2.784618 |
| DCM | 0.77911 | 0.194517 | 165 | 0.701496 | 1.986521 | 4 | 0.142201 | | | | |
| DLR | 1.109772 | 0.189887 | 165 | 0.598179 | 1.5807 | 1 | 1E+30 | | | | |
| DMH | 1.034246 | 0.083345 | 165 | 0.728051 | 1.837315 | 1 | 1E+30 | | | | |
| EBW | 1.104784 | 1.955416 | 165 | 1.1174 | 2.674132 | 99 | 0.723045 | 3.131881 | 51 | 0.527974 | 3.281305 |
| ERB | 1.159728 | 1.237006 | 165 | 0.742588 | 2.038311 | 54 | 0.257062 | 2.498227 | 7 | 0.097868 | 2.624544 |
| KTM | 0.802732 | 0.758572 | 165 | 0.761742 | 1.866173 | 12 | 0.146164 | | | | |
| KWW | 1.417701 | 1.675854 | 165 | 0.900664 | 2.410337 | 83 | 0.5134 | 2.886856 | 38 | 0.357334 | 3.023799 |
| LPF | 0.955523 | 1.087109 | 165 | 0.752681 | 2.04939 | 37 | 0.251637 | 2.476879 | 5 | 0.110518 | 2.644939 |
| MKS | 0.712784 | 1.03607 | 165 | 0.75523 | 2.129592 | 37 | 0.252447 | 2.46789 | 10 | 0.085372 | 2.60479 |
| MLW | 0.67888 | 0.647561 | 165 | 0.860748 | 2.061496 | 26 | 0.319579 | 2.597503 | 5 | 0.194797 | 2.833665 |
| MSW | 0.963699 | 0.908486 | 165 | 0.47553 | 1.690835 | 1 | 1E+30 | | | | |
| NDP | 1.143774 | 1.821962 | 165 | 0.642529 | 2.230643 | 105 | 0.329332 | 2.570155 | 42 | 0.152309 | 2.698372 |
| PJK | 0.844525 | −0.048591 | 165 | 0.566018 | | | | | | | |
| QLB | 1.326661 | 3.013484 | 165 | 0.857544 | 3.099031 | 157 | 0.765634 | 3.370977 | 126 | 0.622566 | 3.46543 |
| RJA | 0.842184 | 1.873019 | 165 | 0.837887 | 2.324166 | 115 | 0.416601 | 2.705333 | 52 | 0.271162 | 2.873329 |
| SMJ | 1.097901 | −1.081475 | 165 | 0.6391 | | | | | | | |
| SRB | 1.117644 | −0.765649 | 165 | 0.53036 | | | | | | | |
| SWS | 0.822978 | 0.840823 | 165 | 1.187691 | 2.453945 | 39 | 0.616947 | 2.892776 | 22 | 0.452092 | 3.116082 |
| VRC | 0.808814 | 1.660862 | 165 | 0.691189 | 2.213615 | 84 | 0.438665 | 2.742776 | 28 | 0.289421 | 2.870692 |
| WCB | 0.715958 | 0.491254 | 165 | 0.615081 | 1.849735 | 5 | 0.137814 | | | | |
| 0.05 | | 8 | | | 27 | | | 17 | | | 17 |
| 0.025 | | 2 | | | 17 | | | 16 | | | 16 |
| 0.01 | | 2 | | | 5 | | | 15 | | | 15 |
| 0.005 | | 1 | | | 2 | | | 9 | | | 14 |

| Subject | Cluster3 P0.005 No. Voxels | Cluster3 P0.005 SD | Cluster3 P0.005 Mean_T | Cluster3 P0.001 No. Voxels | Cluster3 P0.001 SD | Cluster3 P0.001 Mean_T | Cluster3 P0.0005 No. Voxels | Cluster3 P0.0005 SD | Cluster3 P0.0005 Mean_T | Cluster3 P0.0001 No. Voxels | Cluster3 P0.0001 SD |
|---|---|---|---|---|---|---|---|---|---|---|---|
| AKM | 21 | 0.282864 | 3.342203 | 7 | 0.158512 | 3.46862 | 4 | 0.072232 | | | |
| ALS | 17 | 0.159873 | 3.192547 | 2 | 0.033038 | | | | | | |
| AMD | 130 | 1.132977 | 4.848977 | 115 | 1.002389 | 5.003704 | 105 | 0.908081 | 5.110759 | 98 | 0.842987 |
| ARG | | | | | | | | | | | |

TABLE 9-continued

Voxel Subtraction Method Using Lie – True
Clusters 1, 2, 3, 4, 5, 6 and 7 as defined in Table 6

| Subject | | | | | | | | | | |
|---|---|---|---|---|---|---|---|---|---|---|
| ASF | 13 | 0.127252 | | | | | | | | |
| BJM | | | | | | | | | | |
| BVM | | | | | | | | | | |
| CAP | | | | | | | | | | |
| CMB | 21 | 0.135708 | | | | | | | | |
| CRJ | 8 | 0.106019 | | | | | | | | |
| DCM | | | | | | | | | | |
| DLR | | | | | | | | | | |
| DMH | | | | | | | | | | |
| EBW | 50 | 0.463736 | 3.574313 | 29 | 0.383855 | 3.77437 | 19 | 0.327628 | 4.045345 | 10 | 0.195981 |
| ERB | 2 | 0.040684 | | | | | | | | |
| KTM | | | | | | | | | | |
| KWW | 29 | 0.294794 | 3.370851 | 10 | 0.182022 | 3.495646 | 6 | 0.123597 | | |
| LPF | 1 | 1E+30 | | | | | | | | |
| MKS | 2 | 0.002821 | | | | | | | | |
| MLW | 2 | 0.002395 | | | | | | | | |
| MSW | | | | | | | | | | |
| NDP | 20 | 0.104605 | | | | | | | | |
| PJK | | | | | | | | | | |
| QLB | 114 | 0.576067 | 3.695128 | 82 | 0.51728 | 3.847922 | 62 | 0.507091 | 4.284462 | 26 | 0.51748 |
| RJA | 31 | 0.222787 | 3.27697 | 5 | 0.084749 | 3.410056 | 1 | 1E+30 | | |
| SMJ | | | | | | | | | | |
| SRB | | | | | | | | | | |
| SWS | 15 | 0.375123 | 3.458799 | 7 | 0.220804 | 3.577761 | 5 | 0.136775 | | |
| VRC | 19 | 0.264341 | 3.487793 | 2 | 0.124965 | 3.487793 | 2 | 0.124965 | | |
| WCB | | | | | | | | | | |
| 0.05 | | | 9 | | | 8 | | | 3 | |
| 0.025 | | | 8 | | | 7 | | | 3 | |
| 0.01 | | | 7 | | | 7 | | | 3 | |
| 0.005 | | | 6 | | | 6 | | | 2 | |

| Subject | Cluster2 P1 Mean_T | Cluster2 P1 No. Voxels | Cluster2 P1 SD | Cluster3 P1 Mean_T | Cluster3 P1 No. Voxels | Cluster3 P1 SD | Cluster4 P1 Mean_T | Cluster4 P1 No. Voxels | Cluster4 P1 SD | Cluster4 P0.05 Mean_T | Cluster4 P0.05 No. Voxels |
|---|---|---|---|---|---|---|---|---|---|---|---|
| AKM | 1.79374 | 306 | 1.016918 | 1.765639 | 165 | 0.729689 | 1.37177 | 158 | 1.093485 | 2.407271 | 67 |
| ALS | 1.684652 | 306 | 0.666856 | 1.429230 | 165 | 0.966106 | 0.761558 | 158 | 1.012091 | 1.944645 | 43 |
| AMD | 3.771539 | 306 | 1.861706 | 4.049112 | 165 | 1.513243 | 1.939424 | 158 | 1.59559 | 3.127899 | 85 |
| ARG | 1.033464 | 306 | 0.839704 | 0.41671 | 165 | 0.861465 | 1.022532 | 158 | 0.757435 | 1.95675 | 36 |
| ASF | 1.477017 | 306 | 0.915368 | 1.263218 | 165 | 0.956564 | 0.09093 | 158 | 0.398421 | | |
| BJM | 0.473609 | 306 | 1.230687 | −0.210831 | 165 | 0.809576 | 1.424189 | 158 | 1.270919 | 2.652054 | 70 |
| BVM | 0.779257 | 306 | 0.97285 | 0.009837 | 165 | 0.757885 | 1.815143 | 158 | 1.122529 | 2.622656 | 88 |
| CAP | 0.233351 | 306 | 0.973012 | 0.685236 | 165 | 0.546048 | −0.228297 | 158 | 1.58805 | 2.190459 | 31 |
| CMB | 1.3009 | 306 | 1.065339 | 1.588706 | 165 | 0.843647 | −0.426451 | 158 | 1.399078 | 1.930017 | 11 |
| CRJ | 2.252034 | 306 | 0.919546 | 1.46158 | 165 | 0.723263 | 1.929597 | 158 | 0.87877 | 2.420785 | 109 |
| DCM | 0.203914 | 306 | 0.77911 | 0.194517 | 165 | 0.701496 | 0.088925 | 158 | 0.576433 | | |
| DLR | 0.509151 | 306 | 1.109772 | 0.189887 | 165 | 0.598179 | 0.504957 | 158 | 1.030048 | 2.215599 | 27 |
| DHH | 0.891299 | 306 | 1.034246 | −0.083346 | 165 | 0.728051 | 1.148741 | 158 | 0.869884 | 2.09531 | 51 |
| EBW | 2.215695 | 306 | 1.104784 | 1.955416 | 165 | 1.1174 | 2.23878 | 158 | 1.066955 | 2.823071 | 108 |
| ERD | 0.366049 | 306 | 1.159728 | 1.237006 | 165 | 0.742588 | 1.636281 | 158 | 0.909788 | 2.354403 | 83 |
| KTM | 0.508287 | 306 | 0.802733 | 0.758572 | 165 | 0.761742 | 0.59801 | 158 | 0.911007 | 2.007101 | 22 |
| KWW | 0.717543 | 306 | 1.417701 | 1.675854 | 165 | 0.900664 | 1.645961 | 158 | 0.80693 | 2.43997 | 65 |
| LPF | 0.528765 | 306 | 0.955523 | 1.087109 | 165 | 0.752681 | 1.922679 | 158 | 1.197257 | 2.829446 | 90 |
| MKS | 1.235026 | 306 | 0.712784 | 1.03607 | 165 | 0.75523 | 1.087207 | 158 | 0.604506 | 2.000576 | 27 |
| MLW | 1.263474 | 306 | 0.67888 | 0.647501 | 165 | 0.800748 | 0.72133 | 158 | 0.474896 | 1.824829 | 6 |
| MSW | 0.439591 | 306 | 0.963699 | 0.908486 | 165 | 0.47553 | 1.230864 | 158 | 0.966791 | 2.118703 | 62 |
| NDP | 1.558917 | 306 | 1.143774 | 1.821962 | 165 | 0.642529 | 2.035942 | 158 | 0.925129 | 2.515762 | 112 |
| PJK | 0.782803 | 306 | 0.844525 | −0.048591 | 165 | 0.566018 | 1.43729 | 158 | 1.029559 | 2.137926 | 93 |
| QLD | 0.831965 | 306 | 1.326661 | 3.013484 | 165 | 0.857243 | 1.410555 | 158 | 1.255847 | 2.713537 | 64 |
| RJA | 0.847224 | 306 | 0.842184 | 1.873019 | 165 | 0.837887 | 0.760722 | 158 | 0.795932 | 2.081353 | 21 |
| SMJ | 0.080488 | 306 | 1.097901 | −1.081475 | 165 | 0.6391 | −1.088376 | 158 | 0.948871 | | |
| SRG | −0.141422 | 306 | 1.117644 | −0.765649 | 165 | 0.53036 | 0.377064 | 158 | 0.748018 | 1.717632 | 4 |
| SWS | 0.151519 | 306 | 0.822978 | 0.840823 | 165 | 1.187691 | 1.07945 | 158 | 1.700526 | 2.573383 | 76 |
| VRC | 1.646863 | 306 | 0.808814 | 1.660862 | 165 | 0.691189 | 2.249441 | 158 | 0.930402 | 2.668740 | 115 |
| WCB | −0.150582 | 306 | 0.715958 | 0.491254 | 185 | 0.815081 | 0.283068 | 158 | 1.051304 | 2.368052 | 13 |
| 0.05 | 6 | | | 8 | | | 8 | | | 27 | |
| 0.025 | 3 | | | 2 | | | 3 | | | 21 | |
| 0.01 | 1 | | | 2 | | | 0 | | | 13 | |
| 0.005 | 0 | | | 1 | | | 0 | | | 6 | |

| Subject | Cluster4 P0.05 SD | Cluster4 P0.01 Mean_T | Cluster4 P0.01 No. Voxels | Cluster4 P0.01 SD | Cluster4 P0.005 Mean_T | Cluster4 P0.005 No. Voxels | Cluster4 P0.005 SD | Cluster4 P0.001 Mean_T | Cluster4 P0.001 No. Voxels | Cluster4 P0.001 SD | Cluster4 P0.0005 Mean_T |
|---|---|---|---|---|---|---|---|---|---|---|---|
| AKM | 0.565294 | 2.895946 | 31 | 0.447082 | 3.051888 | 23 | 0.415981 | 3.75362 | 5 | 0.30391 | 3.883952 |
| ALS | 0.169466 | 2.331649 | 1 | 1E+30 | | | | | | | |

TABLE 9-continued

Voxel Subtraction Method Using Lie − True
Clusters 1, 2, 3, 4, 5, 6 and 7 as defined in Table 6

| | | | | | | | | | | |
|---|---|---|---|---|---|---|---|---|---|---|
| AMD | 1.044526 | 3.542222 | 62 | 0.920311 | 3.729021 | 53 | 0.666662 | 4.15772 | 35 | 0.763407 | 4.323158 |
| ARG | 0.224693 | 2.39699 | 3 | 0.045772 | | | | | | | |
| ASF | | | | | | | | | | | |
| BJM | 0.487084 | 2.886786 | 52 | 0.298637 | 2.973562 | 43 | 0.252524 | 3.245548 | 17 | 0.087993 | 3.366053 |
| BVM | 0.716381 | 3.106754 | 50 | 0.576534 | 3.360757 | 36 | 0.47873 | 3.616092 | 24 | 0.376273 | 3.781335 |
| CAP | 0.299045 | 2.517251 | 11 | 0.113125 | 2.685124 | 3 | 0.045092 | | | | |
| CMB | 0.232591 | 2.479311 | 1 | 1E+30 | | | | | | | |
| CRJ | 0.427707 | 2.724927 | 62 | 0.277634 | 2.919545 | 36 | 0.199923 | 3.236061 | 8 | 0.073022 | 3.390729 |
| DCM | | | | | | | | | | | |
| DLR | 0.389189 | 2.620794 | 11 | 0.187716 | 2.738819 | 7 | 0.124939 | | | | |
| DHH | 0.299677 | 2.497195 | 13 | 0.128062 | 2.70509 | 3 | 0.085048 | | | | |
| EBW | 0.701785 | 3.128765 | 79 | 0.556771 | 3.288755 | 64 | 0.496517 | 3.672287 | 34 | 0.36206 | 3.806829 |
| ERD | 0.542147 | 2.887492 | 33 | 0.44701 | 3.104183 | 22 | 0.393578 | 3.498568 | 9 | 0.309306 | 3.610944 |
| KTM | 0.225274 | 2.352463 | 3 | 0.010027 | | | | | | | |
| KWW | 0.538762 | 2.879651 | 33 | 0.374848 | 3.029975 | 25 | 0.300262 | 3.37739 | 9 | 0.162948 | 3.488387 |
| LPF | 0.659744 | 3.184512 | 61 | 0.483841 | 3.315069 | 52 | 0.39799 | 3.583015 | 32 | 0.241819 | 3.638282 |
| MKS | 0.249004 | 2.428679 | 5 | 0.059943 | | | | | | | |
| MLW | 0.081330 | | | | | | | | | | |
| MSW | 0.399636 | 2.717915 | 14 | 0.331533 | 2.913053 | 9 | 0.253354 | 3.479848 | 1 | 1E+30 | 3.479848 |
| NDP | 0.471854 | 2.817087 | 68 | 0.33533 | 2.988163 | 46 | 0.271018 | 3.320647 | 15 | 0.137727 | 3.496888 |
| PJK | 0.371965 | 2.676257 | 24 | 0.251457 | 2.6477 | 13 | 0.223049 | 3.214937 | 2 | 0.10987 | |
| QLD | 0.636281 | 3.040412 | 43 | 0.503917 | 3.216718 | 33 | 0.442042 | 3.581291 | 17 | 0.304046 | 3.73889 |
| RJA | 0.39173 | 2.894968 | 3 | 0.181497 | 2.894968 | 3 | 0.181497 | 3.122796 | 1 | 1E+30 | |
| SMJ | | | | | | | | | | | |
| SRG | 0.090755 | | | | | | | | | | |
| SWS | 0.627097 | 3.043407 | 42 | 0.433575 | 3.088837 | 39 | 0.410434 | 3.613422 | 13 | 0.254055 | 3.682085 |
| VRC | 0.699412 | 3.055898 | 73 | 0.580592 | 3.199063 | 59 | 0.556646 | 3.705324 | 26 | 0.455506 | 3.921858 |
| WCB | 0.27715 | 2.566487 | 8 | 0.126069 | 2.758384 | 2 | 0.134837 | | | | |
| 0.05 | | 25 | | | 20 | | | 16 | | | 14 |
| 0.025 | | 24 | | | 19 | | | 15 | | | 13 |
| 0.01 | | 23 | | | 19 | | | 15 | | | 13 |
| 0.005 | | 15 | | | 18 | | | 14 | | | 12 |

| Subject | Cluster4 P0.0005 No. Voxels | Cluster4 P0.0005 SD | Cluster4 P0.0001 Mean_T | Cluster4 P0.0001 No. Voxels | Cluster4 P0.0001 SD | Cluster2 P2 Mean_T | Cluster2 P1 No. Voxels | Cluster2 P1 SD | Cluster3 P1 Mean_T | Cluster3 P1 No. Voxels | Cluster3 P1 SD |
|---|---|---|---|---|---|---|---|---|---|---|---|
| AKM | 4 | 0.174698 | 4.057486 | 2 | 0.026236 | 1.78374 | 306 | 1.016918 | 1.765638 | 165 | 0.729689 |
| ALS | | | | | | 1.884652 | 306 | 0.866856 | 1.4289238 | 165 | 0.966106 |
| AMD | 30 | 0.69865 | 4.695099 | 20 | 0.556651 | 3.771539 | 306 | 1.861706 | 4.049112 | 165 | 1.533243 |
| ARG | | | | | | 1.033464 | 306 | 0.839704 | 0.41671 | 165 | 0.561466 |
| ASF | | | | | | 1.477017 | 306 | 0.915368 | 1.263218 | 165 | 0.956564 |
| BJM | 4 | 0.024746 | | | | 0.473609 | 306 | 1.230687 | 0.210831 | 165 | 0.809576 |
| BVM | 17 | 0.324364 | 4.03688 | 9 | 0.227212 | 0.779217 | 306 | 0.97281 | 0.009837 | 165 | 0.757895 |
| CAP | | | | | | 0.233351 | 306 | 0.973012 | 0.685236 | 165 | 0.546048 |
| CMB | | | | | | 1.3009 | 306 | 1.065339 | 1.588706 | 165 | 0.843647 |
| CRJ | 1 | 1E+30 | | | | 2.257034 | 306 | 0.919546 | 1.46158 | 165 | 0.723263 |
| DCM | | | | | | 0.202914 | 306 | 0.77911 | 0.294517 | 165 | 0.701496 |
| DLR | | | | | | 0.509161 | 306 | 1.109772 | 0.189887 | 165 | 0.390179 |
| DHH | | | | | | 0.0891299 | 304 | 1.034246 | −0.083346 | 165 | 0.728051 |
| EBW | 26 | 0.305425 | 4.020802 | 16 | 0.173677 | 2.215605 | 304 | 1.104784 | 1.955416 | 165 | 1.1174 |
| ERD | 6 | 0.32357 | 4.02293 | 2 | 0.299716 | 0.366049 | 306 | 1.159728 | 1.237006 | 165 | 0.742588 |
| KTM | | | | | | 0.508287 | 306 | 0.802732 | 0.758572 | 165 | 0.781742 |
| KWW | 5 | 0.136422 | | | | 0.717843 | 306 | 1.417701 | 1.675854 | 165 | 0.000664 |
| LPF | 28 | 0.205008 | 3.845443 | 10 | 0.135362 | 0.528765 | 306 | 0.955523 | 1.087109 | 185 | 0.752601 |
| MKS | | | | | | 1.236024 | 306 | 0.712734 | 1.03607 | 165 | 0.75523 |
| MLW | | | | | | 1.263474 | 306 | 0.67888 | 0.647561 | 165 | 0.860748 |
| MSW | 1 | 1E+30 | | | | 0.439501 | 306 | 0.963899 | 0.908486 | 165 | 0.47553 |
| NDP | 5 | 0.031243 | | | | 1.538917 | 306 | 1.143774 | 1.821962 | 165 | 0.842529 |
| PJK | | | | | | 0.782807 | 306 | 0.844525 | −0.048591 | 165 | 0.566018 |
| QLD | 12 | 0.213880 | 3.900091 | 7 | 0.086679 | 0.031945 | 306 | 1.326661 | 1.013484 | 165 | 0.057544 |
| RJA | | | | | | 0.847224 | 306 | 0.842184 | 1.873019 | 165 | 0.837887 |
| SMJ | | | | | | 0.080486 | 306 | 1.097901 | −1.081475 | 165 | 0.6391 |
| SRG | | | | | | −0.141422 | 306 | 1.117644 | −0.765649 | 165 | 0.53036 |
| SWS | 11 | 0.213562 | 3.925802 | 4 | 0.079467 | 0.151519 | 306 | 0.822978 | 0.940823 | 165 | 1.187691 |
| VRC | 18 | 0.398185 | 4.163994 | 11 | 0.309849 | 1.640003 | 306 | 0.808814 | 1.660862 | 165 | 0.691189 |
| WCB | | | | | | −0.150562 | 306 | 0.715958 | 0.491254 | 165 | 0.015081 |
| 0.05 | | | 9 | | | 6 | | | 8 | | |
| 0.025 | | | 8 | | | 3 | | | 2 | | |
| 0.01 | | | 8 | | | 1 | | | 2 | | |
| 0.005 | | | 7 | | | 0 | | | 1 | | |

| Subject | Cluster4 P1 Mean_T | Cluster4 P1 No. Voxels | Cluster4 P1 SD | Cluster5 P1 Mean_T | Cluster5 P1 No. Voxels | Cluster5 P1 SD | Cluster5 P0.05 Mean_T | Cluster5 P0.05 No. Voxels | Cluster5 P0.05 SD | Cluster5 P0.01 Mean_T | Cluster5 P0.01 No. Voxels |
|---|---|---|---|---|---|---|---|---|---|---|---|

TABLE 9-continued

Voxel Subtraction Method Using Lie – True
Clusters 1, 2, 3, 4, 5, 6 and 7 as defined in Table 6

| | | | | | | | | | | | |
|---|---|---|---|---|---|---|---|---|---|---|---|
| AKM | 1.37177 | 158 | 1.093485 | 1.367555 | 154 | 1.385887 | 2.589485 | 69 | 0.579251 | 2.94275 | 44 |
| ALS | 0.761558 | 158 | 1.012091 | 1.226481 | 154 | 0.872727 | 2.247111 | 49 | 0.233531 | 2.574531 | 21 |
| AMD | 1.939424 | 158 | 1.59559 | 3.21852 | 154 | 1.858574 | 4.118391 | 118 | 0.898451 | 4.208255 | 113 |
| ARG | 1.022532 | 158 | 0.757435 | 0.506907 | 154 | 1.037654 | 1.879502 | 22 | 0.135088 | | |
| ASF | 0.09083 | 158 | 0.398421 | 0.351706 | 154 | 0.734238 | 1.877779 | 7 | 0.140954 | | |
| BJM | 1.424189 | 158 | 1.270919 | 0.042536 | 154 | 0.880487 | 1.718099 | 2 | 0.024138 | | |
| BVM | 1.815143 | 158 | 1.122529 | 0.705889 | 154 | 1.127871 | 2.441286 | 21 | 0.815354 | 2.821483 | 17 |
| CAP | −0.228297 | 158 | 1.58805 | 0.35547 | 154 | 0.435392 | 1.702389 | 2 | 0.072736 | | |
| CMB | −0.426451 | 158 | 1.399078 | 1.156738 | 154 | 0.875909 | 2.185638 | 42 | 0.362513 | 2.637659 | 12 |
| CRJ | 1.929597 | 158 | 0.87877 | 1.568332 | 154 | 0.860764 | 2.359896 | 66 | 0.612821 | 2.927619 | 30 |
| DCM | 0.88925 | 158 | 0.576433 | 0.390404 | 154 | 0.889592 | 1.699013 | 1 | 1E+30 | | |
| DLR | 0.504957 | 158 | 1.030048 | −0.104774 | 154 | 0.681409 | | | | | |
| DMH | 1.140741 | 158 | 0.869884 | 0.89661 | 154 | 0.977256 | 1.906861 | 41 | 0.150283 | | |
| EBW | 2.23878 | 158 | 1.666255 | 1.821391 | 154 | 0.968669 | 2.550438 | 83 | 0.642424 | 2.936117 | 47 |
| ERB | 1.436281 | 158 | 0.909788 | 0.496381 | 154 | 0.804574 | 1.871824 | 10 | 0.185768 | | |
| KTM | 0.59801 | 158 | 0.911007 | 0.419265 | 154 | 0.467746 | | | | | |
| KWW | 1.645961 | 158 | 0.80693 | 2.410879 | 154 | 1.007714 | 2.857384 | 122 | 0.646193 | 3.095115 | 95 |
| LPF | 1.922679 | 158 | 1.197257 | 0.843606 | 154 | 0.773455 | 1.810058 | 19 | 0.13336 | | |
| MKS | 1.087207 | 158 | 0.604506 | 1.498341 | 154 | 1.078717 | 2.447842 | 84 | 0.535901 | 2.882189 | 33 |
| MLW | 0.72133 | 158 | 0.474896 | 1.490451 | 154 | 0.026221 | 2.168906 | 76 | 0.398751 | 2.621215 | 26 |
| MSW | 1.230864 | 158 | 0.966791 | 0.984993 | 154 | 0.756121 | 2.157635 | 31 | 0.313909 | 2.559431 | 9 |
| NDP | 2.035942 | 158 | 0.925129 | 1.492635 | 154 | 0.725081 | 2.152998 | 68 | 0.271585 | 2.504 | 17 |
| PJK | 1.43729 | 158 | 1.029559 | 0.282194 | 154 | 0.464762 | | | | | |
| QLB | 1.410555 | 158 | 1.255847 | 2.666572 | 154 | 0.796603 | 2.833214 | 138 | 0.658387 | 3.100234 | 103 |
| RJA | 0.760722 | 158 | 0.795932 | 1.681168 | 154 | 0.752114 | 2.282897 | 83 | 0.320308 | 2.573367 | 35 |
| SMJ | −1.088376 | 158 | 0.948871 | −1.02056 | 154 | 0.909038 | | | | | |
| SRB | 0.377064 | 158 | 0.748018 | −0.62872 | 154 | 0.870334 | | | | | |
| SWS | 1.07945 | 158 | 1.700526 | 0.832715 | 154 | 1.186397 | 2.45264 | 37 | 0.54933 | 2.934174 | 18 |
| VRC | 2.249441 | 158 | 0.930402 | 1.245825 | 154 | 0.881094 | 2.21716 | 52 | 0.344227 | 2.583901 | 19 |
| WCB | 0.283068 | 158 | 1.051304 | 0.531863 | 154 | 0.528882 | 1.952659 | 5 | 0.201142 | | |
| 0.05 | 8 | | | 5 | | | 25 | | | 10 | |
| 0.025 | 3 | | | 3 | | | 15 | | | 15 | |
| 0.01 | 0 | | | 3 | | | 8 | | | 14 | |
| 0.005 | 0 | | | 1 | | | 2 | | | 10 | |

| Subject | Cluster5 P0.01 SD | Cluster5 P0.005 Mean_T | Cluster5 P0.005 No. Voxels | Cluster5 P0.005 SD | Cluster5 P0.001 Mean_T | Cluster5 P0.001 No. Voxels | Cluster5 P0.001 SD | Cluster5 P0.0005 Mean_T | Cluster5 P0.0005 No. Voxels | Cluster5 P0.0005 SD | Cluster5 P0.0001 Mean_T |
|---|---|---|---|---|---|---|---|---|---|---|---|
| AKM | 0.405298 | 3.10474 | 32 | 0.357813 | 3.496933 | 13 | 0.176779 | 3.542328 | 11 | 0.151316 | 3.794297 |
| ALS | 0.106513 | 2.667504 | 10 | 0.045753 | | | | | | | |
| AMD | 0.806388 | 4.272144 | 109 | 0.747424 | 4.368507 | 102 | 0.671416 | 4.401711 | 99 | 0.053403 | 4.591391 |
| ARG | | | | | | | | | | | |
| ASF | | | | | | | | | | | |
| BJM | | | | | | | | | | | |
| BVM | 0.36498 | 3.084934 | 10 | 0.237547 | 3.304248 | 6 | 0.052842 | 3.354865 | 2 | 0.025402 | |
| CAP | | | | | | | | | | | |
| CMB | 0.263128 | 2.900319 | 5 | 0.188279 | 3.119309 | 1 | 1E+30 | | | | |
| CRJ | 0.437337 | 3.118237 | 21 | 0.385898 | 3.506461 | 9 | 0.259074 | 3.717974 | 5 | 0.12E+13 | 3.860988 |
| DCM | | | | | | | | | | | |
| DLR | | | | | | | | | | | |
| DMH | | | | | | | | | | | |
| EBW | 0.517218 | 3.156559 | 36 | 0.473149 | 3.55981 | 18 | 0.328013 | 3.747752 | 12 | 0.233682 | 3.96241 |
| ERB | | | | | | | | | | | |
| KTM | | | | | | | | | | | |
| KWW | 0.521703 | 3.247417 | 78 | 0.472499 | 3.813114 | 40 | 0.380342 | 3.786404 | 27 | 0.307268 | 4.037863 |
| LPF | | | | | | | | | | | |
| MKS | 0.3952 | 3.049538 | 22 | 0.359726 | 2.429968 | 10 | 0.157338 | 3.517672 | 7 | 0.09201 | |
| MLW | 0.286209 | 2.958363 | 10 | 0.137404 | 3.230629 | 1 | 1E+30 | | | | |
| MSW | 0.14396 | 2.721909 | 3 | 0.113609 | | | | | | | |
| NDP | 0.11977 | 2.687174 | 4 | 0.048443 | | | | | | | |
| PJK | | | | | | | | | | | |
| QLB | 0.538124 | 2.295968 | 79 | 0.456279 | 3.581225 | 49 | 0.32908 | 3.751208 | 34 | 0.246874 | 4.021046 |
| RJA | 0.176275 | 2.766358 | 14 | 0.105515 | | | | | | | |
| SMJ | | | | | | | | | | | |
| SRB | | | | | | | | | | | |
| SWS | 0.347755 | 3.059849 | 11 | 0.287771 | 3.325501 | 6 | 0.182816 | 3.54997 | 2 | 0.191762 | |
| VRC | 0.215098 | 2.808487 | 4 | 0.122453 | | | | | | | |
| WCB | | | | | | | | | | | |

TABLE 9-continued

Voxel Subtraction Method Using Lie − True
Clusters 1, 2, 3, 4, 5, 6 and 7 as defined in Table 6

| | | | | | | | | | |
|---|---|---|---|---|---|---|---|---|---|
| 0.05 | | 16 | | 11 | | 9 | | 4 | |
| 0.025 | | 15 | | 10 | | 8 | | 5 | |
| 0.01 | | 14 | | 10 | | 8 | | 5 | |
| 0.005 | | 13 | | 9 | | 7 | | 4 | |

| Subject | Cluster5 P0.0001 No. Voxels | Cluster5 P0.0001 SD | Cluster2 P1 Mean_T | Cluster2 P1 No. Voxels | Cluster2 P1 SD | Cluster3 P1 Mean_T | Cluster3 P1 No. Voxels | Cluster3 P1 SD | Cluster4 P1 Mean_T | Cluster4 P1 No. Voxels | Cluster4 P1 SD |
|---|---|---|---|---|---|---|---|---|---|---|---|
| AKM | 2 | 0.021338 | 1.79374 | 306 | 1.016910 | 1.765639 | 165 | 0.729639 | 1.37177 | 158 | 1.093485 |
| ALS | | | 1.884653 | 306 | 0.064856 | 1.429239 | 165 | 0.964105 | 0.761330 | 158 | 1.012091 |
| AMD | 81 | 0.565636 | 3.771539 | 306 | 1.861704 | 4.049117 | 165 | 1.613347 | 1.939474 | 158 | 1.60669 |
| ARG | | | 1.033464 | 306 | 0.039704 | 0.41671 | 165 | 0.861466 | 1.022332 | 158 | 0.0757425 |
| ASF | | | 1.477017 | 306 | 0.915366 | 1.263216 | 165 | 0.956564 | 0.08093 | 158 | 0.398421 |
| BJM | | | 0.471609 | 306 | 1.730587 | −0.210831 | 165 | 0.8095776 | 1.424189 | 158 | 1.270919 |
| BVM | | | 0.774257 | 306 | 0.97295 | 0.009837 | 165 | 0.757865 | 1.015143 | 158 | 1.122579 |
| CAP | | | 0.212251 | 306 | 0.973012 | 0.605236 | 165 | 0.546048 | −0.228297 | 158 | 1.58005 |
| CMB | | | 1.3009 | 306 | 1.965339 | 1.568706 | 165 | 0.443647 | −0.420451 | 158 | 1.395078 |
| CRJ | 2 | 0.091402 | 2.232034 | 306 | 0.919544 | 1.46158 | 165 | 0.723263 | 1.929587 | 158 | 0.67877 |
| DCM | | | 0.202914 | 306 | 0.77911 | 0.194517 | 165 | 0.701496 | 0.088925 | 158 | 0.576433 |
| DLR | | | 0.504141 | 306 | 1.109772 | 0.189637 | 165 | 0.398179 | 0.504937 | 158 | 1.030048 |
| DMH | | | 0.831299 | 306 | 1.034246 | −0.083346 | 165 | 0.728051 | 1.148741 | 158 | 0.889884 |
| EBW | 5 | 0.173241 | 2.215895 | 306 | 2.104784 | 1.955416 | 165 | 1.1174 | 2.23878 | 158 | 1.066955 |
| ERB | | | 0.366049 | 306 | 1.115723 | 1.237006 | 165 | 0.742588 | 1.626281 | 158 | 0.909788 |
| KTM | | | 0.508287 | 306 | 0.802732 | 0.758572 | 165 | 0.761742 | 0.59801 | 158 | 0.911007 |
| KWW | 14 | 0.180985 | 0.717843 | 306 | 1.417701 | 1.675854 | 165 | 0.900664 | 1.645961 | 158 | 0.89693 |
| LPF | | | 0.628765 | 306 | 0.065523 | 1.087109 | 165 | 0.753681 | 1.922679 | 158 | 1.197257 |
| MKS | | | 1.235026 | 306 | 0.712784 | 1.03807 | 165 | 0.75523 | 1.087207 | 158 | 0.604506 |
| MLW | | | 1.263474 | 306 | 0.67889 | 0.647561 | 165 | 0.880748 | 0.72133 | 158 | 0.474896 |
| MSW | | | 0.439591 | 306 | 0.963699 | 0.908488 | 165 | 0.47553 | 1.230864 | 158 | 0.968791 |
| NDP | | | 1.556917 | 306 | 1.143774 | 1.821961 | 165 | 0.442519 | 2.035942 | 158 | 0.925129 |
| PJK | | | 0.767803 | 306 | 0.644525 | −0.048591 | 165 | 0.566018 | 1.43739 | 158 | 1.079539 |
| QLB | 14 | 0.099023 | 0.831965 | 306 | 1.326061 | 3.013484 | 165 | 0.857544 | 1.410553 | 158 | 1.253847 |
| RJA | | | 0.847224 | 306 | 0.842164 | 1.473019 | 165 | 0.837687 | 0.760722 | 158 | 0.795922 |
| SMJ | | | 0.080465 | 306 | 1.097901 | −1.081475 | 165 | 0.6391 | −1.086376 | 158 | 0.946973 |
| SRB | | | −0.141422 | 306 | 1.117644 | −0.765849 | 165 | 0.53038 | 0.377084 | 158 | 0.748018 |
| SWS | | | 0.151519 | 306 | 0.022978 | 0.840823 | 165 | 1.187681 | 1.07945 | 158 | 1.700526 |
| VRC | | | 1.646463 | 306 | 0.806814 | 1.640862 | 165 | 0.691189 | 2.244941 | 158 | 0.930402 |
| WCB | | | −0.150583 | 306 | 0.715053 | 0.491254 | 165 | 0.615081 | 0.203068 | 158 | 1.051304 |
| 0.05 | | | | | 0 | | 8 | | | 8 | |
| 0.025 | | | | | 3 | | 2 | | | 3 | |
| 0.01 | | | | | 1 | | 1 | | | 0 | |
| 0.005 | | | | | 0 | | 1 | | | 0 | |

| Subject | Cluster5 P1 Mean_T | Cluster6 P1 Mean_T | Cluster6 P1 No. Voxels | Cluster6 P1 SD | Cluster6 P0.05 Mean_T | Cluster6 P0.05 No. Voxels | Cluster6 P0.05 SD | Cluster6 P0.01 Mean_T | Cluster6 P0.01 No. Voxels | Cluster6 P0.01 SD | Cluster6 P0.005 Mean_T |
|---|---|---|---|---|---|---|---|---|---|---|---|
| AKM | 1.367355 | −0.040366 | 51 | 0.61776 | 1.805644 | 1 | 1E+30 | | | | |
| ALS | 1.226481 | 0.783479 | 51 | 0.408329 | | | | | | | |
| AMD | 3.21812 | 1.460618 | 51 | 1.434372 | 2.691447 | 29 | 0.666964 | 3.21417 | 18 | 0.463041 | 3.189383 |
| ARG | 0.506907 | 0.28495 | 51 | 0.476978 | | | | | | | |
| ASF | 0.351706 | 0.320366 | 51 | 0.494720 | | | | | | | |
| BJM | 0.042536 | 0.820893 | 51 | 1.082247 | 2.356422 | 11 | 0.35465 | 2.680556 | 5 | 0.206517 | 2.767983 |
| BVM | 0.705869 | 0.097547 | 51 | 1.276692 | 2.232257 | 18 | 0.445766 | 2.735597 | 6 | 0.235496 | 2.876452 |
| CAP | 0.35547 | 0.308032 | 51 | 0.737972 | | | | | | | |
| CMB | 1.156738 | 1.23011 | 51 | 0.583054 | 2.114019 | 11 | 0.340731 | 2.632058 | 3 | 0.195799 | 2.807397 |
| CRJ | 1.508322 | 0.04733 | 51 | 0.475899 | 1.788981 | 1 | 1E+70 | | | | |
| DCM | 0.390464 | 1.183025 | 51 | 0.84958 | 2.091553 | 17 | 0.231246 | 2.480145 | 3 | 0.087975 | 2.591049 |
| DLR | −0.164774 | 0.285329 | 51 | 0.530754 | | | | | | | |
| DMH | 0.89641 | 1.437905 | 51 | 1.045685 | 2.47805 | 21 | 0.482647 | 2.748409 | 14 | 0.326509 | 2.878592 |
| EBW | 1.821391 | 1.465005 | 51 | 0.039869 | 2.270051 | 23 | 0.448717 | 2.234936 | 9 | 0.288435 | 2.957633 |
| ERB | 0.496383 | 0.321999 | 51 | 1.207364 | 2.048979 | 7 | 0.199255 | | | | |
| KTM | 0.419245 | 0.335383 | 51 | 0.485358 | | | | | | | |
| KWW | 2.419879 | 1.201106 | 51 | 0.745965 | 2.095933 | 13 | 0.231662 | 2.414048 | 2 | 0.055782 | |
| LPF | 0.843606 | 0.406506 | 51 | 0.551366 | | | | | | | |
| MKS | 1.498341 | 0.397492 | 51 | 0.776964 | 1.915975 | 4 | 0.237113 | | | | |
| MLW | 1.490431 | 0.372394 | 51 | 0.38838 | | | | | | | |
| MSW | 0.984993 | 0.535276 | 51 | 0.720971 | 2.040975 | 3 | 0.04554 | | | | |
| NDP | 1.492635 | 0.590285 | 51 | 0.0842317 | 1.830676 | 6 | 0.147407 | | | | |
| PJK | 0.282104 | −0.196814 | 51 | 3.2203 | 1.965102 | 7 | 0.192896 | | | | |
| QLB | 2.666572 | 1.152001 | 51 | 1.006905 | 1.40476 | 15 | 0.506169 | 2.776752 | 9 | 0.250706 | 2.02386 |
| RJA | 1.601168 | 0.092111 | 51 | 0.466725 | 1.79109 | 2 | 0.00665 | | | | |
| SMJ | −1.2058 | −0.299881 | 51 | 0.346451 | | | | | | | |
| SRB | −0.62872 | 0.448093 | 51 | 0.885647 | 2.13712 | 5 | 0.269722 | 2.62281 | 1 | 1E+30 | 2.62281 |
| SWS | 0.632715 | 2.170396 | 51 | 0.060376 | 2.231623 | 44 | 0.459476 | 2.70994 | 23 | 0.27499 | 2.894034 |

TABLE 9-continued

Voxel Subtraction Method Using Lie – True
Clusters 1, 2, 3, 4, 5, 6 and 7 as defined in Table 6

| | | | | | | | | | | |
|---|---|---|---|---|---|---|---|---|---|---|
| VRC | 1.245825 | 0.50352 | 51 | 0.043321 | 1.802654 | 3 | 0.040374 | | | |
| WCB | 0.531863 | 0.377851 | 51 | 1.40261 | 2.101764 | 14 | 0.361432 | 2.701522 | 4 | 0.218543 | 2.805336 |
| 0.03 | 3 | 2 | | 21 | | 12 | | 11 | | |
| 0.025 | 3 | 1 | | 25 | | 12 | | 11 | | |
| 0.01 | 3 | 0 | | 5 | | 12 | | 11 | | |
| 0.005 | 1 | 0 | | 0 | | 0 | | 10 | | |

| Subject | Cluster6 P0.005 No. Voxels | Cluster6 P0.005 SD | Cluster6 P0.001 Mean_T | Cluster6 P0.001 No. Voxels | Cluster6 P0.001 SD | Cluster6 P0.0005 Mean_T | Cluster6 P0.0005 No. Voxels | Cluster6 P0.0005 SD | Cluster6 P0.0001 Mean_T | Cluster6 P0.0001 No. Voxels | Cluster6 P0.0001 SD |
|---|---|---|---|---|---|---|---|---|---|---|---|
| AKM | | | | | | | | | | | |
| ALS | | | | | | | | | | | |
| AMD | 14 | 0.4354 | 3.585265 | 1 | 0.264651 | 3.670944 | 6 | 0.249719 | 3.904633 | 2 | 0.057206 |
| ARG | | | | | | | | | | | |
| ASF | | | | | | | | | | | |
| BJM | 4 | 0.122847 | | | | | | | | | |
| BVM | 4 | 0.153735 | | | | | | | | | |
| CAP | | | | | | | | | | | |
| CMB | 1 | 2E+30 | | | | | | | | | |
| CRJ | | | | | | | | | | | |
| DCM | 1 | 1E+30 | | | | | | | | | |
| DLR | | | | | | | | | | | |
| DMH | 6 | 0.341096 | 3.329729 | 2 | 0.243749 | 3.501378 | 1 | 1E+30 | | | |
| EBW | 5 | 0.185146 | 3.147013 | 2 | 0.052193 | | | | | | |
| ERB | | | | | | | | | | | |
| KTM | | | | | | | | | | | |
| KWW | | | | | | | | | | | |
| LPF | | | | | | | | | | | |
| MKS | | | | | | | | | | | |
| MLW | | | | | | | | | | | |
| MSW | | | | | | | | | | | |
| NDP | | | | | | | | | | | |
| PJK | | | | | | | | | | | |
| QLB | 6 | 0.14793 | 3.113833 | 1 | 1E+30 | | | | | | |
| RJA | | | | | | | | | | | |
| SMJ | | | | | | | | | | | |
| SRB | 1 | 1E+30 | | | | | | | | | |
| SWS | 13 | 0.226726 | 3.229988 | 2 | 0.014042 | | | | | | |
| VRC | | | | | | | | | | | |
| WCB | 3 | 0.1473034 | | | | | | | | | |
| 0.03 | | | | 6 | | 2 | | 1 | | | |
| 0.025 | | | | 5 | | 2 | | 1 | | | |
| 0.01 | | | | 5 | | 2 | | 1 | | | |
| 0.005 | | | | 4 | | 1 | | 0 | | | |

| Subject | Cluster 7 P1 Mean_T | Cluster 7 P1 No. Voxels | Cluster 7 P1 SD | Cluster 7 P0.05 Mean_T | Cluster 7 P0.05 No. Voxels | Cluster 7 P0.05 SD | Cluster 7 P0.01 Mean_T | Cluster 7 P0.01 No. Voxels | Cluster 7 P0.01 SD | Cluster 7 P0.005 Mean_T | Cluster 7 P0.005 No. Voxels |
|---|---|---|---|---|---|---|---|---|---|---|---|
| AKM | 0.960228 | 49 | 1.071553 | 2.286646 | 15 | 0.374888 | 2.608006 | 8 | 0.134893 | 2.700928 | 5 |
| ALS | 1.518208 | 49 | 0.768821 | 2.177229 | 23 | 0.373594 | 2.657177 | 7 | 0.184828 | 2.761661 | 5 |
| AMD | −0.325383 | 49 | 1.672348 | 3.415551 | 6 | 1.453276 | 3.72861 | 5 | 1.395126 | 4.030663 | 4 |
| ARG | −1.039943 | 49 | 0.690786 | | | | | | | | |
| ASF | −0.565709 | 49 | 0.974819 | | | | | | | | |
| BJM | 2.160736 | 49 | 1.096434 | 2.677502 | 37 | 0.616813 | 3.112999 | 22 | 0.376898 | 3.18027 | 20 |
| BVM | 2.16668 | 49 | 1.051656 | 2.638351 | 38 | 0.552359 | 2.878547 | 28 | 0.430921 | 3.073606 | 19 |
| CAP | −0.298142 | 49 | 0.856875 | | | | | | | | |
| CMB | 2.281975 | 49 | 0.870379 | 2.676806 | 36 | 0.644444 | 2.975835 | 25 | 0.54022 | 3.33196 | 15 |
| CRJ | 2.628065 | 49 | 0.493235 | 2.674287 | 47 | 0.448464 | 2.847962 | 37 | 0.323852 | 3.000126 | 26 |
| DCM | 0.207399 | 49 | 0.354782 | | | | | | | | |
| DLR | −0.140928 | 49 | 0.493472 | | | | | | | | |
| DMH | 1.578253 | 49 | 0.595733 | 2.082045 | 23 | 0.218708 | 2.469403 | 3 | 0.037533 | | |
| EBW | 1.647454 | 49 | 0.793113 | 2.30635 | 25 | 0.435947 | 2.782977 | 9 | 0.306107 | 2.890241 | 7 |
| ERB | 0.994901 | 49 | 0.718918 | 1.841066 | 10 | 0.097858 | | | | | |
| KTM | 0.834359 | 49 | 0.37586 | | | | | | | | |
| KWW | 2.952558 | 49 | 0.749914 | 3.017394 | 47 | 0.694863 | 3.27403 | 38 | 0.494198 | 3.337468 | 35 |
| LPF | 1.414729 | 49 | 0.827711 | 2.397418 | 15 | 0.593616 | 2.926703 | 7 | 0.449033 | 3.285369 | 4 |
| MKS | 0.901171 | 49 | 0.631467 | 1.832231 | 7 | 0.225947 | 2.359045 | 1 | 1E+30 | | |
| MLW | 1.683557 | 49 | 0.802143 | 2.430297 | 23 | 0.256034 | 2.600821 | 14 | 0.143535 | 2.742696 | 6 |
| MSW | 2.666703 | 49 | 1.179356 | 3.340059 | 34 | 0.666687 | 3.502323 | 30 | 0.526544 | 3.580252 | 28 |
| NDP | 2.071153 | 49 | 0.572098 | 2.330067 | 38 | 0.326603 | 2.578824 | 19 | 0.186305 | 2.760288 | 8 |
| PJK | 1.932882 | 49 | 0.834674 | 2.439895 | 32 | 0.427889 | 2.744511 | 19 | 0.235373 | 2.830379 | 15 |
| QLB | −0.272034 | 49 | 0.602952 | | | | | | | | |

TABLE 9-continued

Voxel Subtraction Method Using Lie – True

Clusters 1, 2, 3, 4, 5, 6 and 7 as defined in Table 6

| | | | | | | | | | | |
|---|---|---|---|---|---|---|---|---|---|---|
| RJA | 1.496289 | 49 | 0.577963 | 1.996845 | 22 | 0.197061 | 2.365148 | 2 | 0.023223 | |
| SMJ | 0.13501 | 49 | 0.689024 | | | | | | | |
| SRB | 0.323523 | 49 | 0.39935 | | | | | | | |
| SWS | 1.66915 | 49 | 0.93709 | 2.49294 | 24 | 0.503563 | 2.877445 | 13 | 0.320059 | 2.962939 | 11 |
| VRC | −0.065556 | 49 | 0.848866 | | | | | | | |
| WCB | 0.704429 | 49 | 0.607683 | 1.810214 | 2 | 0.101319 | | | | |
| 0.05 | 11 | | | 20 | | | 18 | | | 15 |
| 0.025 | 7 | | | 16 | | | 17 | | | 14 |
| 0.01 | 3 | | | 12 | | | 16 | | | 13 |
| 0.005 | 3 | | | 6 | | | 12 | | | 12 |

| Subject | Cluster 7 P0.005 SD | Cluster 7 P0.001 Mean_T | Cluster 7 P0.001 No. Voxels | Cluster 7 P0.001 SD | Cluster 7 P0.0005 Mean_T | Cluster 7 P0.0005 No. Voxels | Cluster 7 P0.0005 SD | Cluster 7 P0.0001 Mean_T | Cluster 7 P0.0001 No. Voxels | Cluster 7 P0.0001 SD |
|---|---|---|---|---|---|---|---|---|---|---|
| AKM | 0.072711 | | | | | | | | | |
| ALS | 0.092599 | | | | | | | | | |
| AMD | 1.405984 | 4.495549 | 3 | 1.330881 | 5.083308 | 2 | 1.800269 | 5.083308 | 2 | 1.800269 |
| ARG | | | | | | | | | | |
| ASF | | | | | | | | | | |
| BJM | 0.328028 | 3.42161 | 11 | 0.197055 | 3.538892 | 7 | 0.146862 | 3.797349 | 1 | 1E+30 |
| BVM | 0.391585 | 3.548803 | 7 | 0.129078 | 3.548803 | 7 | 0.129078 | 3.79043 | 1 | 1E+30 |
| CAP | | | | | | | | | | |
| CMB | 0.408665 | 3.535936 | 11 | 0.25977 | 3.698359 | 7 | 0.17325 | 3.934449 | 2 | 0.152613 |
| CRJ | 0.264135 | 3.341548 | 8 | 0.137551 | 3.473367 | 4 | 0.040514 | | | |
| DCM | | | | | | | | | | |
| DLR | | | | | | | | | | |
| DMH | | | | | | | | | | |
| EBW | 0.259863 | 3.458845 | 1 | 1E+30 | 3.458845 | 1 | 1E+30 | | | |
| ERB | | | | | | | | | | |
| KTM | | | | | | | | | | |
| KWW | 0.462686 | 3.651508 | 21 | 0.308547 | 3.727303 | 18 | 0.265886 | 4.016041 | 6 | 0.238829 |
| LPF | 0.227729 | 3.359981 | 3 | 0.216517 | 3.665807 | 1 | 1E+30 | | | |
| MKS | | | | | | | | | | |
| MLW | 0.080244 | | | | | | | | | |
| MSW | 0.453803 | 3.72173 | 23 | 0.368337 | 3.803508 | 20 | 0.322444 | 4.08954 | 9 | 0.264075 |
| NDP | 0.125944 | | | | | | | | | |

TABLE 9-continued

Voxel Subtraction Method Using Lie – True

Clusters 1, 2, 3, 4, 5, 6 and 7 as defined in Table 6

| | | | | | | | |
|---|---|---|---|---|---|---|---|
| PJK | 0.185395 | 3.148426 | 2 | 0.0077 | | | |
| QLB | | | | | | | |
| RJA | | | | | | | |
| SMJ | | | | | | | |
| SRB | | | | | | | |
| SWS | 0.270149 | 3.309319 | 3 | 0.138189 | 3.39903 | 2 | 0.09487 |
| VRC | | | | | | | |
| WCB | | | | | | | |
| 0.05 | | 11 | | | 10 | | 6 |
| 0.025 | | 11 | | | 10 | | 6 |
| 0.01 | | 11 | | | 10 | | 6 |
| 0.005 | | 10 | | | 9 | | 5 |

NOTE:

P1: All voxels Included, no threshold used

P0.05: $P \leq 0.05$

P0.01: $P \leq 0.01$

P0.005: $P \leq 0.005$

P0.001: $P \leq 0.001$

P0.0005: $P \leq 0.0005$

P0.0001: $P \leq 0.0001$

Mean_T: Averaged T value

No. Voxels: Number of voxels

SD: Standard Deviation

TABLE 10

Threshold Technique - Voxels

| | Cluster 1 P0.0001 No. Voxels | Cluster 2 P0.0001 No. Voxels | Cluster 4 P0.0001 No. Voxels | Cluster 1, 2, 4 | CLUSTER 1 & 2 | CLUSTER 2 | Cluster 1 P0.0001 No. Voxels | Cluster 2 P0.0001 No. Voxels | Cluster 4 P0.0001 No. Voxels | CLUSTER 1, 2, 4 | CLUSTER 1 & 2 | CLUSTER 2 |
|---|---|---|---|---|---|---|---|---|---|---|---|---|
| 1 | 40 | | | 1 | 1 | | 108 | 28 | | 1 | 1 | 1 |
| 2 | | | | | | | 3 | 23 | 8 | 1 | 1 | 1 |
| 3 | | | | | | | 132 | 41 | 23 | 1 | 1 | 1 |
| 4 | | | | | | | | | | | | |
| 5 | | | | | | | | | | | | |
| 6 | | | | | | | | | | | | |
| 7 | | | | | | | 1 | 7 | | 1 | 1 | 1 |
| 8 | | 11 | | 1 | | | | 5 | | 1 | | |
| 9 | | 24 | | 1 | | | | 2 | | 1 | | |
| 10 | | | | | | | | | | | | |
| 11 | | | | | | | | | | | | |
| 12 | | | | | | | 3 | | | 1 | 1 | |
| 13 | 52 | 2 | | 1 | 1 | 1 | 112 | 47 | 37 | 1 | 1 | 1 |
| 14 | | | 3 | 1 | | | 52 | 8 | 47 | 1 | 1 | 1 |
| 15 | 139 | 119 | 31 | 1 | 1 | 1 | 237 | 183 | 81 | 1 | 1 | 1 |
| 16 | 7 | 9 | 5 | 1 | 1 | 1 | 25 | 15 | 21 | 1 | 1 | 1 |
| 17 | | | | | | | 1 | | 2 | 1 | 1 | |
| 18 | | | | | | | | | | | | |
| 19 | 1 | 1 | 9 | 1 | 1 | 1 | 148 | 56 | 83 | 1 | 1 | 1 |

TABLE 10-continued

| | | | | | | | | | | | | |
|---|---|---|---|---|---|---|---|---|---|---|---|---|
| 20 | 7 | 3 | 28 | 1 | 1 | 1 | 117 | 92 | 46 | 1 | 1 | 1 |
| 21 | | 19 | 10 | 1 | 1 | 1 | 10 | 59 | 37 | 1 | 1 | 1 |
| 22 | | | | | | | 3 | 104 | | 1 | 1 | 1 |
| 23 | 69 | 26 | 11 | 1 | 1 | 1 | 211 | 128 | 86 | 1 | 1 | 1 |
| 24 | | | | | | | | 5 | 5 | 1 | 1 | 1 |
| 25 | | | 1 | 1 | | | 30 | | 4 | 1 | 1 | |
| 26 | 1 | | 14 | 1 | 1 | | | | 8 | 1 | | |
| 27 | 13 | 16 | 1 | 1 | 1 | 1 | 54 | 3 | 2 | 1 | 1 | 1 |
| 28 | | | | | | | 25 | | 21 | 1 | 1 | |
| 29 | 5 | | | 1 | 1 | | 91 | 46 | | 1 | 1 | 1 |
| 30 | 10 | | 1 | 1 | 1 | | | | 3 | 1 | 1 | 1 |
| | | | | | | | 24 | 21 | 17 | | | |
| | 0.533333333 | 0.4 | | 0.26666667 | | | 0.8 | 0.7 | 0.56666667 | | | |

| | CLUSTER 1, 2, 4 | | | CLUSTER 1, 2 | | | CLUSTER 2 | | |
|---|---|---|---|---|---|---|---|---|---|
| NOTE: | | LIE | TRUTH | | LIE | TRUTH | | LIE | TRUTH |
| P 0.0001: | POSITIVE | 24 | 16 | 40 POSITIVE | 21 | 12 | 39 POSITIVE | 17 | 8 | 25 |
| P ≤ 0.0001 | NEGATIVE | 6 | 14 | 20 NEGATIVE | 9 | 18 | 21 NEGATIVE | 23 | 22 | 45 |
| | | 30 | 30 | 60 | 30 | 30 | 60 | 30 | 30 | 60 |

TABLE 11

Mean and Median Values for the Lie − True (L − T), True − Lie (T − L), Lie − Neutral (L − N) and True − Neutral (T − N) contrasts

| | L − T | T − L | L − N | T − N |
|---|---|---|---|---|
| Mean value for voxel activation | | | | |
| Cluster 1 | 95.4 | 7.6 | 176.8 | 95 |
| Cluster 2 | 87.9 | 3.7 | 135 | 70.8 |
| Cluster 4 | 52.6 | 4.0 | 67.4 | 37.7 |
| Cluster 1, 2 and 4 | 236 | 15.3 | 379.2 | 203.5 |
| Median value for voxel activation | | | | |
| Cluster 1 | 84.5 | 0 | 187.5 | 67 |
| Cluster 2 | 69.5 | 0 | 121 | 42 |
| Cluster 4 | 56.5 | 0 | 46.9 | 34 |
| Cluster 1, 2 and 4 | 210 | 2 | 207.2 | 136.5 |

TABLE 12

Significance of the different contrasts using values from Table 11. t-Test

| | Ho: L − T = T − L | | Ho: L − N = T − N | |
|---|---|---|---|---|
| | T-Value | p-value | T-Value | p-value |
| Cluster 1 | 5.8495 | <0.000000 | 3.2755 | 0.001783 |
| Cluster 2 | 6.4798 | <0.000000 | 3.0921 | 0.003054 |
| Cluster 4 | 6.7232 | <0.000000 | 2.6453 | 0.010486 |
| Cluster 1, 2 and 4 | 7.6069 | <0.000000 | 3.4462 | 0.001064 |

Values reflect a two-tailed t-test.

TABLE 13

Voxel Subtraction Method Using Lie and True Questions

| | (L − T) − (T − L) | | (L − N) − (T − N) | | |
|---|---|---|---|---|---|
| | Number | % | Number | % | Significant |
| Cluster 1 | | | | | |
| Correct | 27 | 93% | 28 | 93% | Not sig. |
| Wrong | 2 | 7% | 2 | 7% | |
| Indeterminate | 1 | N/A | 0 | N/A/ | |
| Cluster 2 | | | | | |
| Correct | 29 | 97% | 25 | 86% | Not sig. |
| Wrong | 1 | 3% | 4 | 14% | |
| Indeterminate | 0 | N/A | 1 | N/A | |
| Cluster 4 | | | | | |
| Correct | 26 | 90% | 24 | 89% | Not sig. |
| Wrong | 2 | 7% | 3 | 11% | |
| Indeterminate | 2 | 0% | 3 | N/A | |
| Cluster 1, 2 and 4 | | | | | |
| Correct | 27 | 93% | 28 | 93% | Not sig. |
| Wrong | 2 | 7% | 2 | 7% | |
| Indeterminate | 1 | N/A | 0 | N/A | |

What is claimed is:

1. A method for measuring brain activity of a subject comprising the steps of:
  (a) subjecting the subject to at least one first stimulus of interest, measuring brain activity of the subject during a first period of interest, and generating a first brain map for the subject from the measured brain activity;
  (b) subjecting the subject to at least one second stimulus of interest, measuring brain activity of the subject during a second period of interest, and generating a second brain map for the subject from the measured brain activity;

(c) a computer generating a first contrast brain map for the subject by subtracting a parameter of interest of the second brain map from the parameter of interest of the first brain map;

(d) a computer generating a second contrast brain map for the subject by subtracting the parameter of interest of the first brain map from the parameter of interest of the second brain map for a plurality of voxels in the maps; and (e) determining if the subject responded to the first or the second stimulus of interest as follows:

i) if the parameter of interest of the first contrast map is greater than the parameter of interest of the second contrast map, then the subject is determined to have responded to the first stimulus of interest;

ii) if the parameter of interest of the second contrast map is greater than the parameter of interest of the first contrast map, then the subject is determined to have responded to the second stimulus of interest.

2. The method of claim 1, wherein at least one of the first and the second stimulus of interest comprises asking the subject to perform a task.

3. The method of claim 2, wherein the task is a motor task.

4. The method of claim 3, wherein the task comprises taking a ring or a watch.

5. The method of claim 1, wherein at least one of the first and the second stimulus of interest is selected from the group consisting of a sound, a picture, an aurally-presented question and a visually-presented question.

6. The method of claim 5, wherein the subject is asked to respond to the first and the second stimuli either truthfully and deceptively, or deceptively and truthfully.

7. The method of claim 6, wherein the truthful response to the stimuli is known.

8. The method of claim 1, wherein the parameter of interest is a number of activated voxels.

9. The method of claim 1, wherein the contrast brain map is generated for at least one specific brain region.

10. The method of claim 9, wherein the least one specific brain region is selected from the group of brain regions consisting of: prefrontal cortex, limbic cortex, anterior cruciate, temporal cortex, parietal cortex, caudate, hypothalamus, cerebellum, orbitofrontal cortex, anterior cingulate cortex, middle temporal cortex, insula, cuneus, post-central gyrus, pre-central gyrus, superior temporal gyrus, right anterior cingulate cortex, right inferior frontal cortex, right orbitofrontal cortex, left middle temporal cortex and right middle frontal cortex.

11. The method of any one of claim 1-8, and 9, or 10, further comprising displaying at least one of the brain maps.

12. The method of any one of claim 1-8, and 9, or 10 wherein the brain activity of the subject is measured by an fMRI device.

* * * * *